United States Patent
Plemper et al.

(10) Patent No.: US 9,365,523 B2
(45) Date of Patent: Jun. 14, 2016

(54) IMIDAZOLYL AMIDE COMPOUNDS AND USES RELATED THERETO

(75) Inventors: Richard K. Plemper, Decatur, GA (US); James P. Snyder, Atlanta, GA (US); Aiming Sun, Atlanta, GA (US); John M. Ndungu, Decatur, GA (US); Jeong-Joong Yoon, Decatur, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 14/006,259

(22) PCT Filed: Mar. 28, 2012

(86) PCT No.: PCT/US2012/030866
§ 371 (c)(1),
(2), (4) Date: Nov. 25, 2013

(87) PCT Pub. No.: WO2012/135296
PCT Pub. Date: Oct. 4, 2012

(65) Prior Publication Data
US 2014/0080828 A1    Mar. 20, 2014

Related U.S. Application Data

(60) Provisional application No. 61/470,020, filed on Mar. 31, 2011.

(51) Int. Cl.
| | |
|---|---|
| C07D 235/28 | (2006.01) |
| A61K 31/4184 | (2006.01) |
| A61K 31/422 | (2006.01) |
| A61K 31/427 | (2006.01) |
| A61K 31/4439 | (2006.01) |
| A61K 31/454 | (2006.01) |
| A61K 31/496 | (2006.01) |
| A61K 31/506 | (2006.01) |
| A61K 31/53 | (2006.01) |
| A61K 31/5377 | (2006.01) |
| A61K 45/06 | (2006.01) |
| C07D 401/12 | (2006.01) |
| C07D 403/12 | (2006.01) |
| C07D 413/12 | (2006.01) |
| C07D 417/12 | (2006.01) |
| C07D 401/04 | (2006.01) |
| C07D 401/06 | (2006.01) |
| C07D 403/06 | (2006.01) |

(52) U.S. Cl.
CPC .......... *C07D 235/28* (2013.01); *A61K 31/4184* (2013.01); *A61K 31/422* (2013.01); *A61K 31/427* (2013.01); *A61K 31/4439* (2013.01); *A61K 31/454* (2013.01); *A61K 31/496* (2013.01); *A61K 31/506* (2013.01); *A61K 31/53* (2013.01); *A61K 31/5377* (2013.01); *A61K 45/06* (2013.01); *C07D 401/04* (2013.01); *C07D 401/06* (2013.01); *C07D 401/12* (2013.01); *C07D 403/06* (2013.01); *C07D 403/12* (2013.01); *C07D 413/12* (2013.01); *C07D 417/12* (2013.01)

(58) Field of Classification Search
USPC ........................................ 548/307.1
See application file for complete search history.

(56) References Cited

U.S. PATENT DOCUMENTS

| | | |
|---|---|---|
| 3,720,686 A | 3/1973 | Narayanan et al. |
| 2004/0067976 A1 | 4/2004 | Priestley |
| 2005/0288258 A1 | 12/2005 | Diana |

FOREIGN PATENT DOCUMENTS

| | | | | |
|---|---|---|---|---|
| JP | 4-139172 | A | * | 5/1992 |
| JP | 2001-048867 | | | 2/2001 |
| JP | 2001/048867 | A | * | 2/2001 |
| WO | 9835944 | | | 8/1998 |
| WO | 2009149054 | | | 12/2009 |
| WO | 2010042785 | | | 4/2010 |

OTHER PUBLICATIONS

Sun et al., ACS Medicinal Chemistry Letters, Aug. 23, 2011, 2(11), pp. 798-803 and Supporting Information.*
National Center for Biotechnology Information. PubChem Compound Database; CID=25344818, http://pubchem.ncbi.nlm.nih.gov/summary/summary.cgi?cid=25344818 (accessed Mar. 25, 2015), create date May 27, 2009.*
National Center for Biotechnology Information. PubChem Compound Database; CID=40785829, http://pubchem.ncbi.nlm.nih.gov/summary/summary.cgi?cid=40785829 (accessed Mar. 25, 2015), create date May 30, 2009.*
National Center for Biotechnology Information. PubChem Compound Database; CID=41298675, http://pubchem.ncbi.nlm.nih.gov/summary/summary.cgi?cid=41298675 (accessed Mar. 25, 2015), create date May 30, 2009.*

(Continued)

*Primary Examiner* — Laura L. Stockton
(74) *Attorney, Agent, or Firm* — Emory Patent Group

(57) ABSTRACT

This disclosure relates to antiviral compounds disclosed herein and uses related thereto. In certain embodiments, the disclosure relates to pharmaceutical compositions comprising 2-((benzo[d]imidazol-2-yl)thio)-N-phenylpropanamide derivatives, N-phenyl-2-((1-phenyl-benzo[d]imidazol-2-yl)thio)propanamide derivatives, or 2-((benzo[d]imidazol-2-yl)thio)-N-(2-chloro-4-methylphenyl)propanamide derivatives. The derivatives may be substituted with one or more substituents. Typically, the pharmaceutical composition comprises a compound of Formula (I), or salt, prodrug, or ester thereof wherein X, Y, and R1 to R7 are described herein.

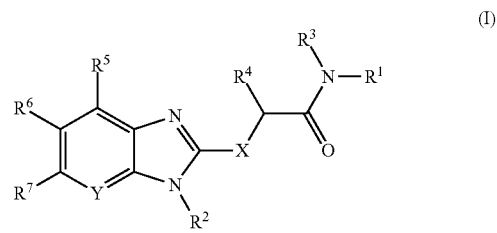

(I)

1 Claim, 14 Drawing Sheets

(56) References Cited

OTHER PUBLICATIONS

National Center for Biotechnology Information. PubChem Compound Database; CID=41298664, http://pubchem.ncbi.nlm.nih.gov/summary/summary.cgi?cid=41298664 (accessed Mar. 25, 2015), create date May 30, 2009.*

Chemical Abstracts Registry No. 1331868-56-4, indexed in the Registry file on STN CAS Online Sep. 13, 2011.*

An English translation of Takahashi et al., JP 2001-48867 A, 2001.*

An English translation of Hirai et al., JP 4-139172 A, 1992.*

Yoon et al., High-Throughput Screening Based Identification of Paramyxovirus Inhibitors, J Biomol Screen. Aug. 2008 ; 13(7): 591-608.

Aiming Sun et al., 'Host-Directed Inhibitors of Myxoviruses: Synthesis and in Vitro Biochemical Evaluation', ACS Medicinal Chemistry Letters, Aug. 23, 2011, vol. 2, No. 11, pp. 798-803.

Chemical Abstracts Registry No. 1331868-56-4, Sep. 13, 2011.

PubChem Compound Database; CID=25344818 , May 27, 2009.

PubChem Compound Database; CID=40785829 , May 30, 2009.

PubChem Compound Database; CID=41298675, May 30, 2009.

PubChem Compound Database; CID=41298664, May 30, 2009.

Extended European Search Report issued by the European Patent Office in Application No. 12763937.5 on Aug. 19, 2014.

Krumm et al. "Potent Host-Directed Small-Molecule Inhibitors of Myxovirus RNA-Dependent RNA-Polymerases" PLoS ONE, 2011; 6(5): e20069., published May 16, 2011.

* cited by examiner

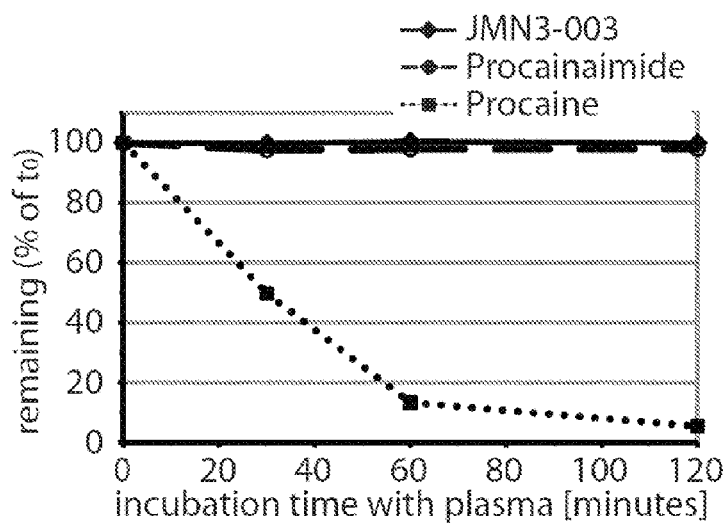

FIGURE 3B

| Host Cell | | Starting Titer[a] | EC$_{50}$[b] |
| --- | --- | --- | --- |
| | | Influenza A/WSN yields in controls | Inhibition of Influenza A/WSN |
| Cell Line | Origin | [pfu/ml] | [μM] |
| HT1080 | Human | $1.5 \times 10^6$ | $0.06 \pm 0.002$ |
| HeLa | Human | $1.6 \times 10^3$ | $0.02 \pm 0.01$ |
| MDCK | Canine-dog | $3.0 \times 10^7$ | $0.01 \pm 0.08$ |
| NIH-3T3 | Rodent-mouse | $8.4 \times 10^6$ | >10 |
| MEL B16 | Rodent-mouse | $5.3 \times 10^5$ | >10 |
| BHK-21 | Rodent-Syrian hamster | $1.7 \times 10^7$ | $0.08 \pm 0.01$ |
| CHO | Rodent-Chinese hamster | $1.5 \times 10^5$ | $0.07 \pm 0.01$ |
| DF-1 | Avian-chicken | $1.3 \times 10^6$ | >10 |

FIGURE 11

| Compound | Orthomyxoviridae[a] | | | |
|---|---|---|---|---|
| | Influenza A/WSN | Influenza A/PR/8/34 | SOI Influenza A/Texas | SOI Influenza A/Mexico |
| | $EC_{50}$ [µM] | | | |
| JMN3-003 | 0.01 ± 0.008 | 0.01 ± 0.001 | 0.04 ± 0.01 | 0.01 ± 0.003 |
| AS-136A | none detected | ND | ND | ND |

Paramyxoviridae

| RSV[b] (Long) | MuV[b] (S. Africa) | HPIV3[b] | MeV[c] (Alaska) |
|---|---|---|---|
| 0.07 ± 0.01 | 0.033 ± 0.031 | 0.08 ± 0.01 | 0.03 ± 0.02 |
| none detected | none detected | none detected | 0.03[e] (0.01–0.05) |

SEQUENCE LISTING

<160> NUMBER OF SEQ ID NOS: 13

<210> SEQ ID NO 1
<211> LENGTH: 22
<212> TYPE: PRT

<213> ORGANISM: Artificial Sequence
<220> FEATURE:
<223> OTHER INFORMATION: Amplification Primer

<400> SEQUENCE: 1

Gly Ala Cys Cys Arg Ala Thr Cys Cys Thr Gly Thr Cys Ala Cys Cys
1 5 10 15

Thr Cys Thr Gly Ala Cys
20

<210> SEQ ID NO 2
<211> LENGTH: 24
<212> TYPE: PRT
<213> ORGANISM: Artificial Sequence
<220> FEATURE:
<223> OTHER INFORMATION: Amplification Primer

<400> SEQUENCE: 2

Ala Gly Gly Gly Cys Ala Thr Thr Tyr Thr Gly Gly Ala Cys Ala Ala
1 5 10 15

Ala Lys Cys Gly Thr Cys Thr Ala
20

<210> SEQ ID NO 3
<211> LENGTH: 24
<212> TYPE: PRT
<213> ORGANISM: Artificial Sequence
<220> FEATURE:
<223> OTHER INFORMATION: Amplification Primer

<400> SEQUENCE: 3

Thr Gly Cys Ala Gly Thr Cys Cys Thr Cys Gly Cys Thr Cys Ala Cys
1 5 10 15

Thr Gly Gly Gly Cys Ala Cys Gly
20

<210> SEQ ID NO 4
<211> LENGTH: 15
<212> TYPE: PRT
<213> ORGANISM: Artificial Sequence
<220> FEATURE:
<223> OTHER INFORMATION: Antigenome-specific primer

<400> SEQUENCE: 4

Gly Cys Thr Cys Cys Cys Thr Cys Thr Gly Gly Thr Thr Gly Thr
1 5 10 15

<210> SEQ ID NO 5
<211> LENGTH: 19
<212> TYPE: PRT
<213> ORGANISM: Artificial Sequence
<220> FEATURE:
<223> OTHER INFORMATION: Primer

<400> SEQUENCE: 5

Ala Gly Thr Ala Gly Ala Ala Ala Cys Ala Ala Gly Gly Thr Ala Gly
1 5 10 15

Thr Thr Thr

<210> SEQ ID NO 6
<211> LENGTH: 16
<212> TYPE: PRT
<213> ORGANISM: Artificial Sequence
<220> FEATURE:
<223> OTHER INFORMATION: Primer

<400> SEQUENCE: 6

Ala Ala Cys Cys Ala Gly Gly Thr Cys Ala Cys Ala Cys Ala Gly
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Primer

<400> SEQUENCE: 7

Gly Thr Thr Gly Thr Cys Thr Gly Ala Thr Ala Thr Thr Thr Cys Thr
1               5                   10                  15

Gly Ala Cys

<210> SEQ ID NO 8
<211> LENGTH: 30
<212> TYPE: PRT
<213> ORGANISM: Artificial Sequence
<220> FEATURE:
<223> OTHER INFORMATION: Primer

<400> SEQUENCE: 8

Gly Thr Cys Cys Ala Cys Cys Ala Thr Gly Gly Gly Thr Cys Thr Cys
1               5                   10                  15

Ala Ala Gly Gly Thr Gly Ala Ala Cys Gly Thr Cys Thr Cys
            20                  25                  30

<210> SEQ ID NO 9
<211> LENGTH: 18
<212> TYPE: PRT
<213> ORGANISM: Artificial Sequence
<220> FEATURE:
<223> OTHER INFORMATION: Primer

<400> SEQUENCE: 9

Cys Ala Gly Thr Thr Ala Thr Thr Gly Ala Gly Gly Ala Gly Ala Gly
1               5                   10                  15

Thr Thr

<210> SEQ ID NO 10
<211> LENGTH: 18
<212> TYPE: PRT
<213> ORGANISM: Artificial Sequence
<220> FEATURE:
<223> OTHER INFORMATION: Primer

<400> SEQUENCE: 10

Thr Ala Gly Cys Thr Cys Cys Ala Gly Thr Gly Cys Thr Gly Gly Thr
1               5                   10                  15

Cys Thr

<210> SEQ ID NO 11
<211> LENGTH: 19
<212> TYPE: PRT
<213> ORGANISM: Artificial Sequence
<220> FEATURE:
<223> OTHER INFORMATION: Primer

<400> SEQUENCE: 11

Ala Ala Gly Gly Cys Cys Cys Thr Cys Cys Thr Thr Thr Cys Ala Gly
1               5                   10                  15

```
Thr Cys Cys

<210> SEQ ID NO 12
<211> LENGTH: 20
<212> TYPE: PRT
<213> ORGANISM: Artificial Sequence
<220> FEATURE:
<223> OTHER INFORMATION: Primer

<400> SEQUENCE: 12

Ala Ala Cys Cys Gly Ala Gly Gly Thr Cys Gly Ala Ala Ala Cys Gly
1               5                  10                  15

Cys Cys Thr Ala
            20

<210> SEQ ID NO 13
<211> LENGTH: 19
<212> TYPE: PRT
<213> ORGANISM: Artificial Sequence
<220> FEATURE:
<223> OTHER INFORMATION: Primer

<400> SEQUENCE: 13

Ala Gly Cys Ala Thr Cys Cys Ala Cys Ala Gly Cys Ala Cys Thr Cys
1               5                  10                  15

Thr Gly Cys
```

IMIDAZOLYL AMIDE COMPOUNDS AND USES RELATED THERETO

CROSS REFERENCE TO RELATED APPLICATIONS

This Application is a USC 371 filing of International Application PCT/US2012/030866, filed Mar. 28, 2012, which claims the benefit of priority to U.S. Provisional Application No. 61/470,020 filed Mar. 31, 2011, hereby incorporated by reference in their entireties.

ACKNOWLEDGEMENTS

This invention was made with Government support under Grant Nos. AI056179 and AI071002 awarded by the National Institutes of Health. The Government has certain rights in the invention.

BACKGROUND

Myxoviruses, i.e., viruses in orthomyxoviridae and paramyxoviridae families, are RNA viruses. Influenza is in the orthomyxoviridae family. Influenza virus is the leading cause of morbidity and mortality from respiratory disease in North America despite the existence of vaccine prophylaxis. This is due to the fact that the vaccines currently in use reduce illness in approximately 70% of healthy adults when homologous to the prevalent circulating virus, but protection in the elderly reaches only approximately 40%. Vaccine efficacy is reduced substantially when the circulating strains differ from those constituting the vaccine.

Current influenza drugs have limited efficacy. For example, Oseltamivir (Tamiflu) is an antiviral drug that slows the spread of influenza virus. However, it has been reported that Tamiflu offered mild benefits in terms of duration of symptoms for healthy adults if taken within 24 hours of onset of symptoms, but there was no clear evidence it prevented lower respiratory tract infections or other complications of influenza. Thus, there is a need to identify improved methods for treating or preventing influenza infections.

Measles virus (MV), a representative of the paramyxovirus family, is one of the most infectious viruses identified. Despite enhanced efforts for global implementation of a live-attenuated vaccine, MV is a principle cause of morbidity, and infection results in approximately 300,000 to 400,000 deaths annually worldwide, rendering the virus the leading cause of childhood deaths from a vaccine-preventable disease globally. Low vaccination coverage in parts of the developing world and insufficient or declining herd immunity in several developed countries contribute to continued MV activity. In addition to a substantial immunosuppression that lasts several months, complications associated with MV infection include acute encephalitis and subacute sclerosing panencephalitis (SSPE), a late lethal sequela that manifests itself years after the primary infection. Currently, Ribavirin is the only drug approved for the treatment of some paramyxovirus infections. It has been used experimentally against MV but with limited efficacy. Thus, there is a need to identify additional agents to treat or prevent MV.

Yoon et al., J Biomol Screen., 2008, 13(7): 591-608 disclose a high-throughput screening protocol that permits screening against non-attenuated wild type MV strains.

SUMMARY

This disclosure relates to antiviral compounds disclosed herein and uses related thereto. In certain embodiments, the disclosure relates to pharmaceutical compositions comprising 2-((benzo[d]imidazol-2-yl)thio)-N-phenylpropanamide derivatives, N-phenyl-2-((1-phenyl-benzo[d]imidazol-2-yl)thio)propanamide derivatives, or 2-((benzo[d]imidazol-2-yl)thio)-N-(2-chloro-4-methylphenyl)propanamide derivatives. The derivatives may be substituted with one or more substituents. Typically, the pharmaceutical composition comprises a compound of formula I:

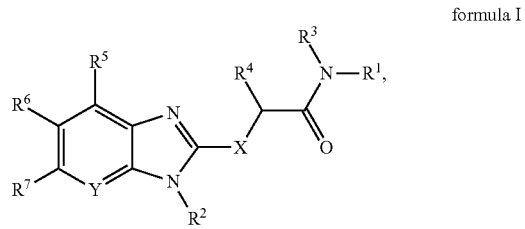

formula I or salt, prodrug, or ester thereof wherein X, Y, and $R^1$ to $R^7$ are described herein. Further, the pharmaceutical compositions typically comprise the compound as a pharmaceutically acceptable salt in combination with a pharmaceutically acceptable excipient such as a dilutant, carrier, filler, or buffer. The pharmaceutical composition may be in the form of a pill, gel, capsule, tablet, or saline buffer solution. The excipient may be, but not limited to, an anti-adherent such as magnesium stearate, a binder such as a sugar, saccharide, or cellulose, a coating such as hydroxypropyl methylcellulose and gelatin, a disintegrant such as crospovidone and croscarmellose sodium, a filler such as water, salts, sugars, celluloses, calcium phosphates, fats, and oils, a lubricant such as talc, silica, fats, and magnesium stearate.

In certain embodiments, the disclosure relates to uses of compounds disclosed herein in the production of a medicament for the treatment or prevention of a pathogenic infection.

In certain embodiments, the disclosure relates to methods of treating a pathogenic infection. The methods may comprise administering a pharmaceutical composition as provided herein to a subject at risk of, exhibiting symptoms of, suspected of, or diagnosed with a viral infection. In certain embodiments, the virus is an RNA virus or a DNA virus that replicates through an RNA intermediate. In certain embodiments, the RNA virus is a positive, negative sense, or ambisense single stranded virus. In certain embodiments, the RNA virus is double stranded. In certain embodiments, the RNA virus is a retrovirus. RNA viruses contemplated include human parainfluenza viruses, influenza A virus including subtype H1N1, influenza B virus, influenza C virus, rotavirus A, rotavirus B, rotavirus C, rotavirus D, rotavirus E, human metapneumovirus, SARS coronavirus, parvovirus B19, hepatitis A, hepatitis C, hepatitis E, yellow fever virus, measles virus, mumps virus, respiratory syncytial virus, norovirus, west nile virus, dengue virus, rubella virus, rabies virus, ebola virus, and marburg virus, distemper virus, rinderpest virus, and Nipah and Hendra viruses.

In certain embodiments, the subject is diagnosed with JC virus (JCV), BK virus, Merkel cell polyomavirus, coxsackie A virus, lymphocytic choriomeningitis virus (LCMV), rinderpest virus, California encephalitis virus, hantavirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis B, hepatitis D, or human immunodeficiency virus (HIV).

In certain embodiments, RNA tick-borne viruses are contemplated such as those in the families: Asfarviridae, Reoviridae, Rhabdoviridae, Orthomyxoviridae, Bunyaviridae, Flaviviridae. Exemplary tick-borne viruses include tick-borne encephalitis virus, Crimean-Congo haemorrhagic fever virus, African swine fever virus, Nairobi sheep disease virus, Banna virus, Tahyna virus, louping ill virus, Powassan virus, Kyasanur Forest disease virus, and Omsk hemorrhagic fever virus.

In certain embodiments, the pharmaceutical composition is administered in combination with one or more additional/second antiviral agent(s).

In certain embodiments, the disclosure relates to methods of preparing compounds disclosed herein, e.g., mixing the starting materials under conditions to provide the products.

BRIEF DESCRIPTION OF THE FIGURES

FIGS. 3A and 3B show data suggesting JMN3-003 is metabolically stable in vitro. A) Incubation of the article with human liver S9 fractions for up to 60 minutes, followed by LC-MS/MS analysis of the material remaining. Two analogs of JMN3-003, JMN5-165 chemical name N-(2-chloro-4-methylphenyl)-2-((1-(phenylsulfonyl)-benzo[d]imidazol-2-yl)thio)propanamide, and JMN5-166 chemical name 2-((1-benzoyl-benzo[d]imidazol-2-yl)thio)-N-(2-chloro-4-methylphenyl)propanamide, showed less stability and are included for comparison. Values represent averages of 2 replicates, calculated half-lives (t½) are given in the figure captures. B) Incubation of JMN3-003 for up to 120 minutes with human plasma derived from mixed, healthy donors, followed by LC-MS/MS quantification of the material remaining. Unstable procaine and stable procainamide were examined equally for comparison. Values represent averages of three experiments±SD.

FIG. 11 shows a table with data on the antiviral activity of JMN3-003 is host cell specific species. Active concentrations (EC$_{50}$) of JMN3-003 against influenza A/WSN propagated on a variety of different host cell lines. a) titers of progeny virus grown on the different cell lines in the presence of vehicle (DMSO) only were determined through plaque assays on MDCK cells. b) EC$_{50}$ concentrations were determined based on four parameter non-linear regression models generated for individual dose-response curves.

TERMS

Figure 1A:
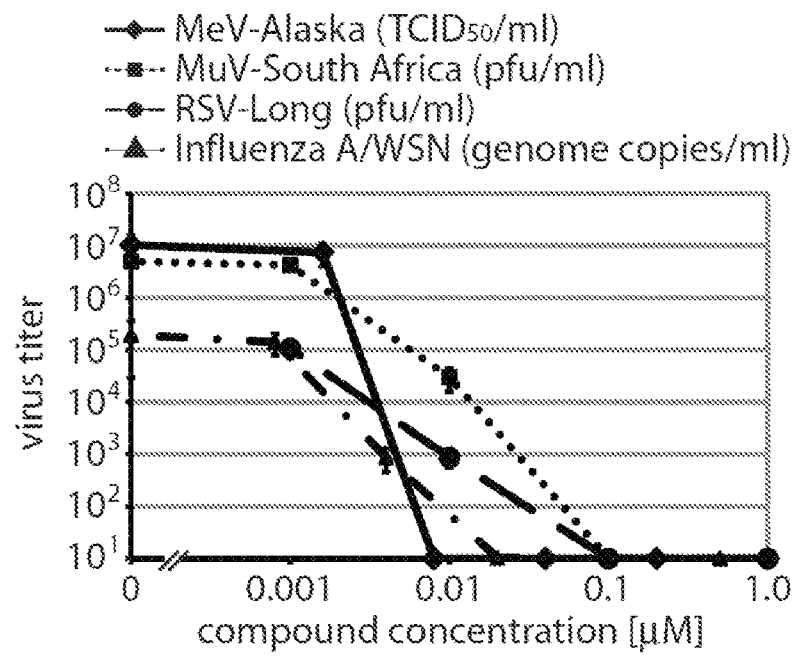
FIG. 1A shows dose-response curves for JMN3-003, chemical name N-(2-chloro-4-methylphenyl)-2-(1-(4-methoxyphenyl)-benzo[d]imidazol-2-yl)thio)propanamide, and MeV-Alaska, MuV-South Africa, RSV Long, and influenza A/WSN(H1N1). Titers of cell-associated progeny paramyxoviruses were determined by TCID50 titration (MeV) or plaque assay (HPIV3, MuV, RSV), genome copy numbers of released influenza particles were quantified through TaqMan RT-PCR. Inhibitory concentrations were calculated based on variable slope four-parameter non-linear regression fittings. Values reflect averages of at least three experiments±SD.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith, Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the disease is eradicated. Rather, embodiments of the present disclosure also contemplate treatment that merely reduces symptoms, and/or delays disease progression.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, the term "combination with" when used to describe administration with an additional treatment means that the agent may be administered prior to, together with, or after the additional treatment, or a combination thereof.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1- butenyl, 2-methyl-2-butenyl, 2,3-dimethyl-2-butenyl, and the like; while representative straight chain and branched alkynyls include acetylenyl, propynyl, 1-butynyl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfamoyl" refers to an alkyl as defined above with the indicated number of carbon atoms attached through a sulfamoyl bridge (i.e., —NHS(=O)2alkyl), and an "Arylsulfamoyl" refers to an alkyl attached through a sulfamoyl bridge (i.e., (i.e., —NHS(=O)2aryl).

"Alkylsulfinyl" refers to an alkyl as defined above with the indicated number of carbon atoms attached through a sulfinyl bridge (i.e. —S(=O)alkyl).

The term "optionally substituted," as used herein, means that substitution is optional and therefore it is possible for the designated atom to be unsubstituted.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine.

An unspecified "R" group may be a hydrogen, lower alkyl, or aryl all of which may be optionally substituted with one or more substituents. Throughout the specification, groups and substituents thereof may be chosen to provide stable moieties and compounds.

DETAILED DESCRIPTION

By combining automated library screening with counter-screens against a variety of related viral pathogens of the myxovirus families, antiviral compounds have been discovered. Although it is not intended that certain embodiments of the disclosure be limited by any particular mechanism, it is believed that certain compounds adhere to the profile of a host-directed antiviral based on several lines of evidence. First, antiviral activity is host cell species-dependent, indicating specific interaction with a distinct host factor rather than a viral component. Host cell-specific activity is incompatible with compound docking to conserved viral factors (i.e. carbohydrate structures exposed on viral envelope glycoproteins as exemplified by antiviral lectins such as pradimicin A) or an undesirable unspecific, promiscuous mode of action. Second, affinities against a panel of human pathogens of the paramyxovirus family as well as laboratory adapted and wild type influenza virus isolates were similar throughout (average EC50 concentrations are ~40 nM). Equivalent active concentrations argue against compound docking to distinct viral components and suggest that inhibition of distinct myxovirus families follows the same MOA. Third, in vitro adaptation attempts to induce viral resistance were unsuccessful even after extended exposure times to the drug. Induced resistance in less than 30 days to a pathogen-directed MeV RdRp inhibitor was analyzed in parallel.

Mechanistic analysis of the bioactivity of a typical compound, the JMN3-003 compound, through characterization of exposed cells and time-of-addition experiments revealed two distinct phenotypes, a temporary cell cycle arrest in the G1/S phase and an arrest in the myxovirus life cycle at a post-entry step. The bulk of experimental data demonstrate that host cell cycle arrest per se has no inhibitory effect on replication of paramyxoviruses such as MeV. Not only does the virus itself induce a G1/S-phase arrest in infected T lymphocytes, it was found that exposure of infected cells to Alsterpaullone, a potent blocker of G1/S-phase cell cycle progression through nanomolar inhibition of cellular cyclin-dependent kinases, did not affect the extent of virus replication even at concentrations exceeding reported Alsterpaullone EC50 values by more than 1.000-fold. Likewise, consistent with the notion that the antiviral activity of JMN3-003 is not based on cell cycle arrest itself, virus inhibition was not restricted to the context of immortalized, rapidly dividing tissue culture cell lines but extended with equal potency to primary human PBMCs.

Reversible cell cycle arrest and block of virus replication indicate non-covalent docking of JMN3-003 to its target structures, which is corroborated by the compound's stability, low chemical reactivity profile and the complete absence of virucidal activity in pre-incubation settings. An inhibition profile of JMN3-003 closely mimicking that of AS-136A, the pathogen directed blocker of MeV RdRp targeting the viral L polymerase protein, and the block in viral RdRp activity in the context of viral infection and minireplicon reporter assays by JMN3-003 consistently point towards interaction of the compound with a host co-factor essential for RdRp function as the basis for its antiviral activity. While viral RdRp depends on a variety of host cell components, unperturbed cellular mRNA synthesis and, thus, uninterrupted host RNA polymerase function in the presence of compound exclude interference of JMN3-003 with essential transcription initiation factors. This observation considerably narrows the pool of candidate host factors that constitute possible cellular targets for the compound.

Recently, accumulating evidence has implicated host cell kinases as regulators of the activity of RdRp complexes of a diverse set of negative-strand RNA viruses. For instance, host cell kinases of the PI3K-Akt pathway reportedly manipulate paramyxovirus RdRp activity through Akt-mediated phosphorylation of the viral phosphoprotein, an essential component of the RdRp complex. Furthermore, Akt activity itself is upregulated through activation of PI3K during influenza A infection via direct interaction of the viral NS1 protein with PI3K. In the case of MeV, however, data suggests that Akt inhibition causes a moderate reduction in virus release, whereas titers of cell-associated progeny particles remain unchanged. While this rules out the PI3K-Akt pathway as a direct target for JMN3-003, it illuminates the intricate regulatory interactions between pathogen and host, which provide a wealth of possible points of entry for antiviral intervention.

Compounds

In certain embodiments, the disclosure relates to compounds and pharmaceutical compositions comprising compounds of Formula I:

Formula I or salts, prodrugs, or esters thereof wherein:

X is —S—, —SO—, or —SO$_2$—;

Y is N or C—R$^8$;

R$^1$ is an carbocyclyl, aryl, or heterocyclyl wherein R$^1$ is optionally substituted with one or more, the same or different, R$^9$;

R$^2$ is alkyl, formyl, alkylsulfonyl, arylsulfonyl, carbocyclyl, aryl, or heterocyclyl wherein R$^2$ is optionally substituted with one or more, the same or different, R$^{10}$;

R$^3$ is hydrogen or alkyl, wherein R$^3$ is optionally substituted with one or more, the same or different R$^{11}$;

R$^4$ is hydrogen or alkyl, wherein R$^4$ is optionally substituted with one or more, the same or different R$^{11}$;

R$^5$, R$^6$, R$^7$, and R$^8$ are each individually and independently, hydrogen, halogen, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R$^9$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl, wherein R$^9$ is optionally substituted with one or more, the same or different, R$^{11}$;

R$^{10}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl, wherein R$^{10}$ is optionally substituted with one or more, the same or different, R$^{11}$; and R$^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is not 3,5-dichloro-pyrid-2-yl.

In certain embodiments, $R^1$ is a heterocyclyl selected from furyl, benzofuranyl, thiophenyl, benzothiophenyl, pyrrolyl, indolyl, isoindolyl, azaindolyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl or a heterocarbocyclyl, wherein the heterocyclyl is optionally substituted with one or more, the same or different, $R^9$.

In certain embodiments, $R^1$ is 2-chloro-4-methylphenyl.

In certain embodiments, $R^1$ is phenyl, ortho halogenated phenyl, aryl, thiazol-2-yl, isoxazol-3-yl, or pyrazol-5-yl, or heteroaryl.

In certain embodiments, $R^2$ is carbocyclyl, aryl, or heterocyclyl.

In certain embodiments, $R_2$ is a heterocyclyl.

In certain embodiments, $R^2$ is arylsulfonyl, heterocyclyl, or benzyl.

In certain embodiments, $R^2$ is not 4-methoxyphenyl, 4-methylphenyl, or 3-methylphenyl.

In certain embodiments, $R^1$ is not 3,5-dichloro-pyrid-2-yl and/or $R^2$ is not 4-methoxyphenyl, 4-methylphenyl, or 3-methylphenyl.

In certain embodiments, $R^3$ is hydrogen.

In certain embodiments, $R^4$ is alkyl or methyl.

In certain embodiments, $R^5$, $R^6$, $R^7$, and $R^8$ are each individually and independently hydrogen or halogen.

In certain embodiments, Y is N.

In certain embodiments, the disclosure relates to compounds of Formula IA,

Formula IA

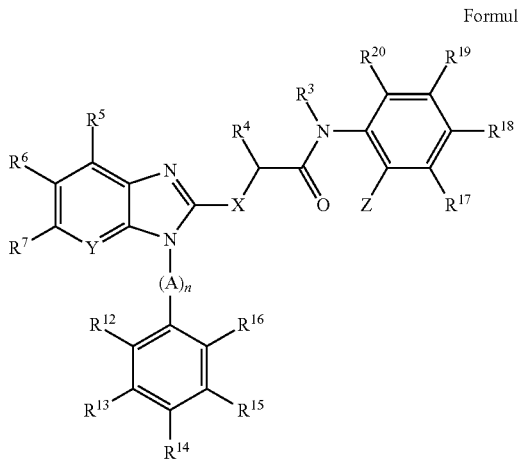

or salts, prodrugs, or esters thereof wherein:

X is —S—, —SO—, or —SO$_2$—;

Y is N or C—$R^8$;

Z is halogen;

A is —CR$^{21}$R$^{22}$—, —SO—, —SO$_2$—, —C=O—, —C=ONH—, or a bond;

n is 0 or 1;

$R^3$ is hydrogen or alkyl, wherein $R^3$ is optionally substituted with one or more, the same or different $R^{11}$;

$R^4$ is hydrogen or alkyl, wherein $R^4$ is optionally substituted with one or more, the same or different $R^{11}$;

$R^5$, $R^6$, $R^7$, $R^8$, $R^{12}$, $R^{13}$, $R^{15}$, $R^{16}$, $R^{17}$, $R^{19}$, and $R^{20}$ are each individually and independently, hydrogen, halogen, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{14}$ is hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{14}$ is optionally substituted with one or more, the same or different, $R^{23}$;

$R^{18}$ is hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{18}$ is optionally substituted with one or more, the same or different, $R^{23}$;

$R^{21}$ and $R^{22}$ are each individually and independently, hydrogen or alkyl optionally substituted with one or more, the same or different, $R^{23}$; and $R^{23}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{14}$ is alkyl.

In certain embodiments, $R^{14}$ is alkoxy.

In certain embodiments, $R^{18}$ is alkyl.

In certain embodiments, $R^{18}$ is alkoxy.

In certain embodiments, the disclosure relates to a compound such as N-(2-chloro-4-methylphenyl)-2-((1-(4-(morpholinomethyl)phenyl)-benzo[d]imidazol-2-yl)thio)propanamide;

N-(2-chloro-4-methylphenyl)-2-(1-(4-(cyanomethoxy)phenyl)-benzo[d]imidazol-2-yl)thio)propanamide;

N-(2-chloro-4-methylphenyl)-2-((1-(4-(2-hydroxyethoxy)phenyl)-benzo[d]imidazol-2-yl)thio)propanamide;

N-(2-chloro-4-methylphenyl)-2-((1-(4-((2-(dimethylamino)ethyl)amino)phenyl)-benzo[d]imidazol-2-yl)thio)propanamide;

N-(2-chloro-4-methylphenyl)-2-((1-(4-((2-(dimethylamino)ethyl)(methyl)amino)phenyl)-benzo[d]imidazol-2-yl)thio)propanamide;

2-((1-(4-(2-acetamidoethoxy)phenyl)-benzo[d]imidazol-2-yl)thio)-N-(2-chloro-4-methylphenyl)propanamide;

N-(2-chloro-4-methylphenyl)-2-((1-(4-(2-oxoethyl)phenyl)-benzo[d]imidazol-2-yl)thio)propanamide;
N-(2-chloro-4-methylphenyl)-2-((1-(4-((4-methylpiperazin-1-yl)methyl)phenyl)-benzo[d]imidazol-2-yl)thio)propanamide;
N-(2-chloro-4-methylphenyl)-2-((1-(4-(2-hydroxyethyl)phenyl)-benzo[d]imidazol-2-yl)thio)propanamide;
N-(2-chloro-4-methylphenyl)-2-((1-(4-(2-(methylamino)ethyl)phenyl)-benzo[d]imidazol-2-yl)thio)propanamide;
2-(4-(2-((1-((2-chloro-4-methylphenyl)amino)-1-oxopropan-2-yl)thio)-benzo[d]imidazol-1-yl)phenoxy)acetic acid;
methyl 2-(4-(2-((1-((2-chloro-4-methylphenyl)amino)-1-oxopropan-2-yl)thio)-benzo[d]imidazol-1-yl)phenoxy)acetate;
2-((1-(4-aminophenyl)-benzo[d]imidazol-2-yl)thio)-N-(2-chloro-4-methylphenyl)propanamide;
N-(2-chloro-4-methylphenyl)-2-((1-(4-hydroxyphenyl)-benzo[d]imidazol-2-yl)thio)propanamide;
N-(2-chloro-4-methylphenyl)-2-((1-(4-ethoxyphenyl)-benzo[d]imidazol-2-yl)thio)propanamide;
N-(2-chloro-4-methylphenyl)-2-((1-(4-(dimethylamino)phenyl)-benzo[d]imidazol-2-yl)thio)propanamide
N-(2-chloro-4-methylphenyl)-2-((1-(4-(4-methylpiperazin-1-yl)phenyl)-benzo[d]imidazol-2-yl)thio)propanamide;
N-(2-chloro-4-methylphenyl)-2-((1-(4-morpholinophenyl)-benzo[d]imidazol-2-yl)thio)propanamide;
N-(2-chloro-4-methylphenyl)-2-((1-(4-(hydroxymethyl)phenyl)-benzo[d]imidazol-2-yl)thio)propanamide;
2-((1-(4-azidophenyl)-benzo[d]imidazol-2-yl)thio)-N-(2-chloro-4-methylphenyl)propanamide;
4-(2-((1-((2-chloro-4-methylphenyl)amino)-1-oxopropan-2-yl)thio)-benzo[d]imidazol-1-yl)benzoic acid;
N-(2-chloro-4-methylphenyl)-2-((1-(4-((dimethylamino)methyl)phenyl)-benzo[d]imidazol-2-yl)thio)propanamide;
methyl 4-(2-((1-((2-chloro-4-methylphenyl)amino)-1-oxopropan-2-yl)thio)-benzo[d]imidazol-1-yl)benzoate;
N-(2-chloro-4-methylphenyl)-2-((1-(4-methoxyphenyl)-benzo[d]imidazol-2-yl)thio)propanamide;
N-(2-chloro-4-methylphenyl)-2-((1-phenyl-benzo[d]imidazol-2-yl)thio)propanamide;
N-(2-chloro-4-methylphenyl)-2-((1-(3-methoxyphenyl)-benzo[d]imidazol-2-yl)thio)propanamide;
N-(2-chloro-4-methylphenyl)-2-((1-(m-tolyl)-benzo[d]imidazol-2-yl)thio)propanamide;
N-(2-chloro-4-methylphenyl)-2-((1-(3,5-dimethoxyphenyl)-benzo[d]imidazol-2-yl)thio)propanamide;
N-(2-chloro-4-methylphenyl)-2-((1-(3-((4-methylpiperazin-1-yl)methyl)phenyl)-benzo[d]imidazol-2-yl)thio)propanamide;
N-(2-chloro-4-methylphenyl)-2-((1-(3-(morpholinomethyl)phenyl)-benzo[d]imidazol-2-yl)thio)propanamide;
3-(2-((1-((2-chloro-4-methylphenyl)amino)-1-oxopropan-2-yl)thio)-benzo[d]imidazol-1-yl)benzoic acid;
N-(2-chloro-4-methylphenyl)-2-((1-(2-(4-methylpiperazin-1-yl)methyl)phenyl)-benzo[d]imidazol-2-yl)thio)propanamide;
N-(2-chloro-4-methylphenyl)-2-((1-(2-(morpholinomethyl)phenyl)-benzo[d]imidazol-2-yl)thio)propanamide;
N-(2-chloro-4-methylphenyl)-2-((1-(3-(hydroxymethyl)phenyl)-benzo[d]imidazol-2-yl)thio)propanamide;
N-(2-chloro-4-methylphenyl)-2-((1-(2-(hydroxymethyl)phenyl)-benzo[d]imidazol-2-yl)thio)propanamide;
N-(2-chloro-4-methylphenyl)-2-((1-cyclohexyl-benzo[d]imidazol-2-yl)thio)propanamide;
N-(2-chloro-4-methylphenyl)-2-((1-(piperidin-4-yl)-benzo[d]imidazol-2-yl)thio)propanamide;
N-(2-chloro-4-methylphenyl)-2-((1-(1-methylpiperidin-4-yl)-benzo[d]imidazol-2-yl)thio)propanamide;
N-(2-chloro-4-methylphenyl)-2-((1-(1-pivaloylpiperidin-4-yl)-benzo[d]imidazol-2-yl)thio)propanamide;
N-(2-chloro-4-methylphenyl)-2-((1-(4-methoxybenzyl)-benzo[d]imidazol-2-yl)thio)propanamide;
N-(2-chloro-4-methylphenyl)-2-((1-((6-methylpyridin-2-yl)methyl)-benzo[d]imidazol-2-yl)thio)propanamide;
N-(2-chloro-4-methylphenyl)-2-((1-(phenylsulfonyl)-benzo[d]imidazol-2-yl)thio)propanamide;
N-(2-chloro-4-methylphenyl)-2-((1-(cyclohexylsulfonyl)-benzo[d]imidazol-2-yl)thio)propanamide;
N-(2,4-dichlorophenyl)-2-((1-(4-methoxybenzyl)-benzo[d]imidazol-2-yl)thio)propanamide; and
N-(2-chloro-4-methylphenyl)-2-((1-(cyclohexanecarbonyl)-benzo[d]imidazol-2-yl)thio)propanamide or salt, prodrug, or ester thereof.

In certain embodiments, the disclosure relates to compounds of Formula IB,

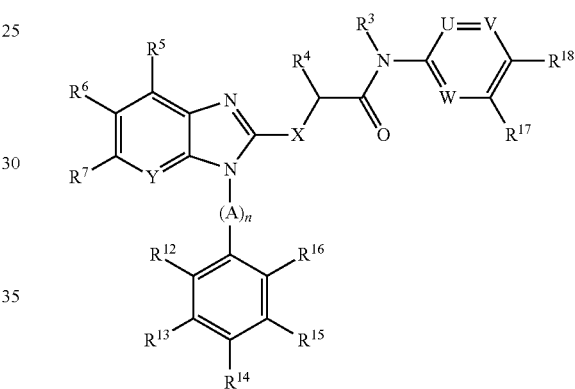

Formula IB or salts, prodrugs, or esters thereof wherein:
U is N or C—$R^{20}$;
V is N or C—$R^{19}$;
W is N or C—Z;
X is —S—, —SO—, or —$SO_2$—;
Y is N or C—$R^8$;
Z is hydrogen, alkyl, alkoxy, or halogen;
A is —$CR^{21}R^{22}$—, —SO—, —$SO_2$—, —C=O—, —C=ONH—, or a bond;
n is 0 or 1;
$R^3$ is hydrogen or alkyl, wherein $R^3$ is optionally substituted with one or more, the same or different $R^{11}$;
$R^4$ is hydrogen or alkyl, wherein $R^4$ is optionally substituted with one or more, the same or different $R^{11}$; $R^5$, $R^6$, $R^7$, $R^8$, $R^{12}$, $R^{13}$, $R^{15}$, and $R^{16}$, $R^{17}$, $R^{19}$, and $R^{20}$ are each individually and independently, hydrogen, halogen, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{14}$ is hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{14}$ is optionally substituted with one or more, the same or different, $R^{23}$;

$R^{18}$ is hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{18}$ is optionally substituted with one or more, the same or different, $R^{23}$;

$R^{21}$ and $R^{22}$ are each individually and independently, hydrogen or alkyl optionally substituted with one or more, the same or different, $R^{23}$; and $R^{23}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, at least one of $R^{18}$ or $R^{20}$ is not halogen.

In certain embodiments, at least one U or V or both is N.

In certain embodiments, at least one U or W or both is N.

In certain embodiments, the disclosure relates to compounds such as N-(3,5-dichloropyridin-2-yl)-2-((1-(4-fluorophenyl)-benzo[d]imidazol-2-yl)thio)propanamide;
N-(3,5-dichloropyridin-2-yl)-2-((1-(4-ethoxyphenyl)-benzo[d]imidazol-2-yl)thio)propanamide;
N-(3,5-dichloropyridin-2-yl)-2-((1-(4-hydroxyphenyl)-benzo[d]imidazol-2-yl)thio)propanamide;
N-(3-chloro-5-methylpyridin-2-yl)-2-((1-(4-ethoxyphenyl)-benzo[d]imidazol-2-yl)thio)propanamide;
N-(4,6-dimethylpyridin-2-yl)-2-((1-(4-ethoxyphenyl)-benzo[d]imidazol-2-yl)thio)propanamide;
N-(5,6-dimethyl-1,2,4-triazin-3-yl)-2-((1-(4-fluorophenyl)-benzo[d]imidazol-2-yl)thio)propanamide;
N-(3-chloro-5-methylpyridin-2-yl)-2-((1-(3-methoxyphenyl)-benzo[d]imidazol-2-yl)thio)propanamide;
N-(3-chloro-5-methylpyridin-2-yl)-2-((1-phenyl-benzo[d]imidazol-2-yl)thio)propanamide;
N-(3-chloro-5-methylpyridin-2-yl)-2-((1-(4-fluorophenyl)-benzo[d]imidazol-2-yl)thio)propanamide;
N-(3-chloro-5-methylpyridin-2-yl)-2-((1-(3,5-dimethoxyphenyl)-benzo[d]imidazol-2-yl)thio)propanamide;
N-(3-chloro-5-methylpyridin-2-yl)-2-((1-(m-tolyl)-benzo[d]imidazol-2-yl)thio)propanamide;
N-(3,5-dichloropyridin-2-yl)-2-((1-(4-methoxybenzyl)-benzo[d]imidazol-2-yl)thio)propanamide;
2-((1-benzyl-benzo[d]imidazol-2-yl)thio)-N-(3,5-dichloropyridin-2-yl)propanamide; and
N-(3-chloro-5-methylpyridin-2-yl)-2-((1-(4-methoxybenzyl)-benzo[d]imidazol-2-yl)thio)propanamide or salts, prodrugs or esters thereof.

In certain embodiments, the disclosure related to a compound of Formula IC in a composition with enantiomeric excess of greater than 51%, 55%, 60%, 65%, 80%, 90% or more,

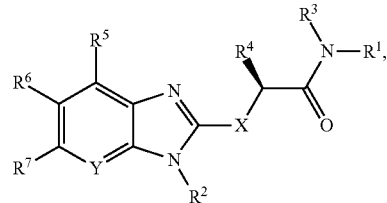

Formula IC or salts, prodrugs, or esters thereof wherein:

X is —S—, —SO—, or —SO$_2$—;

Y is N or C—$R^8$;

$R^1$ is an carbocyclyl, aryl, or heterocyclyl wherein $R^1$ is optionally substituted with one or more, the same or different, $R^9$;

$R^2$ is alkyl, formyl, alkylsulfonyl, arylsulfonyl, carbocyclyl, aryl, or heterocyclyl wherein $R^2$ is optionally substituted with one or more, the same or different, $R^{10}$;

$R^3$ is hydrogen or alkyl, wherein $R^3$ is optionally substituted with one or more, the same or different $R^{11}$;

$R^4$ is alkyl, wherein $R^4$ is optionally substituted with one or more, the same or different $R^{11}$;

$R^5$, $R^6$, $R^7$, and $R^8$ are each individually and independently, hydrogen, halogen, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl, wherein $R^9$ is optionally substituted with one or more, the same or different, $R^{11}$;

$R^{10}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is not 3,5-dichloro-pyrid-2-yl.

In certain embodiments, $R^1$ is a heterocyclyl selected from furyl, benzofuranyl, thiophenyl, benzothiophenyl, pyrrolyl, indolyl, isoindolyl, azaindolyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl or a heterocarbocyclyl, wherein the heterocyclyl is optionally substituted with one or more, the same or different, $R^9$.

In certain embodiments, $R^1$ is 2-chloro-4-methylphenyl.

In certain embodiments, $R^1$ is phenyl, ortho halogenated phenyl, aryl, thiazol-2-yl, isoxazol-3-yl, or pyrazol-5-yl, or heteroaryl.

In certain embodiments, $R^2$ is carbocyclyl, aryl, or heterocyclyl.

In certain embodiments, $R_2$ is a heterocyclyl.

In certain embodiments, $R^2$ is arylsulfonyl, heterocyclyl, or benzyl.

In certain embodiments, $R^2$ is not 4-methoxyphenyl, 4-methylphenyl, or 3-methylphenyl.

In certain embodiments, $R^3$ is hydrogen.

In certain embodiments, $R^4$ is methyl.

In certain embodiments, $R^5$, $R^6$, $R^7$, and $R^8$ are each individually and independently hydrogen or halogen.

In certain embodiments, Y is CH.

In certain embodiments the compound is (S)—N-(2-chloro-4-methylphenyl)-2-((1-(4-methoxyphenyl)-benzo[d]imidazol-2-yl)thio)propanamide (S)—N-(2-chloro-4-methylphenyl)-2-((1-(4-(2-morpholinoethyl)phenyl)-benzo[d]imidazol-2-yl)thio)propanamide;

(S)—N-(2-chloro-4-methylphenyl)-2-((1-(2-((4-methylpiperazin-1-yl)methyl)phenyl)-benzo[d]imidazol-2-yl)thio)propanamide; or (S)—N-(2-chloro-4-methylphenyl)-2-((1-(3-(2-morpholinoethyl)phenyl)-benzo[d]imidazol-2-yl)thio)propanamide or salts thereof.

In certain embodiments, the disclosure relates to compounds of Formula II:

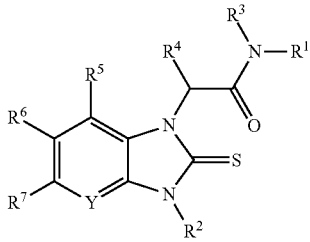

Formula II or salts, prodrugs, or esters thereof wherein:

Y is N or C—$R^8$;

$R^1$ is an carbocyclyl, aryl, or heterocyclyl wherein $R^1$ is optionally substituted with one or more, the same or different, $R^9$;

$R^2$ is alkyl, formyl, alkylsulfonyl, arylsulfonyl, carbocyclyl, aryl, or heterocyclyl wherein $R^2$ is optionally substituted with one or more, the same or different, $R^{10}$;

$R^3$ is hydrogen or alkyl, wherein $R^3$ is optionally substituted with one or more, the same or different $R^{11}$;

$R^4$ is hydrogen or alkyl, wherein $R^4$ is optionally substituted with one or more, the same or different $R^{11}$;

$R^5$, $R^6$, $R^7$, and $R^8$ are each individually and independently, hydrogen, halogen, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl, wherein $R^9$ is optionally substituted with one or more, the same or different, $R^{11}$;

$R^{10}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds such as N-(2-chloro-4-methylphenyl)-2-(3-(2-(morpholinomethyl)phenyl)-2-thioxo-2,3-dihydro-benzo[d]imidazol-1-yl)propanamide;

N-(2-chloro-4-methylphenyl)-2-(3-(2-((4-methylpiperazin-1-yl)methyl)phenyl)-2-thioxo-2,3-dihydro-benzo[d]imidazol-1-yl)propanamide; and N-(2-chloro-4-methylphenyl)-2-(3-(2-(hydroxymethyl)phenyl)-2-thioxo-2,3-dihydro-benzo[d]imidazol-1-yl)propanamide or salts, prodrugs, or esters thereof.

In certain embodiments, the disclosure relates to a compound of Formula X,

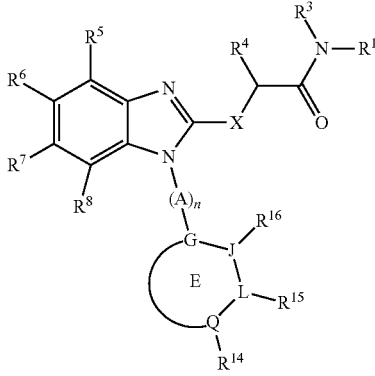

Formula X or salts, prodrugs, or esters thereof wherein:

A is —$CH_2$—, —SO—, —$SO_2$—, —C=O—, —C=ONH—, or a bond to G;

n is 0, 1, or 2;

E, together with the atoms G, J, L, and Q, is a five or six membered, carbocyclyl, aryl, or heterocyclyl;

G, J, L, and Q are each independently N, C, or CH;

X is —S—, —SO—, or —SO$_2$—;

$R^1$ is an carbocyclyl, aryl, or heterocyclyl wherein $R^1$ is optionally substituted with one or more, the same or different, $R^{11}$;

$R^3$ is hydrogen or alkyl, wherein $R^3$ is optionally substituted with one or more, the same or different $R^{11}$;

$R^4$ is hydrogen or alkyl, wherein $R^4$ is optionally substituted with one or more, the same or different $R^{11}$;

$R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; $R^{14}$, $R^{15}$, and $R^{16}$ are each independently hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein each $R^{14}$, $R^{15}$, and $R^{16}$ is optionally substituted with one or more, the same or different, $R^{23}$;

$R^5$, $R^6$, $R^7$, and $R^8$ are each independently hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein each $R^5$, $R^6$, $R^7$, and $R^8$ is optionally substituted with one or more the same or different, $R^{23}$; and $R^{23}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, at least one of $R^{14}$, $R^{15}$, and $R^{16}$ is —(CH$_2$)$_m$—$R^{24}$, wherein m is 0, 1, or 2, otherwise $R^{14}$, $R^{15}$, and $R^{16}$ are each independently hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein each $R^{14}$, $R^{15}$, and $R^{16}$ is optionally substituted with one or more, the same or different, $R^{23}$;

$R^{24}$ is a alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{24}$ is optionally substituted with one or more, the same or different, $R^{25}$;

$R^{25}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{25}$ is optionally substituted with one or more, the same or different, $R^{26}$; and $R^{26}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is S or SO.

In certain embodiments, $R^1$ is phenyl optionally substituted with a halogen or alkyl;

In certain embodiments, $R^1$ is 2-chloro-4-methylphenyl;

In certain embodiments, $R^3$ is hydrogen.

In certain embodiments, $R^4$ is methyl.

In certain embodiments $R^{24}$ is a heterocyclyl such as one selected from aziridinyl, oxaziridinyl, azetidinyl, diazetidenyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, or thiomorpholine optionally substituted with one or more, the same or different, $R^{25}$.

In certain embodiments, $R^{24}$ is morpholinyl or piperazinyl optionally substituted with one or more $R^{25}$.

In certain embodiments, $R^{25}$ is alkyl.

In certain embodiments, E is a five or six membered heterocyclyl.

In certain embodiments, at least one G, J, L, and Q is N.

In certain embodiments, the disclosure relates to compound of Formula XA,

Formula XA

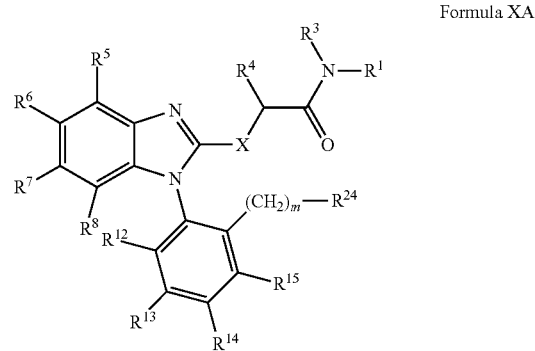

or salts, prodrugs, or esters thereof wherein:

X is —S—, —SO—, or —SO$_2$—;

m is 1 or 2;

$R^1$ is an carbocyclyl, aryl, or heterocyclyl wherein $R^1$ is optionally substituted with one or more, the same or different, $R^{11}$;

$R^3$ is hydrogen or alkyl, wherein $R^3$ is optionally substituted with one or more, the same or different $R^{11}$;

$R^4$ is hydrogen or alkyl, wherein $R^4$ is optionally substituted with one or more, the same or different $R^{11}$;

$R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; $R^5$, $R^6$, $R^7$, $R^8$, $R^{12}$, $R^{13}$, $R^{14}$, and $R^{15}$ are each independently hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein each $R^5$, $R^6$, $R^7$, $R^8$, $R^{12}$, $R^{13}$, $R^{14}$, and $R^{15}$ is optionally substituted with one or more, the same or different, $R^{23}$;

$R^{23}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{24}$ is a alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{24}$ is optionally substituted with one or more, the same or different, $R^{25}$;

$R^{25}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{25}$ is optionally substituted with one or more, the same or different, $R^{26}$; and $R^{26}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is S or SO.

In certain embodiments, $R^1$ is phenyl optionally substituted with a halogen or alkyl;

In certain embodiments, $R^1$ is 2-chloro-4-methylphenyl;

In certain embodiments, $R^3$ is hydrogen.

In certain embodiments, $R^4$ is methyl.

In certain embodiments, $R^{24}$ is a heterocyclyl such as one selected from aziridinyl, oxaziridinyl, azetidinyl, diazetidenyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, or thiomorpholine optionally substituted with one or more, the same or different, $R^{25}$.

In certain embodiments, $R^{24}$ is piperazinyl optionally substituted with one or more $R^{25}$.

In certain embodiments, $R^{25}$ is alkyl.

In certain embodiments, the disclosure relates to compound of Formula XB,

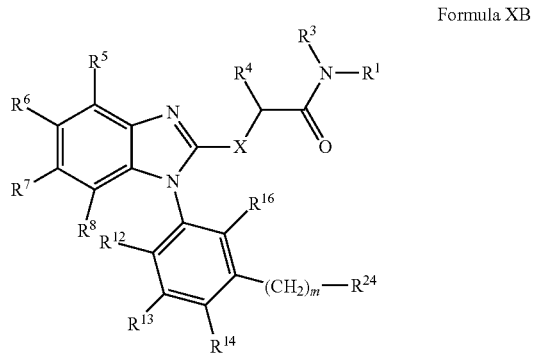

Formula XB or salts, prodrugs, or esters thereof wherein:
X is —S—, —SO—, or —SO$_2$—;
m is 1 or 2;
$R^1$ is an carbocyclyl, aryl, or heterocyclyl wherein $R^1$ is optionally substituted with one or more, the same or different, $R^{11}$;

$R^3$ is hydrogen or alkyl, wherein $R^3$ is optionally substituted with one or more, the same or different $R^{11}$;

$R^4$ is hydrogen or alkyl, wherein $R^4$ is optionally substituted with one or more, the same or different $R^{11}$;

$R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; $R^5$, $R^6$, $R^7$, $R^8$, $R^{12}$, $R^{13}$, $R^{14}$, and $R^{16}$ are each independently hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein each $R^5$, $R^6$, $R^7$, $R^8$, $R^{12}$, $R^{13}$, $R^{14}$, and $R^{16}$ is optionally substituted with one or more, the same or different, $R^{23}$;

$R^{23}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{24}$ is a alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{24}$ is optionally substituted with one or more, the same or different, $R^{25}$;

$R^{25}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{25}$ is optionally substituted with one or more, the same or different, $R^{26}$; and $R^{26}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is S or SO.

In certain embodiments, $R^1$ is phenyl optionally substituted with a halogen or alkyl;

In certain embodiments, $R^1$ is 2-chloro-4-methylphenyl;

In certain embodiments, $R^3$ is hydrogen.

In certain embodiments, $R^4$ is methyl.

In certain embodiments, $R^{24}$ is selected from aziridinyl, oxaziridinyl, azetidinyl, diazetidenyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, or thiomorpholine optionally substituted with one or more, the same or different, $R^{25}$.

In certain embodiments, the disclosure relates to compound of Formula XC,

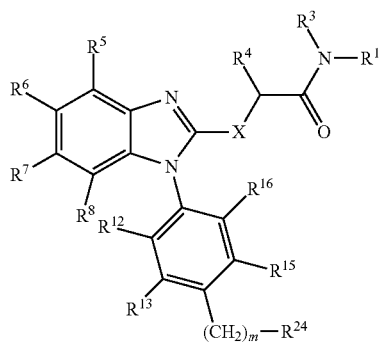

Formula XC or salts, prodrugs, or esters thereof wherein:

X is —S—, —SO—, or —SO$_2$—;

m is 1 or 2;

$R^1$ is an carbocyclyl, aryl, or heterocyclyl wherein $R^1$ is optionally substituted with one or more, the same or different, $R^{11}$;

$R^3$ is hydrogen or alkyl, wherein $R^3$ is optionally substituted with one or more, the same or different $R^{11}$;

$R^4$ is hydrogen or alkyl, wherein $R^4$ is optionally substituted with one or more, the same or different $R^{11}$;

$R^{11}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^5$, $R^6$, $R^7$, $R^8$, $R^{12}$, $R^{13}$, $R^{15}$, and $R^{16}$ are each independently hydrogen, alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein each $R^5$, $R^6$, $R^7$, $R^8$, $R^{12}$, $R^{13}$, $R^{15}$, and $R^{16}$ is optionally substituted with one or more, the same or different, $R^{23}$;

$R^{23}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{24}$ is a alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{24}$ is optionally substituted with one or more, the same or different, $R^{25}$;

$R^{25}$ is alkyl, halogen, cyano, hydroxy, amino, mercapto, formyl, carboxy, carbamoyl, alkoxy, alkylthio, alkylamino, aminoalkyl, (alkyl)$_2$-amino, alkylsulfinyl, alkylsulfonyl, arylsulfonyl, carbocyclyl, aryl, or heterocyclyl wherein $R^{25}$ is optionally substituted with one or more, the same or different, $R^{26}$; and $R^{26}$ is individually and independently, halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is S or SO.

In certain embodiments, $R^1$ is phenyl optionally substituted with a halogen or alkyl;

In certain embodiments, $R^1$ is 2-chloro-4-methylphenyl;

In certain embodiments, $R^3$ is hydrogen.

In certain embodiments, $R^4$ is methyl.

In certain embodiments, $R^{24}$ is selected from aziridinyl, oxaziridinyl, azetidinyl, diazetidenyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, or thiomorpholine optionally substituted with one or more, the same or different, $R^{25}$.

Synthetic Preparation

Figure 9A:
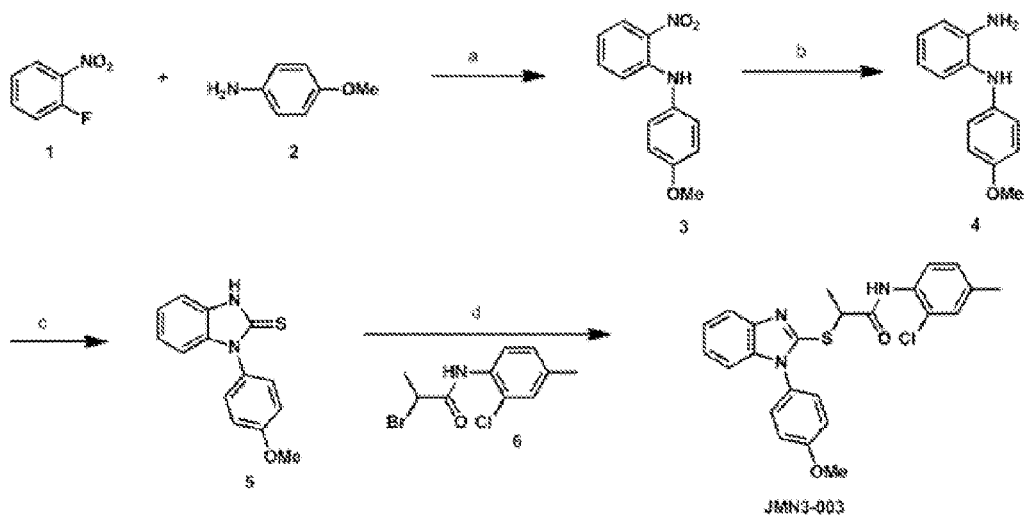
FIG. 9A illustrates general strategies for preparing compounds disclosed herein, e.g., JMN3-003. a) $K_2CO_3$, 160 degree C. or $Et_3N$, 150 degree microwave. b) $H_2$, Pd/C, ethanol, 40 psi. c) 1,1'-thiocarbonyldiimidazole, $CH_2Cl_2$. D) KO$^t$Bu, ethanol.
Figures 9B, 10:
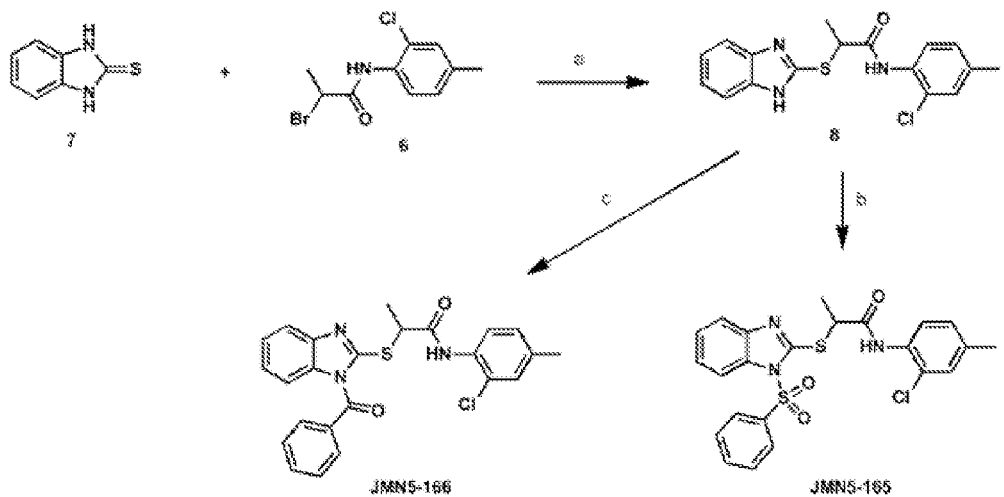
FIG. 9B illustrates scheme for preparing compound disclosed herein. a) NaH, THF. b) benzenesulfonyl chloride, i-Pr$_2$NEt, $CH_2Cl_2$. c) benzoyl chloride, i-Pr$_2$NEt, $CH_2Cl_2$.
FIG. 10 shows a table on (EC$_{50}$) (CC$_{50}$, determined on Vero-Slam cells) JMN3-003 against a selection of clinically relevant para- and orthomyxovirus family members in comparison with active concentrations of AS-136A, a previously characterized, MeV-specific inhibitor of the viral RdRp complex. See Yoon et al., Antimicrob Agents Chemother., 2009, 53(9):3860-3870. a) For influenza virus titration, genome copy numbers of released progeny particles were quantified by TaqMan RT-PCR. b) Titered through plaque assaying. c) Titered by TCID50 titration. d) Highest concentration assessed 75 µM. e 95% confidence interval. ND: not determined.

The preparation of certain compounds described herein are provided for in the experimental section and outlined in FIGS. 9A and 9B. By making appropriate substitutions of commercially available starting materials a variety of alternatives are generated according to the schemes provided below. $W^1$, $W^2$, or $W^3$ is a leaving group such as a halogen or tosyl group.

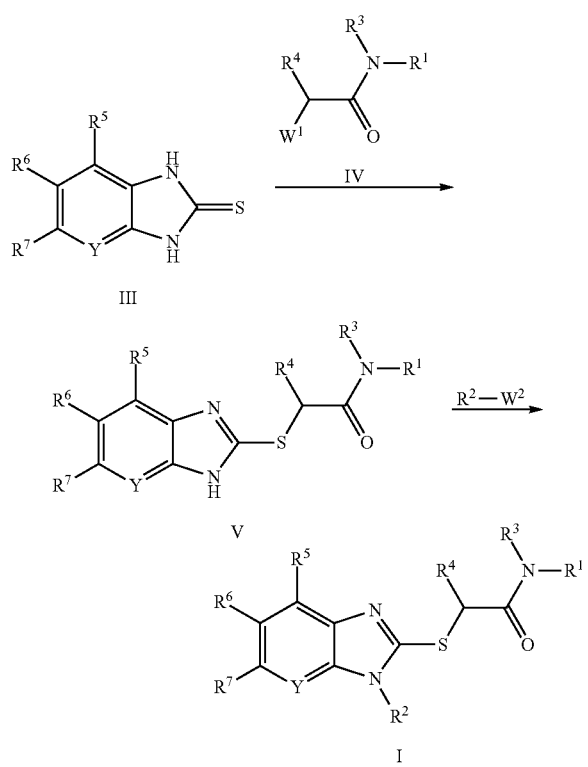

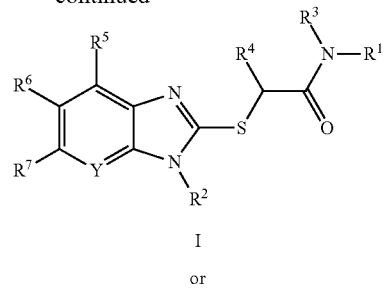

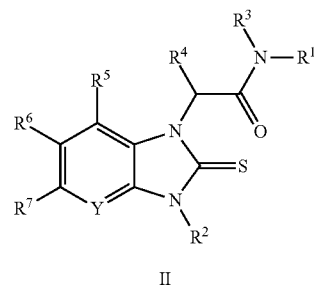

In certain embodiments, the disclosure relates to methods of preparing compounds of formula I as described herein, by mixing a compound of formula V and $R^2$—$W^2$ wherein $W^2$ is a leaving group such as a halogen, or tosyl group, under conditions such that a compound of formula I is formed.

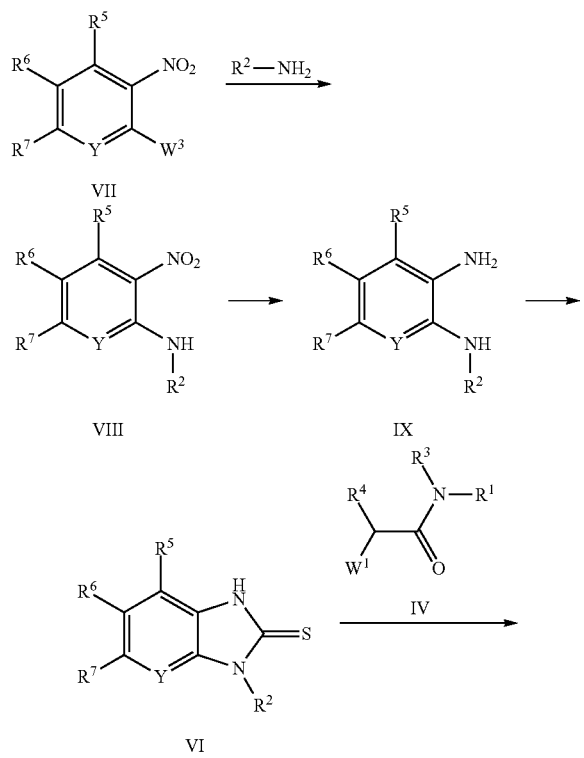

In certain embodiments, the disclosure relates to methods of preparing compounds of formula I or formula II as described herein, by mixing a compound of formula IV and a compound of formula VI under conditions such that a compound of formula I or formula II is formed.

Combination Therapies

In certain embodiments, the pharmaceutical composition comprising a compound disclosed herein is administered in combination with one or more second antiviral agent such as is abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, and/or zidovudine.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly(acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethylcellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

EXPERIMENTAL

Example 1

Inhibitors of Myxovirus RNA-Dependent RNA-Polymerases

The primary screening agent, serving as the myxovirus representative, was the wild type MeV isolate MVi/Alaska.USA/16.00 (MeV-Alaska) was chosen based on its ease of growth and readily quantifiable cytopathic effect in an automated system. In search of candidates with a host-directed antiviral profile, three distinct features of desirable compounds were identified as: a) potent inhibition of virus replication at the screening concentration (3.3 µM); b) a primary screening score, representative of the selectivity index ($CC50/EC_{50}$), close to the cut-off value for hit candidates due to some anticipated host-cell interference ($\geq 1.9$); and c) a broadened viral target spectrum in counterscreening assays that extends to other pathogens of the myxovirus families.

A chemical scaffold with broad anti-myxovirus activity was identified. When inhibition of paramyxovirus family members was assessed, certain compounds efficiently blocked the closely related canine distemper virus (CDV) and the more distantly related human parainfluenzavirus type 3 (HPIV3) in addition to MeV-Alaska, while leaving cell metabolic activity essentially unaffected. Analogs that matched the target criteria were subjected to further characterization and developmental efforts. A summary of compounds tested is provided in tables 1-5 below:

where R is as defined in table 1 below.

TABLE 1

| entry | R | EC$_{50}$ |
|---|---|---|
| 1 | 3,5-dichloropyridin-2-yl | 0.3 |
| 2 | 2,5-dibromophenyl | 1.7 |
| 3 | 3-chloro-5-(trifluoromethyl)pyridin-2-yl | 0.4 |
| 4 | 3,6-dichloropyridin-2-yl | 0.3 |
| 5 | 3-chloro-5-methylpyridin-2-yl | 0.04 |
| 6 | 5,6-dimethyl-1,2,4-triazin-3-yl | 16.6 |
| 7 | 4-chloro-6-methylpyrimidin-2-yl | >150 |
| 8 | 5-bromopyrimidin-2-yl | 4.1 |
| 9 | cyclohexyl | >75 |
| 10 | 3-methylphenyl | 0.3 |
| 11 | 4-methylpyrimidin-2-yl | 0.6 |
| 12 | 2,4-dichlorophenyl | 0.4 |
| 13 | 3,5-dimethoxyphenyl | >75 |
| 14 | 3-chlorophenyl | 0.5 |
| 15 | 2-methylphenyl | 1.14 |
| 16 | 3-amino-4-methylphenyl | 2.3 |
| 17 | 4-acetamido-3-methylphenyl | >9.3 |
| 18 | 1,3-dimethyl-1H-pyrazol-5-yl | 0.9 |
| 19 | 3-methylisoxazol-5-yl | 0.58 |

TABLE 1-continued
| entry | R | EC$_{50}$ |
|---|---|---|
| 19 | 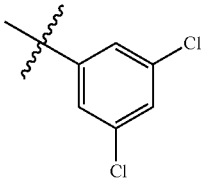 [SMILES: *c1cc(Cl)cc(Cl)c1] | >75 |
| 20 | 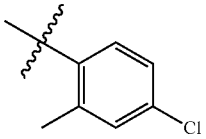 [SMILES: *c1ccc(Cl)cc1C] | 1.4 |
| 21 | 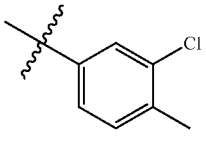 [SMILES: *c1ccc(C)c(Cl)c1] | 0.4 |
| 22 | 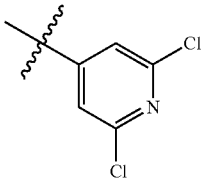 [SMILES: *c1cc(Cl)nc(Cl)c1] | >75 |
| 23 | 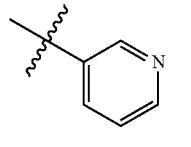 [SMILES: *c1cccnc1] | 8.4 |
| 24 | 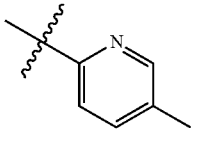 [SMILES: *c1ccc(C)cn1] | 0.5 |
| 25 | 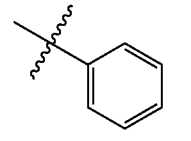 [SMILES: *c1ccccc1] | 0.9 |
| 26 | 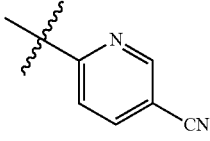 [SMILES: *c1ccc(C#N)cn1] | >75 |
| 27 | 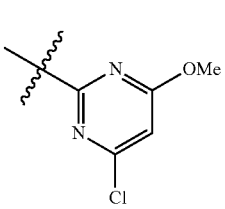 [SMILES: *c1nc(Cl)cc(OC)n1] | >75 |
TABLE 1-continued
| entry | R | EC$_{50}$ |
|---|---|---|
| 28 | 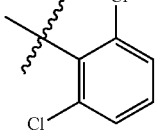 | 2.0 |
| 29 | 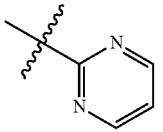 [SMILES: *c1ncccn1] | 2.0 |
| 30 | 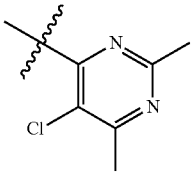 [SMILES: *c1nc(C)nc(C)c1Cl] | >75 |
| 31 | 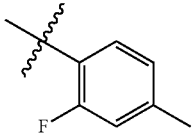 [SMILES: *c1ccc(C)cc1F] | 0.2 |
| 32 | 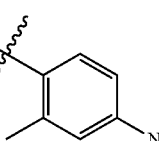 | >9.3 |
| 33 | 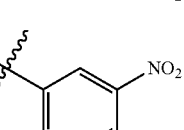 | 4.6 |
| 34 | 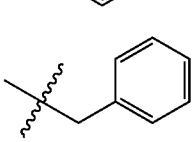 | >9.3 |
| 35 | 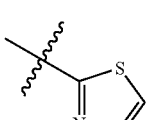 | 3.6 |
| 36 | 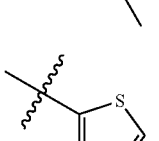 | 4.0 |
| 37 | | |
| 38 | 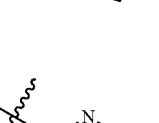 | 11.5 |

TABLE 1-continued

| entry | R | EC$_{50}$ |
|---|---|---|
| 39 | 2-chloro-6-methylphenyl | 3.9 |
| 40 | 4-chloro-3-methylphenyl | 6.7 |
| 41 | 3,5-dibromo-2,6-dimethylpyridin-4-yl | 0.5 |
| 42 | pyridin-4-yl | >75 |
| 43 | 3,5-dichloro-2,6-dimethylpyridin-4-yl | 0.3 |
| 44 | 4,6-dichloropyrimidin-2-yl | >75 |
| 45 | 2,4-dimethylphenyl | 1.1 |
| 46 | 2,5-dichlorophenyl | 0.5 |
| 47 | 4-fluorophenyl | >10 |
| 48 | 3,4-dichlorophenyl | 7.3 |
| 49 | 4-methylphenyl | 0.7 |
| 50 | 2-chlorophenyl | 0.14 |
| 51 | 3-aminophenyl | 7.0 |
| 52 | 4-amino-2-methylphenyl | >9.3 |
| 53 | 5-methylthiazol-2-yl | >150 |
| 54 | 4,5-dimethylthiazol-2-yl | 2.5 |
| 55 | 5-methylisoxazol-3-yl | 0.49 | where R is as defined in table 2 below.

TABLE 2

| entry | R | EC$_{50}$ |
|---|---|---|
| 56 | 4-(morpholinomethyl)phenyl | 0.32 |
| 57 | 4-(cyanomethoxy)phenyl | 0.7 |
| 58 | 4-(2-hydroxyethoxy)phenyl | 4.6 |
| 59 | 4-((2-(dimethylamino)ethyl)amino)phenyl | 4.2 |
| 60 | 4-((2-(dimethylamino)ethyl)(methyl)amino)phenyl | 2.9 |
| 61 | 4-(2-acetamidoethoxy)phenyl | >10 |
| 62 | 4-(2-oxoethyl)phenyl | 8.5 |
| 63 | 4-((4-methylpiperazin-1-yl)methyl)phenyl | 4.9 |
| 64 | 4-(2-hydroxyethyl)phenyl | 2.5 |
| 65 | 3-((4-methylpiperazin-1-yl)methyl)phenyl | 1.3 |
| 66 | 4-(2-(methylamino)ethyl)phenyl | 8.7 |
| 67 | 2-((4-methylpiperazin-1-yl)methyl)phenyl | 0.18 |

TABLE 2-continued

| entry | R | EC$_{50}$ |
|---|---|---|
| 68 | 4-(carboxymethoxy)phenyl | >9.3 |
| 69 | 4-(2-methoxy-2-oxoethoxy)phenyl | >9.3 |
| 70 | 4-(4-methylpiperazin-1-yl)phenyl | 2.0 |
| 71 | 3-methoxyphenyl | 0.6 |
| 72 | phenyl | 0.09 |
| 73 | 4-ethoxyphenyl | 0.05 |
| 74 | benzyl | 0.5 |
| 75 | 3-methylphenyl | 0.1 |
| 76 | 4-hydroxyphenyl | 3.8 |
| 77 | 4-(dimethylamino)phenyl | 0.29 |
| 78 | 4-aminophenyl | 1.33 |
| 79 | 2-(morpholinomethyl)phenyl | 0.30 |

TABLE 2-continued

| entry | R | EC$_{50}$ |
|---|---|---|
| 80 | 3-(hydroxymethyl)phenyl | 0.7 |
| 81 | 4-(hydroxymethyl)phenyl | 3.91 |
| 82 | 3-carboxyphenyl | >75 |
| 83 | 3-(morpholinomethyl)phenyl | 0.27 |
| 84 | 4-morpholinophenyl | 0.3 |
| 85 | 4-methoxybenzyl | 0.4 |
| 86 | 4-methoxyphenyl | 0.17 |
| 87 | 3,5-dimethoxyphenyl | 0.4 |
| 88 | cyclohexyl | 0.29 |
| 89 | cyclohexylsulfonyl | 0.61 |
| 90 | phenylsulfonyl | 0.04 |
| 91 | benzoyl | >9.3 |
| 92 | piperidin-4-yl | >75 |
| 93 | 1-Boc-piperidin-4-yl | 0.6 |
| 94 | 1-methylpiperidin-4-yl | 1.5 |
| 95 | 4-azidophenyl | 0.31 |
| 96 | 2-(hydroxymethyl)phenyl | 0.8 |
| 97 | 4-carboxyphenyl | >75 |
| 98 | 4-((dimethylamino)methyl)phenyl | 1.4 |
| 99 | 4-(methoxycarbonyl)phenyl | 1.1 |

TABLE 2-continued

| entry | R | EC$_{50}$ |
|---|---|---|
| 100 | (2-methyl-pyridin-6-yl)methyl | >9.3 |

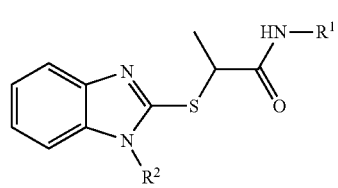

where R$_1$ and R$_2$ are as defined in table 3 below.

TABLE 3

| entry | R$^2$ | R$^1$ | EC$_{50}$ |
|---|---|---|---|
| 101 | 4-F-C$_6$H$_4$ | 3,5-diCl-pyridin-2-yl | 0.3 |
| 102 | 4-OEt-C$_6$H$_4$ | 3,5-diCl-pyridin-2-yl | 0.2 |
| 103 | 4-OH-C$_6$H$_4$ | 3,5-diCl-pyridin-2-yl | 7.7 |
| 104 | 4-OMe-C$_6$H$_4$-CH$_2$ | 3,5-diCl-pyridin-2-yl | 0.06 |
| 105 | CH$_3$SO$_2$-CH$_2$ | 3,5-diCl-pyridin-2-yl | >75 |
| 106 | 4-F-C$_6$H$_4$ | 5,6-dimethyl-1,2,4-triazin-3-yl | 23 |
| 107 | 4-OMe-C$_6$H$_4$-CH$_2$ | 3-Cl-5-methyl-pyridin-2-yl | 0.8 |

TABLE 3-continued

| entry | R$^2$ | R$^1$ | EC$_{50}$ |
|---|---|---|---|
| 108 | 3-OMe-C$_6$H$_4$ | 3-Cl-5-methyl-pyridin-2-yl | 0.4 |
| 109 | C$_6$H$_5$ | 3-Cl-5-methyl-pyridin-2-yl | 0.13 |
| 110 | 4-OEt-C$_6$H$_4$ | 2-methyl-4-NO$_2$-C$_6$H$_3$ | >9.3 |
| 111 | C$_6$H$_5$-CH$_2$ | 3,5-diCl-pyridin-2-yl | 4.9 |
| 112 | 4-OEt-C$_6$H$_4$ | 3-Cl-5-methyl-pyridin-2-yl | — |
| 113 | t-Bu (CH$_3$)$_3$C | 3,5-diCl-pyridin-2-yl | >10 |
| 114 | CH$_2$CO$_2$Me | 3,5-diCl-pyridin-2-yl | >10 |
| 115 | 4-OEt-C$_6$H$_4$ | 4,6-dimethyl-pyridin-2-yl | 1.5 |
| 116 | 4-F-C$_6$H$_4$ | 3-Cl-5-methyl-pyridin-2-yl | 0.8 |
| 117 | 4-OMe-C$_6$H$_4$-CH$_2$ | 2,4-diCl-C$_6$H$_3$ | 1.7 |

TABLE 3-continued

| entry | R² | R¹ | EC₅₀ |
|---|---|---|---|
| 118 | 3,5-dimethoxyphenyl | 3-chloro-5-methyl-pyridin-2-yl | 0.8 |
| 119 | 3-methylphenyl | 3-chloro-5-methyl-pyridin-2-yl | 0.09 |
| 120 | H | 3,5-dichloropyridin-2-yl | >75 |

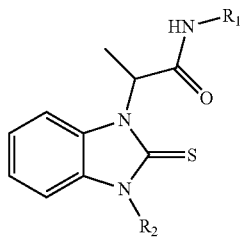

where R₁ and R₂ are as defined in table 4 below.

TABLE 4

| entry | R₁ | R₂ | EC₅₀ |
|---|---|---|---|
| 121 | 2-chloro-4-methylphenyl | 2-(morpholinomethyl)phenyl | 0.47 |
| 122 | 2-chloro-4-methylphenyl | 2-((4-methylpiperazin-1-yl)methyl)phenyl | 0.2 |
| 123 | 2-chloro-4-methylphenyl | 2-(hydroxymethyl)phenyl | 2.56 |

TABLE 5

| entry | structure | EC₅₀ |
|---|---|---|
| 124 | 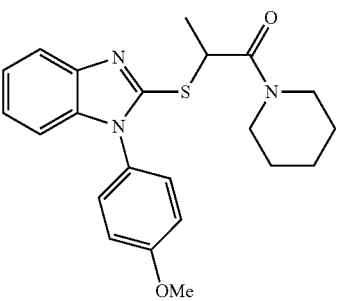 [SMILES: COc1ccc(-n2c(SC(C)C(=O)N3CCCCC3)nc3ccccc32)cc1] | >75 |
| 125 | 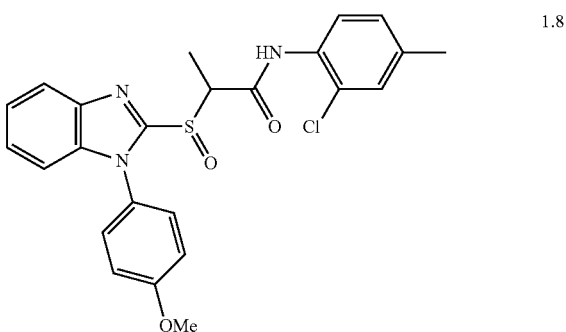 | 1.8 |

TABLE 5-continued

| entry | structure | EC$_{50}$ |
|---|---|---|
| 126 | EtOOC-benzimidazole-S-CH(Me)-C(O)NH-(2-Cl-4-Me-phenyl) | >75 |
| 127 | 1-(4-methoxybenzyl)benzimidazol-2-yl-NH-CH(Me)-C(O)NH-(2-Cl-4-Me-phenyl) | >75 |
| 128 | 4,5-diphenyl-1-(4-fluorobenzyl)imidazol-2-yl-S-CH(Me)-C(O)NH-(2-Cl-4-Me-phenyl) | >75 |
| 129 | 5,6-dimethyl-1-(4-fluorobenzyl)benzimidazol-2-yl-S-CH(Me)-C(O)NH-(2-Cl-4-Me-phenyl) | 2.1 |
| 130 | benzothiazol-2-yl-S-CH(Me)-C(O)NH-(2-Cl-4-Me-phenyl) | >75 |
| 131 | 1-(4-methoxyphenyl)benzimidazol-2-yl-S-CH(Et)-C(O)NH-(3,5-dichloropyridin-2-yl) | 12.2 |

TABLE 5-continued

| entry | structure | EC$_{50}$ |
|---|---|---|
| 132 | 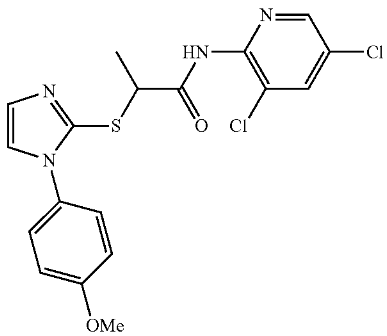 [SMILES: COc1ccc(-n2ccnc2SC(C)C(=O)Nc2ncc(Cl)cc2Cl)cc1] | >75 |
| 133 | 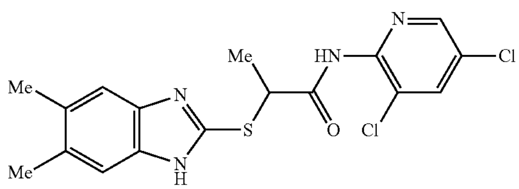 [SMILES: Cc1cc2nc(SC(C)C(=O)Nc3ncc(Cl)cc3Cl)[nH]c2cc1C] | >75 |
| 134 | 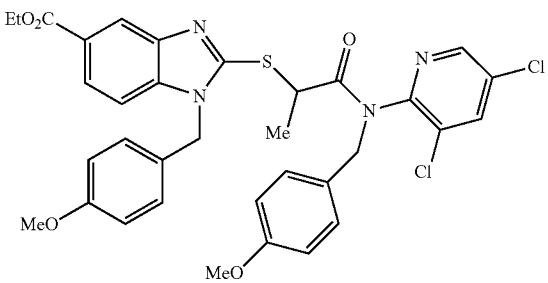 [SMILES: CCOC(=O)c1ccc2c(c1)nc(SC(C)C(=O)N(Cc1ccc(OC)cc1)c1ncc(Cl)cc1Cl)n2Cc1ccc(OC)cc1] | >75 |
| 135 | 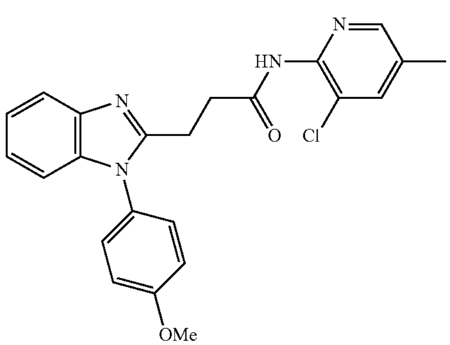 [SMILES: COc1ccc(-n2c(CCC(=O)Nc3ncc(C)cc3Cl)nc3ccccc32)cc1] | >75 |
| 136 | 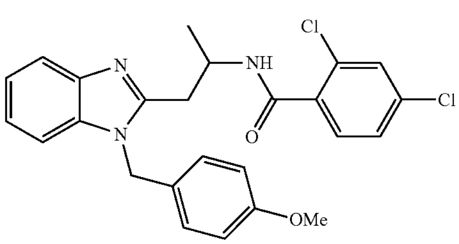 [SMILES: COc1ccc(Cn2c(CC(C)NC(=O)c3ccc(Cl)cc3Cl)nc3ccccc32)cc1] | >75 |

TABLE 5-continued

| entry | structure | EC$_{50}$ |
|---|---|---|
| 137 | 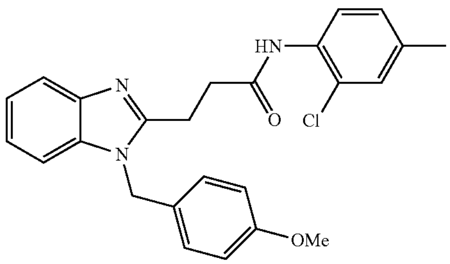 [SMILES: COc1ccc(Cn2c(CCC(=O)Nc3ccc(C)cc3Cl)nc3ccccc32)cc1] | >75 |
| 138 | 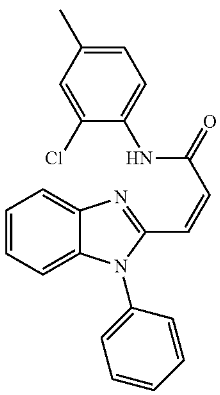 [SMILES: Cc1ccc(NC(=O)/C=C\c2nc3ccccc3n2-c2ccccc2)c(Cl)c1] | >50 |
| 139 | 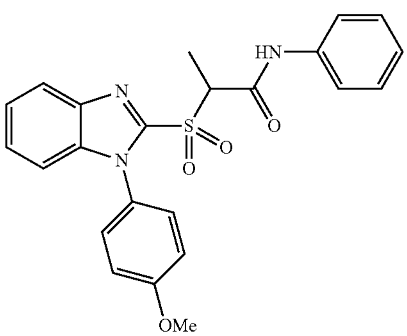 [SMILES: COc1ccc(-n2c(S(=O)(=O)C(C)C(=O)Nc3ccccc3)nc3ccccc32)cc1] | >75 |
| 140 | 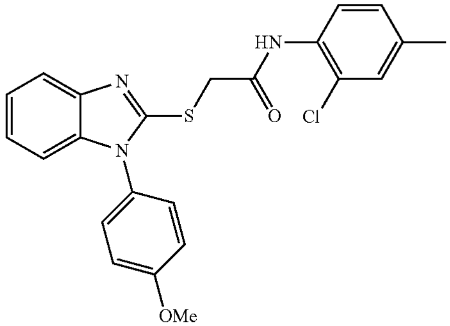 [SMILES: COc1ccc(-n2c(SCC(=O)Nc3ccc(C)cc3Cl)nc3ccccc32)cc1] | 1.05 |

TABLE 5-continued

| entry | structure | EC$_{50}$ |
|---|---|---|
| 141 | 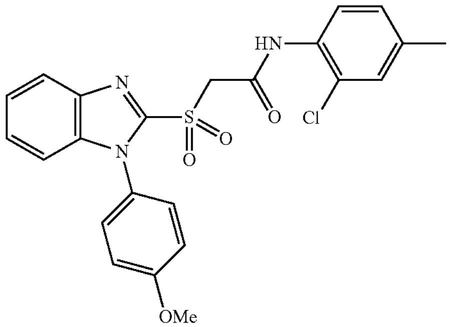 [SMILES: COc1ccc(-n2c(S(=O)(=O)CC(=O)Nc3ccc(C)cc3Cl)nc3ccccc32)cc1] | >75 |
| 142 | 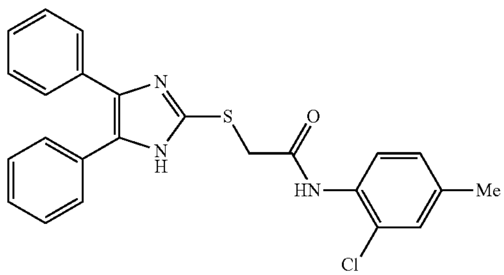 [SMILES: Cc1ccc(NC(=O)CSc2nc(-c3ccccc3)c(-c3ccccc3)[nH]2)c(Cl)c1] | >75 |
| 143 | 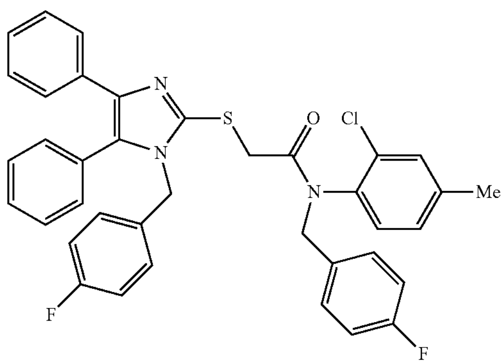 [SMILES: Cc1ccc(N(Cc2ccc(F)cc2)C(=O)CSc2nc(-c3ccccc3)c(-c3ccccc3)n2Cc2ccc(F)cc2)c(Cl)c1] | >75 |
| 144 | 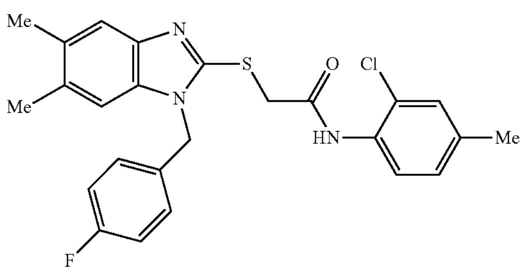 [SMILES: Cc1ccc(NC(=O)CSc2nc3cc(C)c(C)cc3n2Cc2ccc(F)cc2)c(Cl)c1] | >75 |
| 145 | 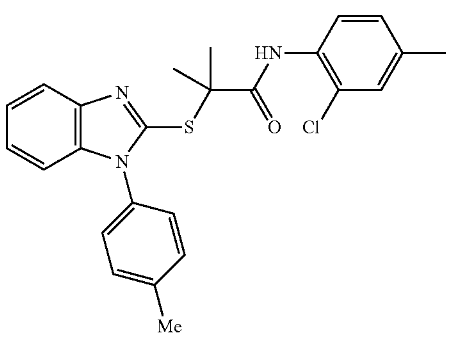 [SMILES: Cc1ccc(-n2c(SC(C)(C)C(=O)Nc3ccc(C)cc3Cl)nc3ccccc32)cc1] | >75 |

TABLE 5-continued

| entry | structure | EC$_{50}$ |
|---|---|---|
| 146 | 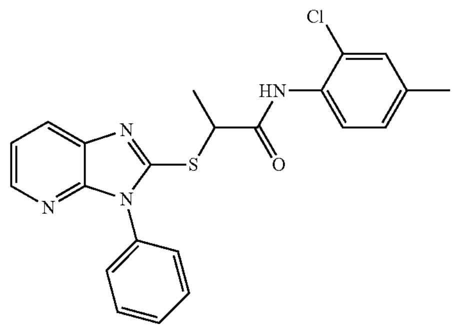 [SMILES: Cc1ccc(NC(=O)C(C)Sc2nc3cccnc3n2-c2ccccc2)c(Cl)c1] | 1.2 |
| 147 | 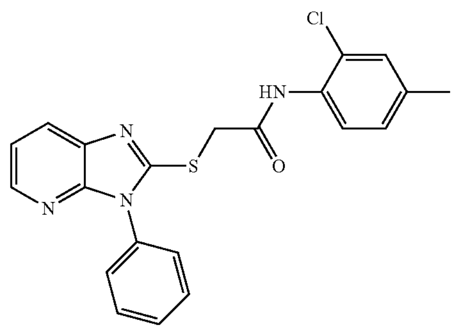 [SMILES: Cc1ccc(NC(=O)CSc2nc3cccnc3n2-c2ccccc2)c(Cl)c1] | 16 |
| 148 | 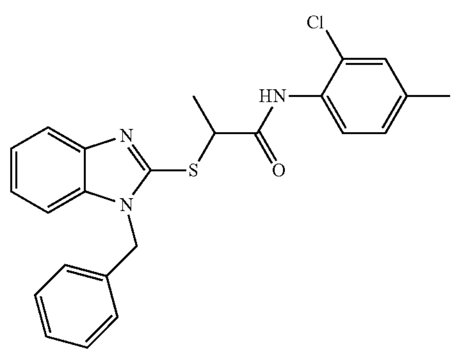 [SMILES: Cc1ccc(NC(=O)C(C)Sc2nc3ccccc3n2Cc2ccccc2)c(Cl)c1] | >75 |
| 149 | 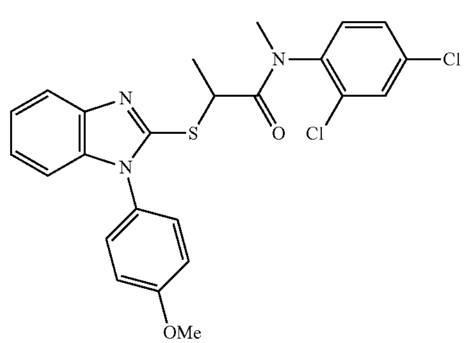 [SMILES: COc1ccc(-n2c(SC(C)C(=O)N(C)c3ccc(Cl)cc3Cl)nc3ccccc32)cc1] | >75 |

TABLE 5-continued

| entry | structure | EC$_{50}$ |
|---|---|---|
| 150 | 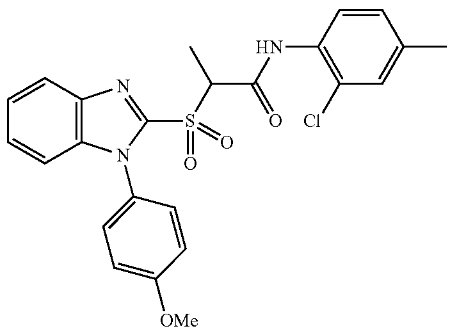 [SMILES: COc1ccc(-n2c(S(=O)(=O)C(C)C(=O)Nc3ccc(C)cc3Cl)nc3ccccc32)cc1] | >150 |
| 151 | 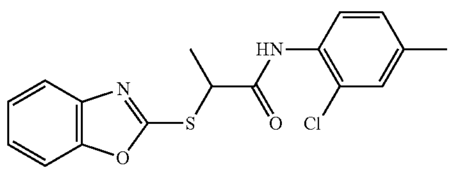 [SMILES: Cc1ccc(NC(=O)C(C)Sc2nc3ccccc3o2)c(Cl)c1] | >75 |
| 152 | 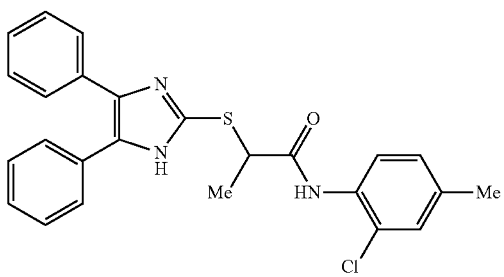 [SMILES: Cc1ccc(NC(=O)C(C)Sc2nc(-c3ccccc3)c(-c3ccccc3)[nH]2)c(Cl)c1] | >75 |
| 153 | 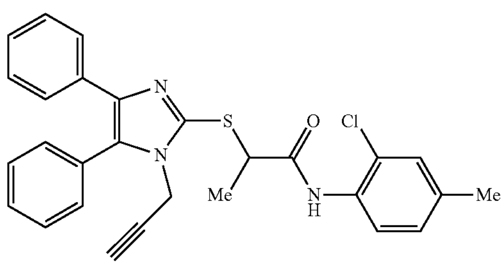 [SMILES: C#CCn1c(SC(C)C(=O)Nc2ccc(C)cc2Cl)nc(-c2ccccc2)c1-c1ccccc1] | >75 |
| 154 | 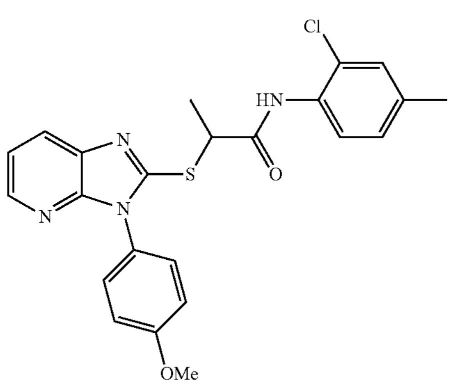 [SMILES: COc1ccc(-n2c(SC(C)C(=O)Nc3ccc(C)cc3Cl)nc3cccnc32)cc1] | 1.6 |

TABLE 5-continued

| entry | structure | EC$_{50}$ |
|---|---|---|
| 155 | 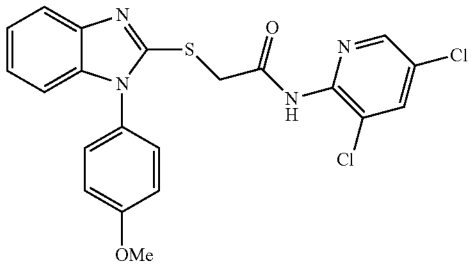 [SMILES: COc1ccc(-n2c(SCC(=O)Nc3ncc(Cl)cc3Cl)nc3ccccc32)cc1] | 0.44 |
| 156 | 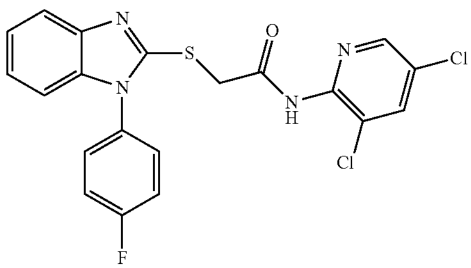 [SMILES: O=C(CSc1nc2ccccc2n1-c1ccc(F)cc1)Nc1ncc(Cl)cc1Cl] | 1.8 |
| 157 | 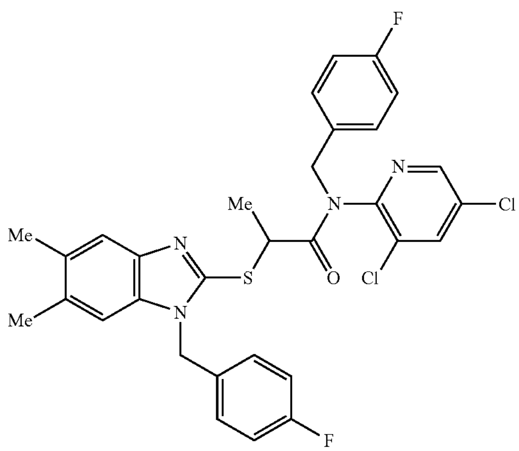 [SMILES: Cc1cc2nc(SC(C)C(=O)N(Cc3ccc(F)cc3)c3ncc(Cl)cc3Cl)n(Cc3ccc(F)cc3)c2cc1C] | >75 |
| 158 | 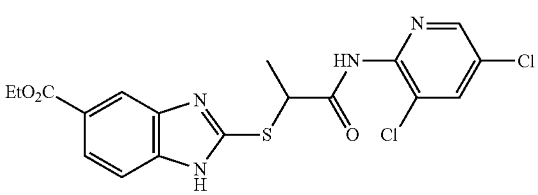 [SMILES: CCOC(=O)c1ccc2[nH]c(SC(C)C(=O)Nc3ncc(Cl)cc3Cl)nc2c1] | >75 |
| 159 | 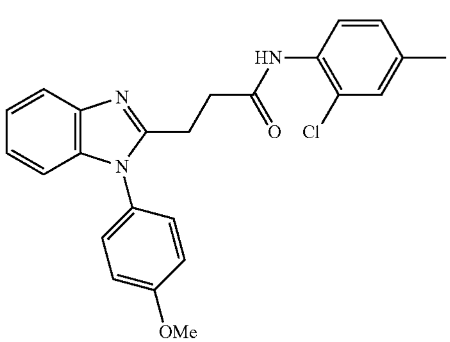 [SMILES: COc1ccc(-n2c(CCC(=O)Nc3ccc(C)cc3Cl)nc3ccccc32)cc1] | >150 |

TABLE 5-continued

| entry | structure | EC$_{50}$ |
|---|---|---|
| 160 | 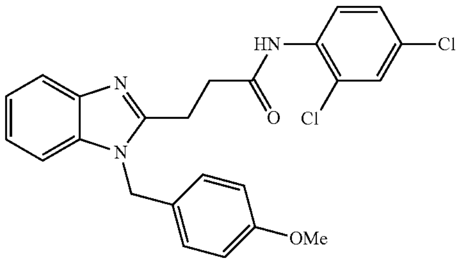 [SMILES: COc1ccc(Cn2c(CCC(=O)Nc3ccc(Cl)cc3Cl)nc3ccccc32)cc1] | >75 |
| 161 | 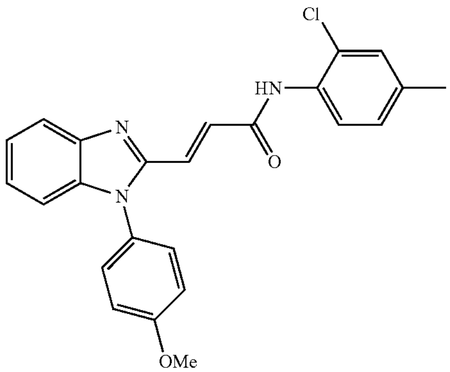 [SMILES: COc1ccc(-n2c(/C=C/C(=O)Nc3ccc(C)cc3Cl)nc3ccccc32)cc1] | >75 |
| 162 | 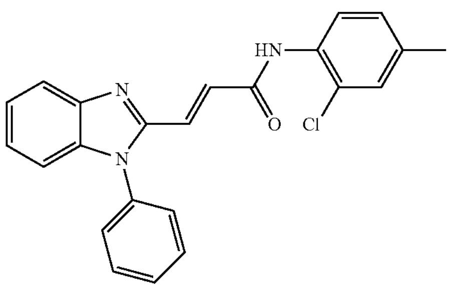 [SMILES: Cc1ccc(NC(=O)/C=C/c2nc3ccccc3n2-c2ccccc2)c(Cl)c1] | >75 |
| 163 | 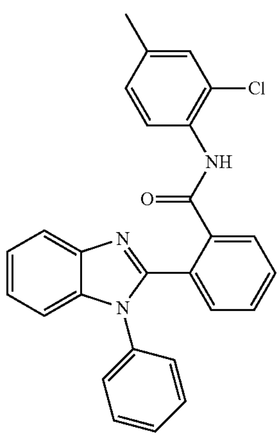 [SMILES: Cc1ccc(NC(=O)c2ccccc2-c2nc3ccccc3n2-c2ccccc2)c(Cl)c1] | >50 |
| 164 | 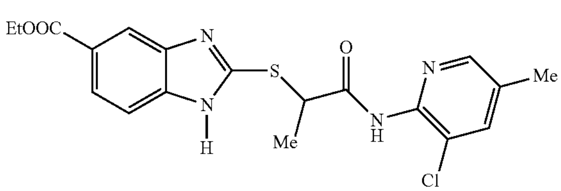 [SMILES: CCOC(=O)c1ccc2[nH]c(SC(C)C(=O)Nc3ncc(C)cc3Cl)nc2c1] | >75 |

TABLE 5-continued

| entry | structure | EC$_{50}$ |
|---|---|---|
| 165 | 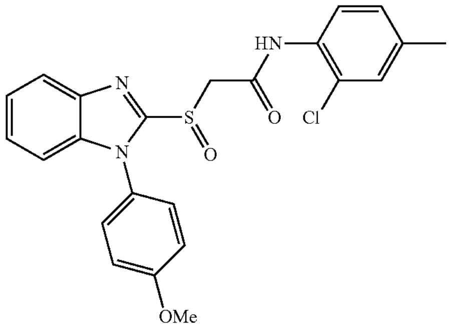 [SMILES: COc1ccc(-n2c(S(=O)CC(=O)Nc3ccc(C)cc3Cl)nc3ccccc32)cc1] | 4.2 |
| 166 | 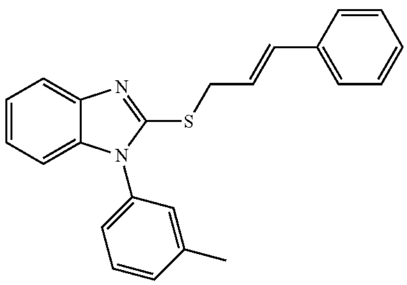 [SMILES: Cc1cccc(-n2c(SC/C=C/c3ccccc3)nc3ccccc32)c1] | >10 |
| 167 | 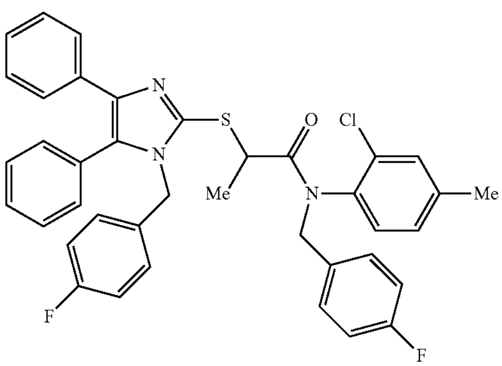 [SMILES: Cc1ccc(N(Cc2ccc(F)cc2)C(=O)C(C)Sc2nc(-c3ccccc3)c(-c3ccccc3)n2Cc2ccc(F)cc2)c(Cl)c1] | >75 |
| 168 | 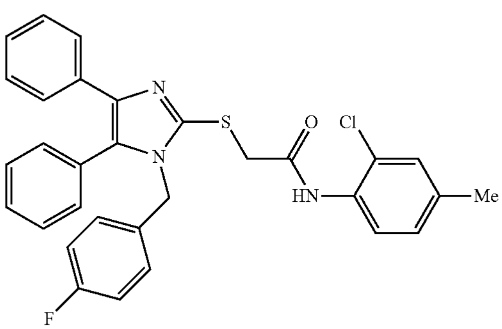 [SMILES: Cc1ccc(NC(=O)CSc2nc(-c3ccccc3)c(-c3ccccc3)n2Cc2ccc(F)cc2)c(Cl)c1] | >75 |
| 169 | 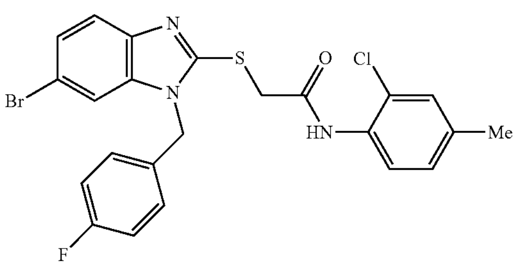 [SMILES: Cc1ccc(NC(=O)CSc2nc3ccc(Br)cc3n2Cc2ccc(F)cc2)c(Cl)c1] | >75 |

TABLE 5-continued

| entry | structure | EC$_{50}$ |
|---|---|---|
| 170 | 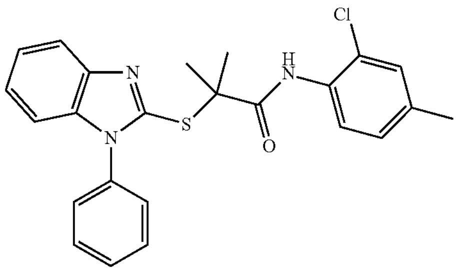 [SMILES: Cc1ccc(NC(=O)C(C)(C)Sc2nc3ccccc3n2-c2ccccc2)c(Cl)c1] | >75 |
| 171 | 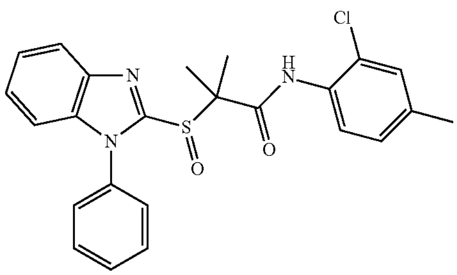 [SMILES: Cc1ccc(NC(=O)C(C)(C)S(=O)c2nc3ccccc3n2-c2ccccc2)c(Cl)c1] | >75 |
| 172 | 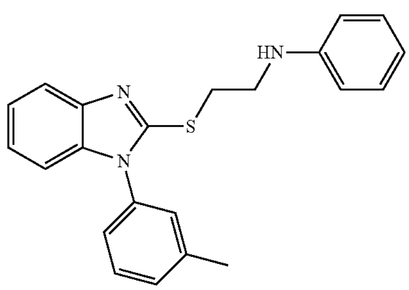 [SMILES: Cc1cccc(-n2c(SCCNc3ccccc3)nc3ccccc32)c1] | >75 |
| 173 | 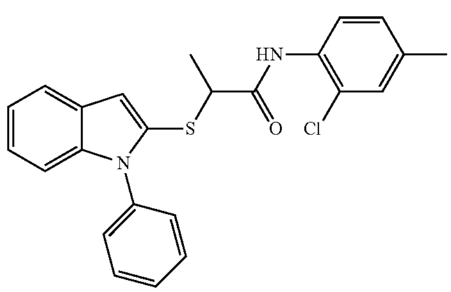 [SMILES: Cc1ccc(NC(=O)C(C)Sc2cc3ccccc3n2-c2ccccc2)c(Cl)c1] | >9.3 |

Figure 1B:
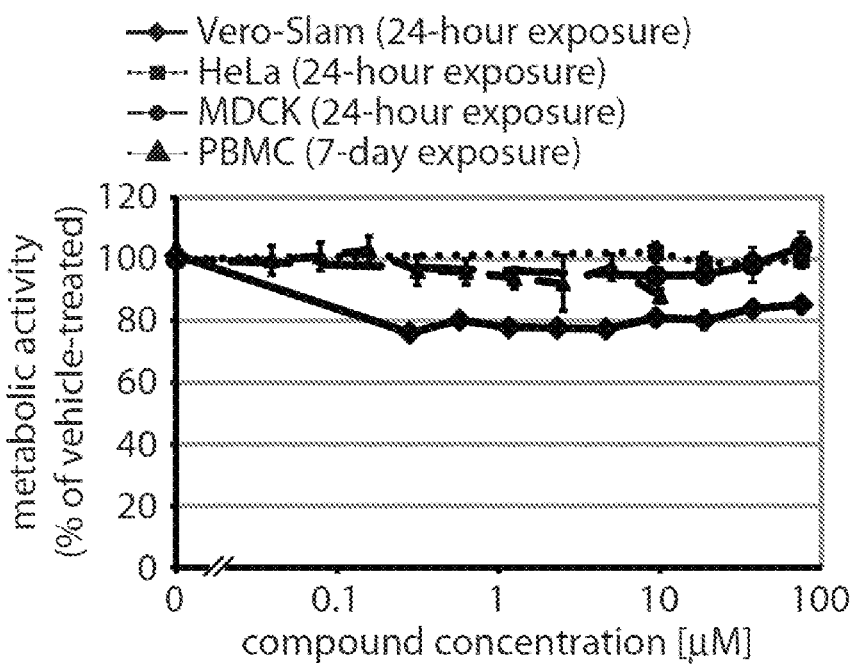
FIG. 1B shows data on the assessment of metabolic activity of cells after incubation in the presence of JMN3-003 for 24 hours. Results for human (HeLa), primate (Vero-Slam), and canine (MDCK) cell lines and primary human PBMCs are shown. Values reflect averages of four replicates±SD.

Synthetic optimization and structural confirmation of the scaffold returned a typical analog JMN3-003 (FIG. 1A), which showed potent activity against MeV and a selection of clinically significant members of the para- and orthomyxovirus families (FIG. 1B, inhibitory concentrations for a larger panel of myxovirus family members are summarized in FIG. 10).

Metabolic activity of cells exposed to JMN3-003 was unchanged at 75 μM, the highest assessable concentration based on solubility of the substance in growth media (FIG. 1B). These data support potent anti-myxovirus activity of certain compound with active concentrations ranging from 10 to 80 nM depending on the target virus.

Additional compounds with data on the suppression of viral cytopathic effect (CPE) and reduction of virus yield are included in the tables below (EC$_{50}$).

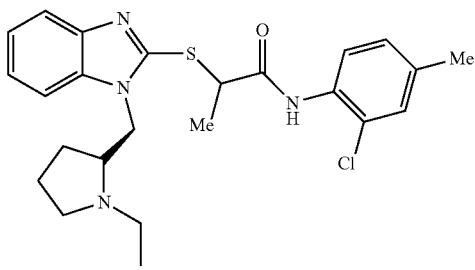 3.58 (CPE)
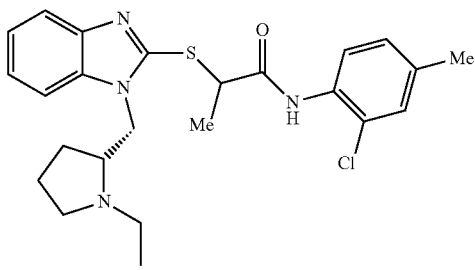 5.52
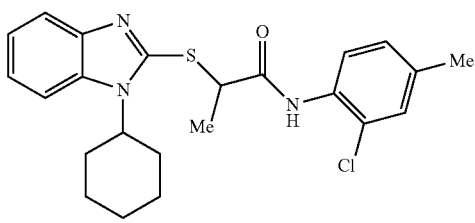 [SMILES: Cc1ccc(NC(=O)C(C)Sc2nc3ccccc3n2C2CCCCC2)c(Cl)c1] 0.29
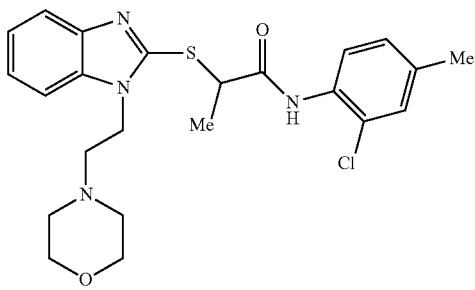 [SMILES: Cc1ccc(NC(=O)C(C)Sc2nc3ccccc3n2CCN2CCOCC2)c(Cl)c1] 4.85
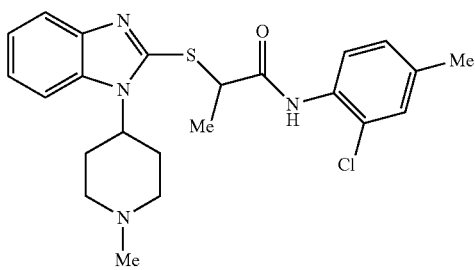 [SMILES: Cc1ccc(NC(=O)C(C)Sc2nc3ccccc3n2C2CCN(C)CC2)c(Cl)c1] 1.5
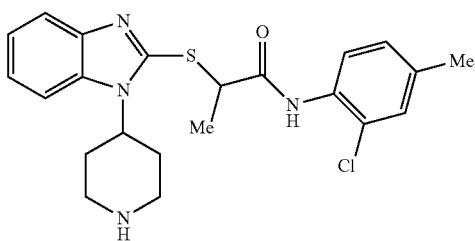 [SMILES: Cc1ccc(NC(=O)C(C)Sc2nc3ccccc3n2C2CCNCC2)c(Cl)c1] >75

-continued
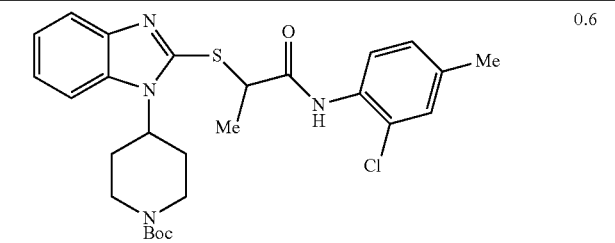 0.6
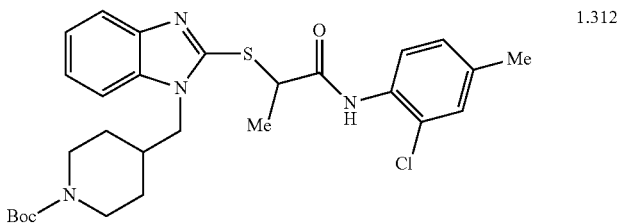 1.312
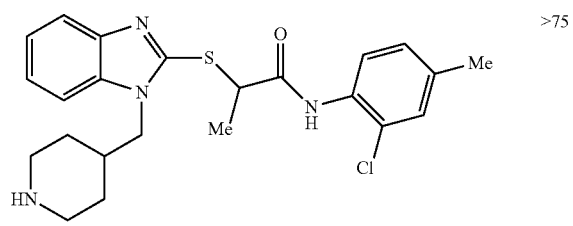 >75
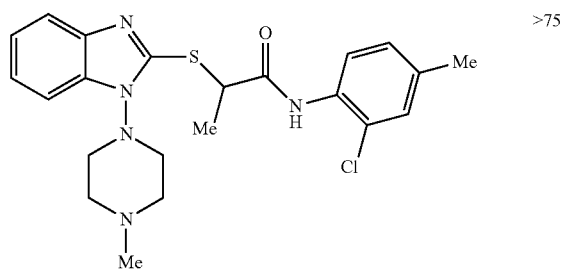 >75
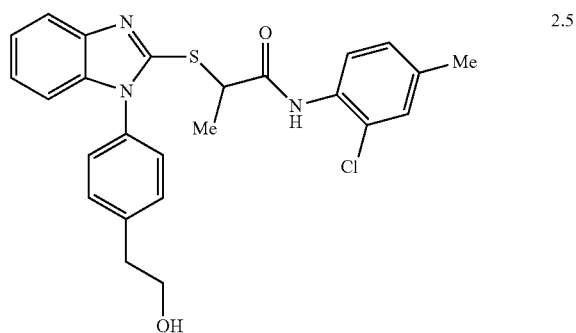 2.5
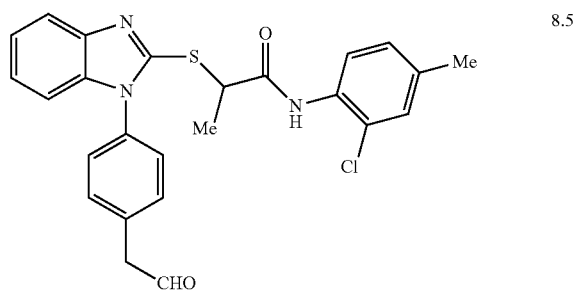 8.5

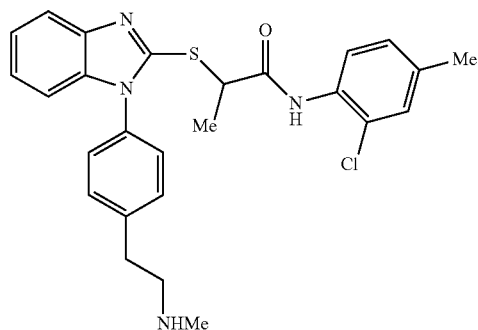 [SMILES: CNCCc1ccc(-n2c(SC(C)C(=O)Nc3ccc(C)cc3Cl)nc3ccccc32)cc1] 8.72
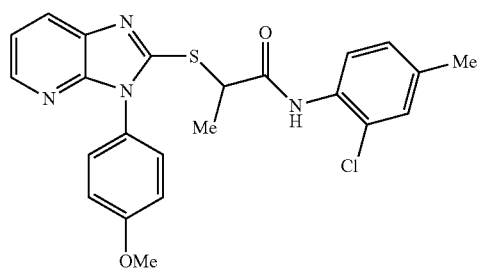 [SMILES: COc1ccc(-n2c(SC(C)C(=O)Nc3ccc(C)cc3Cl)nc3cccnc32)cc1] 1.65
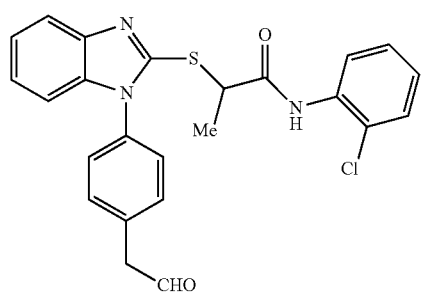 [SMILES: CC(Sc1nc2ccccc2n1-c1ccc(CC=O)cc1)C(=O)Nc1ccccc1Cl] 18.75
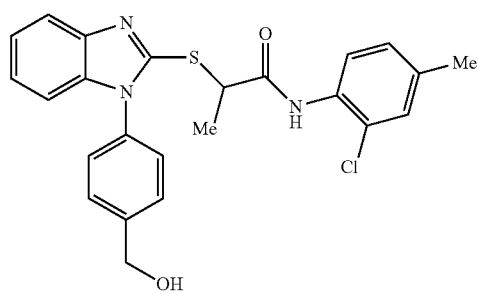 [SMILES: Cc1ccc(NC(=O)C(C)Sc2nc3ccccc3n2-c2ccc(CO)cc2)c(Cl)c1] 3.91
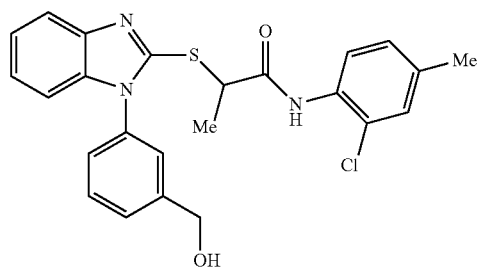 [SMILES: Cc1ccc(NC(=O)C(C)Sc2nc3ccccc3n2-c2cccc(CO)c2)c(Cl)c1] 0.7

-continued
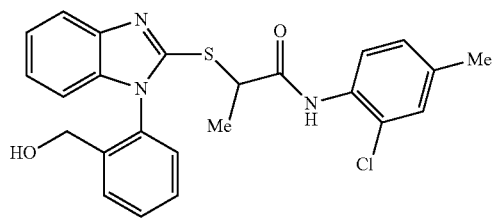 [SMILES: Cc1ccc(NC(=O)C(C)Sc2nc3ccccc3n2-c2ccccc2CO)c(Cl)c1] 0.8
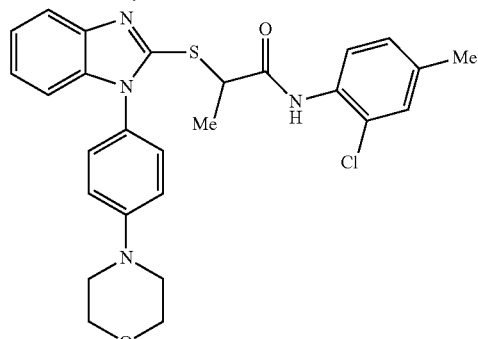 0.3
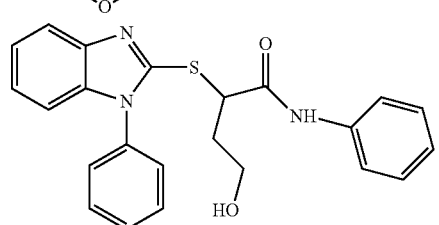 27.8
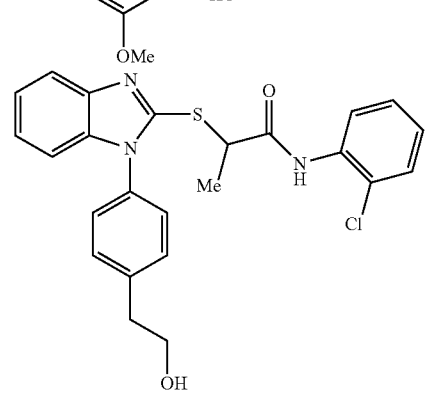 4.68
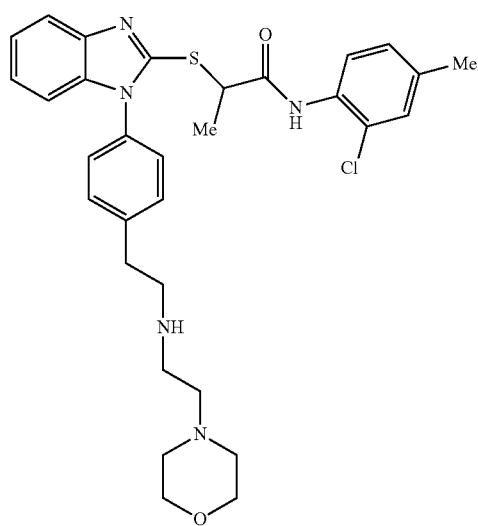 [SMILES: Cc1ccc(NC(=O)C(C)Sc2nc3ccccc3n2-c2ccc(CCNCCN3CCOCC3)cc2)c(Cl)c1] 1.913

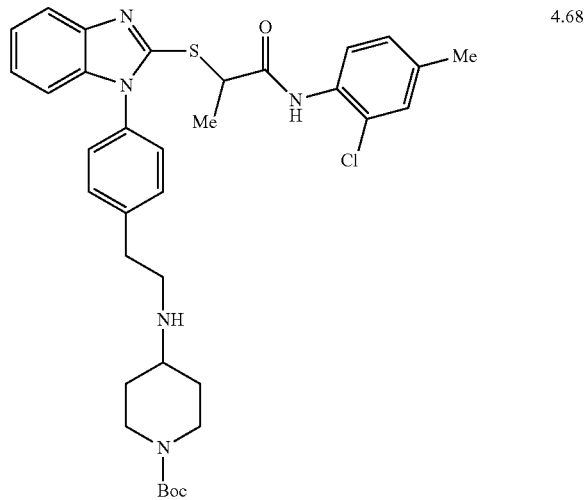
4.68
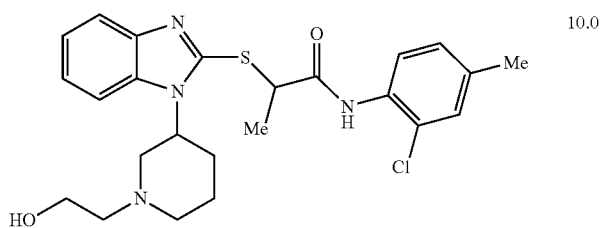
10.0
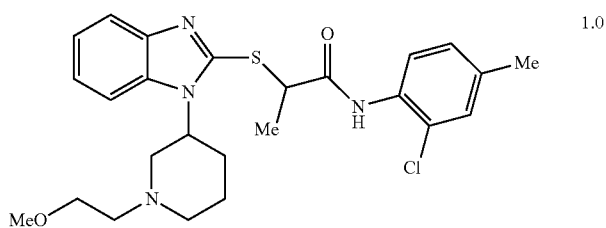
1.0
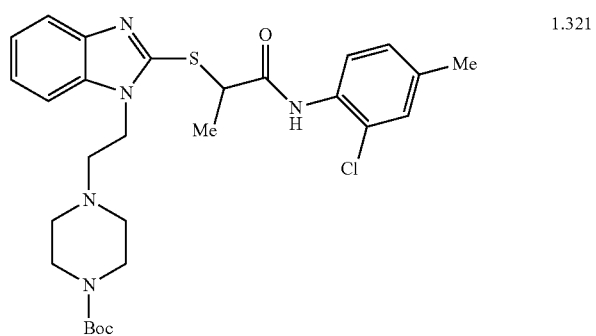
1.321

-continued
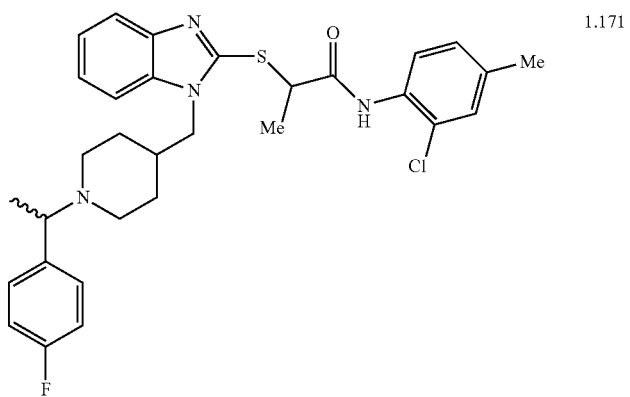 1.171
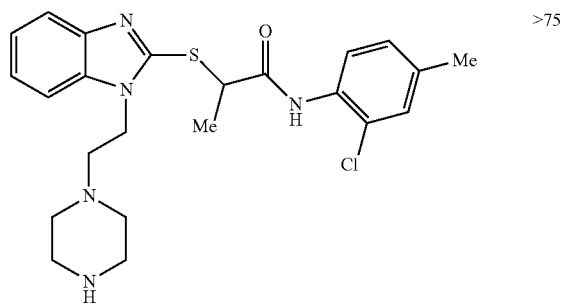 >75
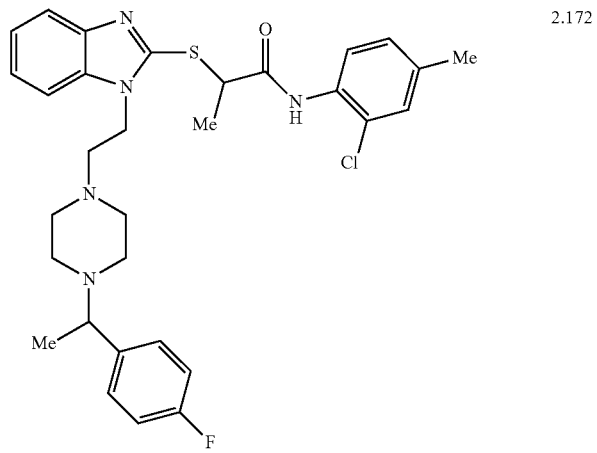 2.172
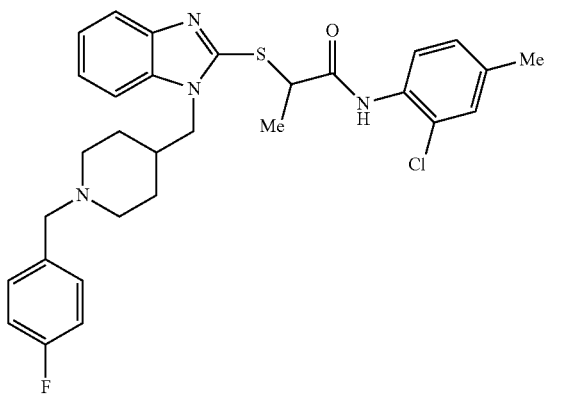 [SMILES: Cc1ccc(NC(=O)C(C)Sc2nc3ccccc3n2CC2CCN(Cc3ccc(F)cc3)CC2)c(Cl)c1] 1.176

-continued
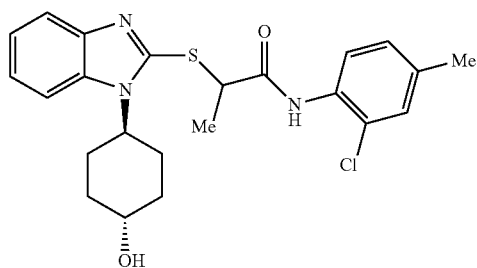 [SMILES: Cc1ccc(NC(=O)C(C)Sc2nc3ccccc3n2[C@H]2CC[C@H](O)CC2)c(Cl)c1]
2.737
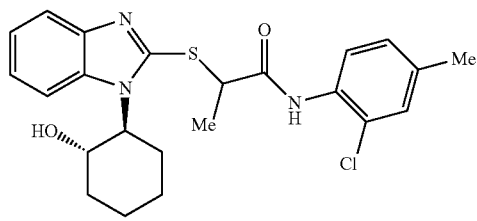 [SMILES: Cc1ccc(NC(=O)C(C)Sc2nc3ccccc3n2[C@H]2CCCC[C@@H]2O)c(Cl)c1]
0.8724
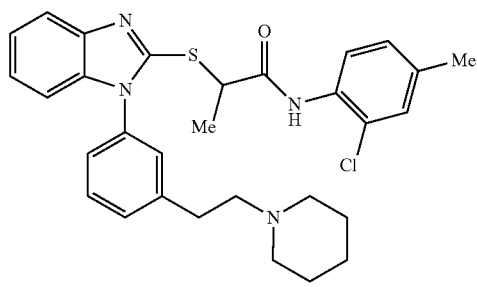 [SMILES: Cc1ccc(NC(=O)C(C)Sc2nc3ccccc3n2-c2cccc(CCN3CCCCC3)c2)c(Cl)c1]
1.522
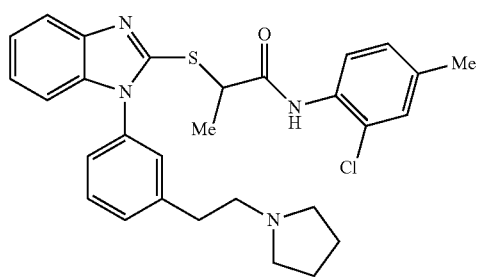 [SMILES: Cc1ccc(NC(=O)C(C)Sc2nc3ccccc3n2-c2cccc(CCN3CCCC3)c2)c(Cl)c1]
1.662
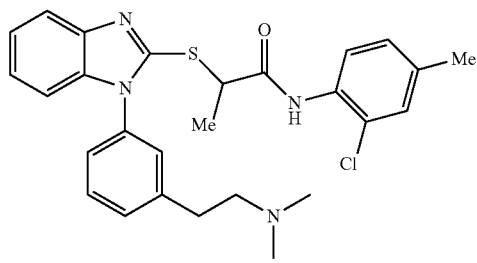 [SMILES: Cc1ccc(NC(=O)C(C)Sc2nc3ccccc3n2-c2cccc(CCN(C)C)c2)c(Cl)c1]
1.224
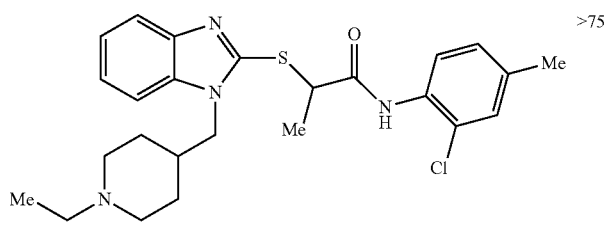
>75

-continued
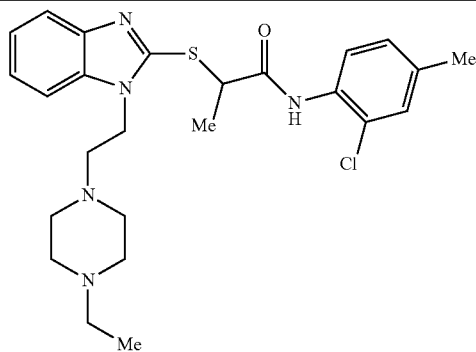
18.75
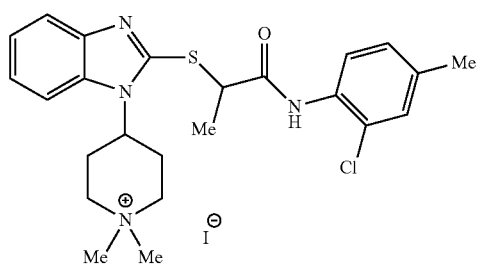 [SMILES: Cc1ccc(NC(=O)C(C)Sc2nc3ccccc3n2C2CC[N+](C)(C)CC2)c(Cl)c1 ; [I-]]
>75
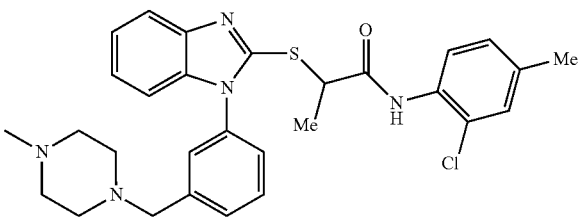 [SMILES: Cc1ccc(NC(=O)C(C)Sc2nc3ccccc3n2-c2cccc(CN3CCN(C)CC3)c2)c(Cl)c1]
1.28
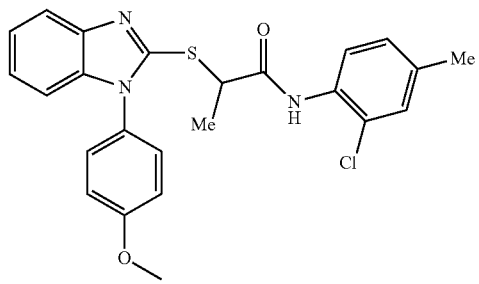 [SMILES: COc1ccc(-n2c(SC(C)C(=O)Nc3ccc(C)cc3Cl)nc3ccccc32)cc1]
0.0312 (MeV)
0.0792 (MeV)
0.01323 (WSN)
0.08 (HPIV3)
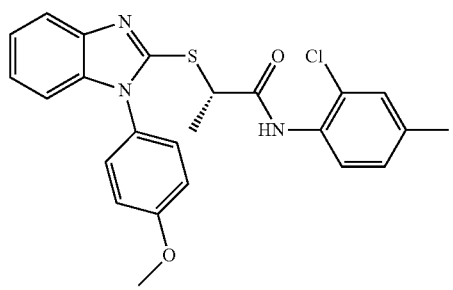 [SMILES: COc1ccc(-n2c(S[C@@H](C)C(=O)Nc3ccc(C)cc3Cl)nc3ccccc32)cc1]
0.03731 (MeV)
0.005 (WSN)
0.08 (HPIV3)

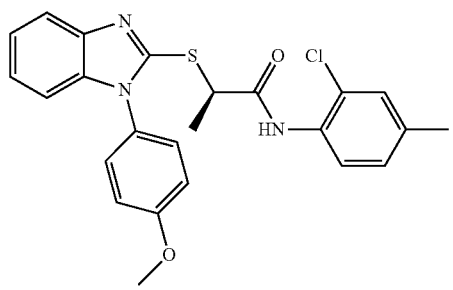 [SMILES: COc1ccc(-n2c(S[C@H](C)C(=O)Nc3ccc(C)cc3Cl)nc3ccccc32)cc1] 0.8791 (MeV)
0.1574 (WSN)
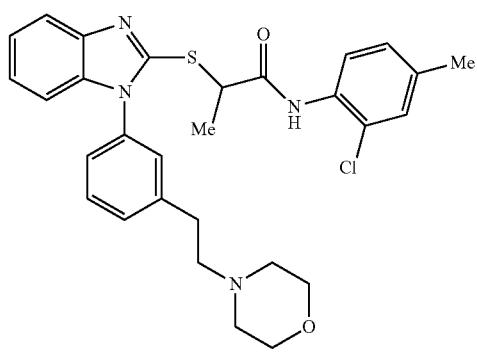 [SMILES: Cc1ccc(NC(=O)C(C)Sc2nc3ccccc3n2-c2cccc(CCN3CCOCC3)c2)c(Cl)c1] 0.01293 (MeV)
0.0003 (WSN)
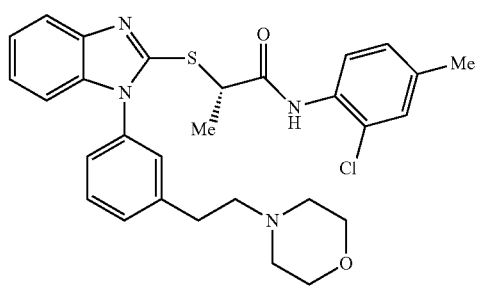 [SMILES: Cc1ccc(NC(=O)[C@H](C)Sc2nc3ccccc3n2-c2cccc(CCN3CCOCC3)c2)c(Cl)c1] 0.01077 (MeV)
0.0015 (WSN)
0.016 (HPIV3)
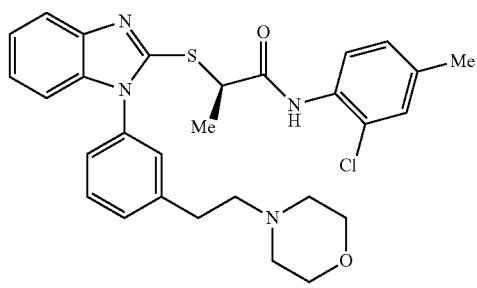 [SMILES: Cc1ccc(NC(=O)[C@@H](C)Sc2nc3ccccc3n2-c2cccc(CCN3CCOCC3)c2)c(Cl)c1] 0.2116 (MeV)
0.1083 (WSN)
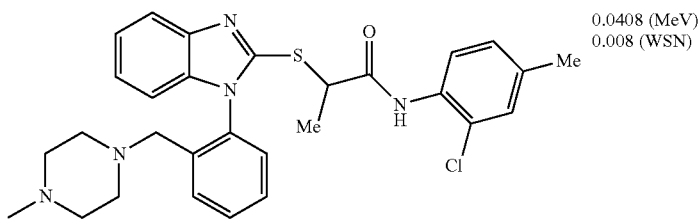 0.0408 (MeV)
0.008 (WSN)

-continued
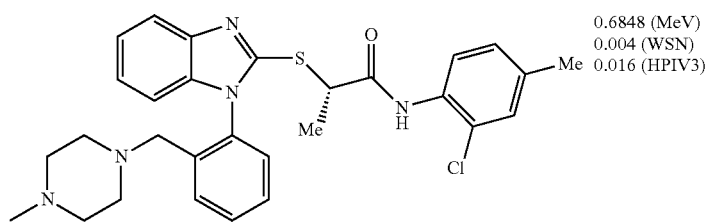
0.6848 (MeV)
0.004 (WSN)
0.016 (HPIV3)
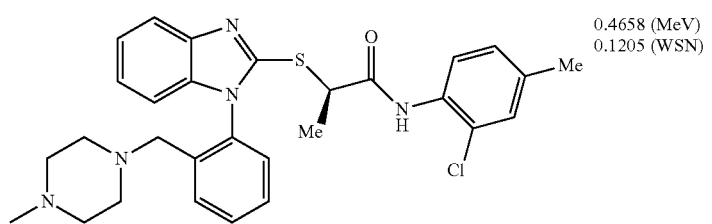
0.4658 (MeV)
0.1205 (WSN)
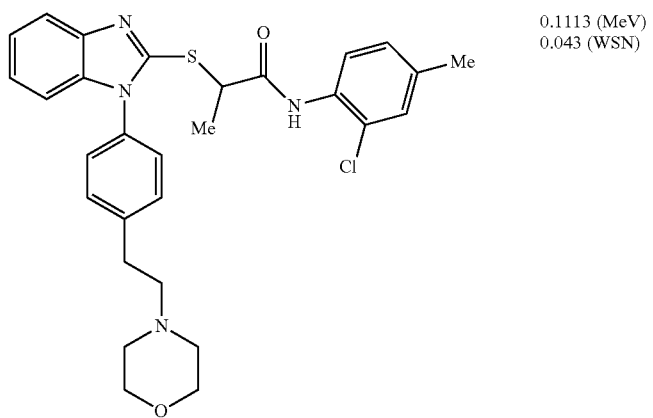
0.1113 (MeV)
0.043 (WSN)
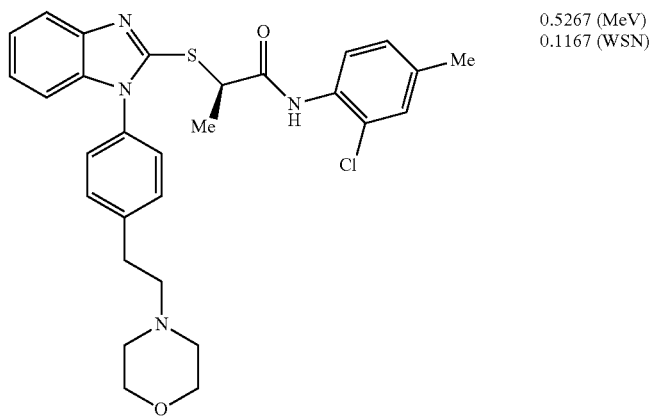
0.5267 (MeV)
0.1167 (WSN)

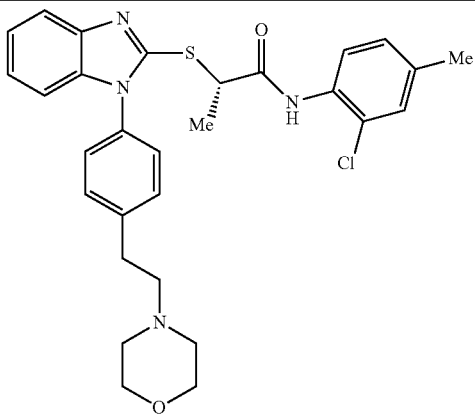

0.1787 (MeV)
0.036 (WSN)
0.08 (HPIV3)

Example 2

Antiviral Activity of a Compound JMN3-003 is Host Cell-Specific

Figure 2:
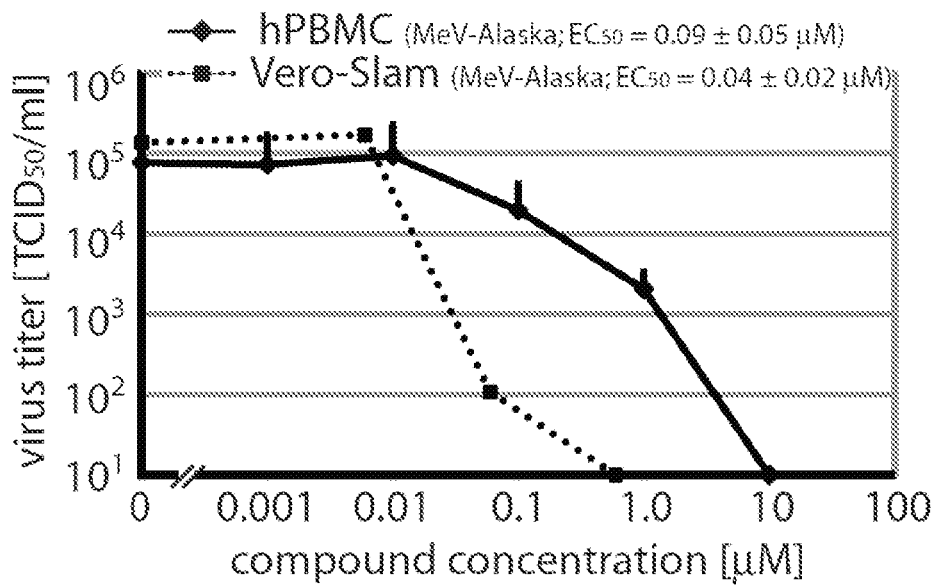
FIG. 2 shows data suggesting that the cellular target range of JMN3-003 extends to primary human cells. Dose-response curves for MeV-Alaska grown in the presence of JMN3-003 on human PBMCs originating from a mixed pool of healthy donors. Vero-Slam cell-based inhibition curves are shown for comparison. Values reflect averages of three replicates. EC50 concentrations±SD are derived from four-parameter non-linear regression modeling.

To further explore whether JMN3-003 meets the profile of a host-directed antiviral, whether the extent of inhibition is determined by the species origin of the host cell used for virus propagation was examined. Based on its broad host cell range, inhibition of influenza A/WSN replication was monitored. In addition to higher mammalian (canine and primate) cell lines, cells of rodent and avian origin were tested, which are all permissive for influenza A/WSN infection. While inhibitory concentrations obtained for all higher mammalian cell lines examined were similar, A/WSN inhibition by JMN3-003 was less effective on some rodent cell lines and vanished entirely when virus was propagated on murine or avian cells (FIG. 11). However, inhibitory activity extended fully to primary human PBMCs (FIG. 2). For the latter, inhibition of MeV-Alaska was monitored due to efficient growth of MeV isolates on PBMCs. The host cell species-effect of antiviral activity of JMN3-003 is consistent with specific targeting of cellular factors by the compound, while arguing against docking to conserved viral factors or an undesirable promiscuous, unspecific mode of activity.

Example 3

JMN3-003 Shows Metabolic Stability In Vitro

Figure 3A:
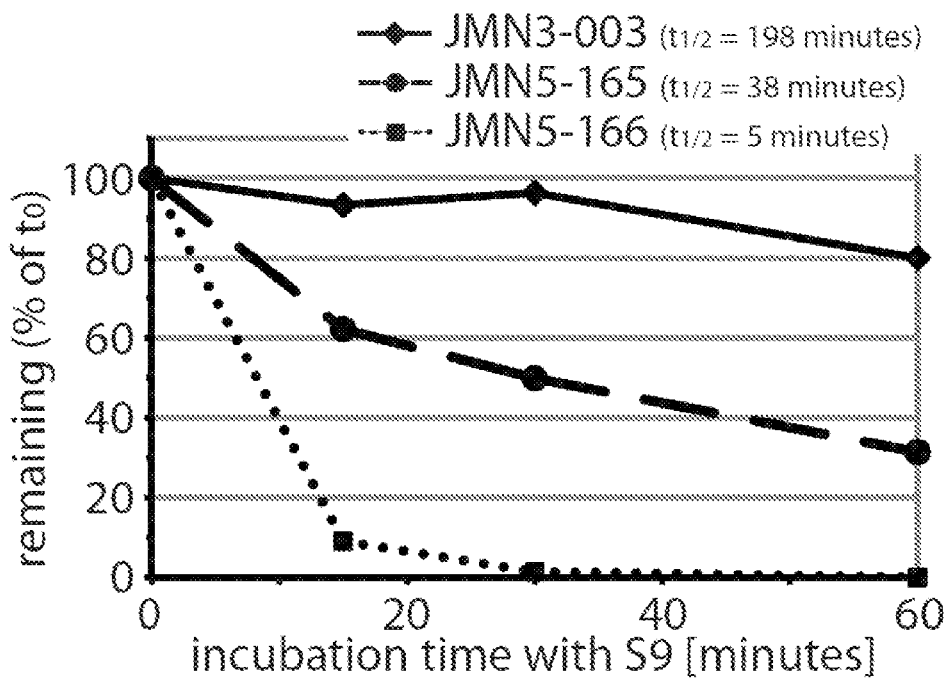

The central 2-thio-connector found in the chemical scaffold of JMN3-003 may render the compound susceptible to rapid phase I oxidation in vivo, thus possibly compromising its developmental potential. To test metabolic stability of the substance early in development, JMN3-003 was exposed to human S-9 hepatocyte subcellular fractions as an in vitro indicator for phase I metabolism. After a 60-minute exposure, approximately 80% of the input material remained intact, corresponding to an extrapolated half-life of approximately 200 minutes (FIG. 3A). Unstable analogs of JMN3-003, JMN5-165 and JMN5-166, returned half lives of 38 and 5 minutes in this assay, respectively, confirming metabolic competency of the S9 fractions used.

Assessment of JMN3-003 stability in human plasma in comparison with unstable Procaine and stable Procainamide corroborated these results, since JMN3-003 integrity was virtually unaffected after a 120-minute incubation period (FIG. 3B). Taken together, these findings suggest desirable metabolic stability for the JMN3-003 scaffold, recommending it for further mechanistic characterization. The data are corroborated by the good metabolic stability reported for the compound 4-(2-((5-bromo-4-(4-cyclopropylnaphthalen-1-yl)-4H-1,2,4-triazol-3-yl)thio)acetamido)-3-chlorobenzoic acid, RDEA-806, a non-nucleoside inhibitor of HIV reverse transcriptase and clinical precedent, which shares the 2-thio-connector of JMN3-003 but lacks MeV inhibitory activity in our assays.

Example 4

Temporary Arrest in Cell Cycle Progression

Figure 4A:
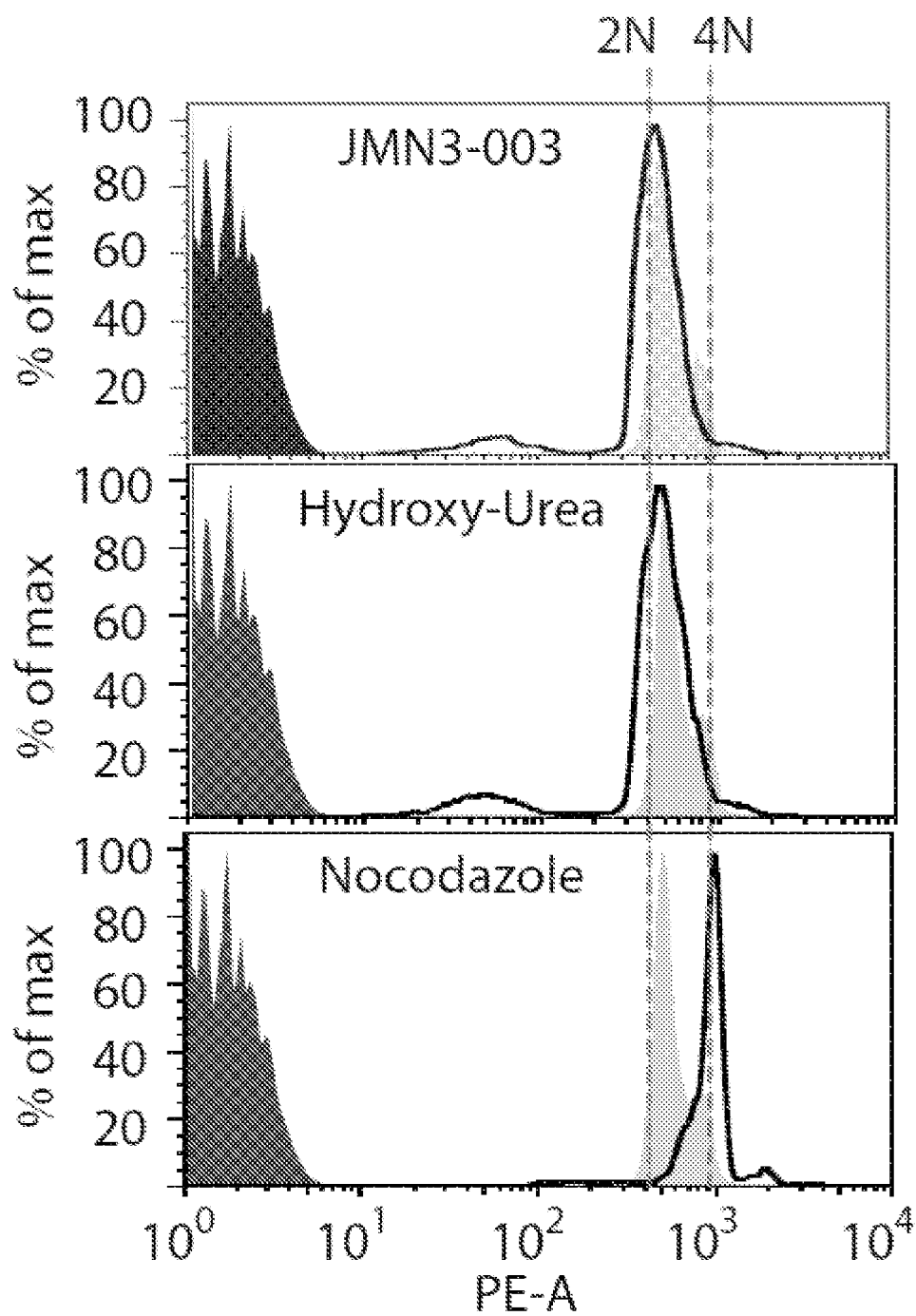
FIGS. 4A-D show data suggesting cell exposure to compound JMN3-003 induces a temporary G1/S phase cell cycle arrest. A) FACS analysis of acridine orange-stained HeLa cells incubated in the presence of JMN3-003 or hydroxyurea for 36 hours, or nocodazole for 16 hours. Dark grey shaded areas show unstained cells, light grey areas correspond to vehicle-treated control cells, and areas under open black curves represent treated cell populations. Dashed vertical lines indicate 2 N (G1/S) and 4N (G2/M) DNA contents. Data shown are representative of three experiments and reflect 10,000 events/treatment conditions. B) Analysis of the phosphorylation status of cdc2-cyclin B kinase through immunoblotting using specific antisera directed against phospho-cdc2 (Tyr15; α cdc2-P) or total cdc2 (α cdc2) for comparison. Results shown are representative of three experiments. C) Wash-out of JMN3-003 restores cell proliferation. Growth rates of Vero cells were determined after 30-hour exposure of cells to JMN3-003 or vehicle only, followed by wash-out of the substance. Values reflect cell divisions per day and are based on averages of six independent replicate experiments±SEM. D) G1/S phase cell cycle arrest does not affect MeV proliferation per se. Dose-response curves for Alsterpaullone, a nanomolar CDK1/cyclin B kinase inhibitor, and MeV-Alaska grown on Vero-Slam cell. Titers of cell-associated viral particles were determined 36 hours post-infection through TCID50 titration. JMN3-003 was examined in parallel for comparison. Values reflect averages of three replicates±SD.
Figure 4B:
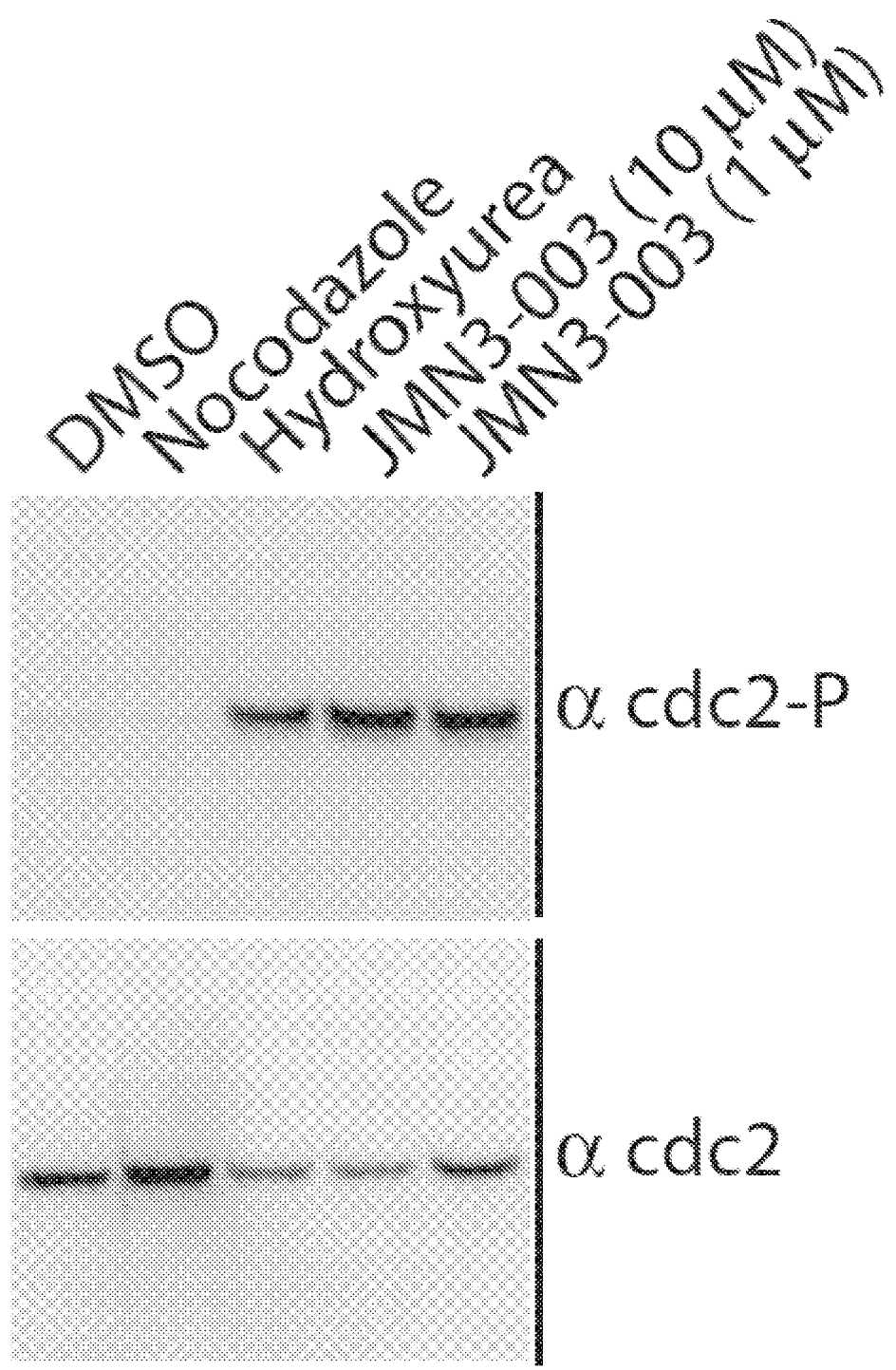

Since direct cytotoxicity of JMN3-003 was low for all cell lines examined, the effect of the substance on cell cycle progression was tested. Analysis of the DNA content of cells continuously treated with JMN3-003 for 36 hours by flow cytometry revealed accumulation of cells in a single population with 2N DNA content, which closely resembled the profile of a reference cell population exposed to hydroxyurea but markedly differed from the 4N DNA content of nocodazole-treated cells (FIG. 4A). Nocodazole interferes with microtubule polymerization, resulting in a G2/M arrest, whereas hydroxyurea is thought to lead to an arrest in the G1/S-phase through depletion of cellular dNTP pools. To further explore the effect of JMN3-003 on cell cycle progression, the phosphorylation status of the cdc2-cyclin B kinase was monitored after exposure of cells to either the compound, hydroxyurea, or nocodazole. Pivotal in regulating the G2/M transition, cdc2-cyclin B kinase is inactivated through phosphorylation during the G2-phase. Accumulation in its phosphorylated form thus indicates a G1 arrest. As in hydroxyurea-treated controls, exposure of cells to JMN3-003 resulted in increased steady state levels of phosphorylated cdc2-cyclin B kinase, supporting a G1-phase arrest (FIG. 4B).

Figure 4C:
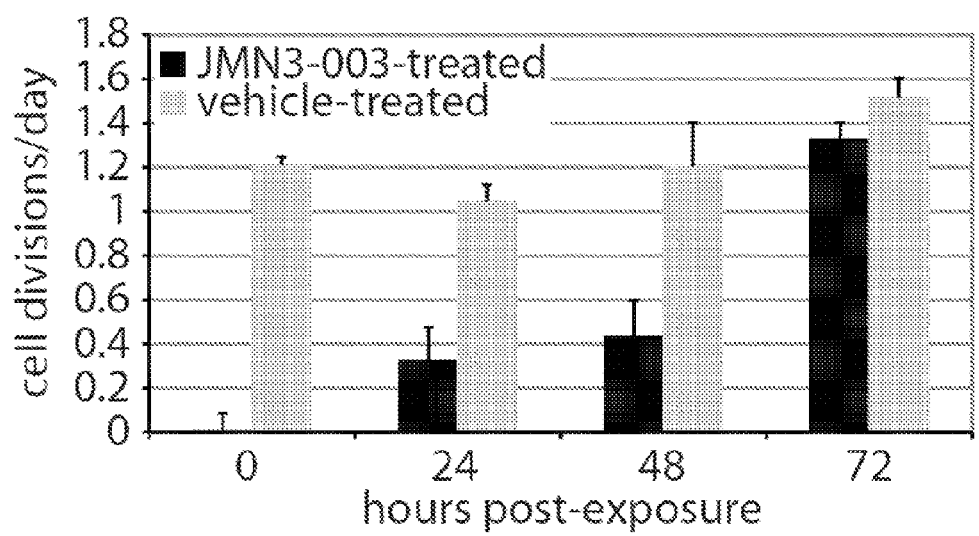

To test whether this JMN3-003-induced arrest is permanent or temporary, cells were incubated in the presence of compound or vehicle alone for 30 hours, followed by removal of the substance and reseeding of cells at identical densities. Monitoring cell growth over an additional 72-hour incubation period in the absence of JMN3-003 revealed that proliferation rates resumed those of untreated control cells after removal of the compound (FIG. 4C), indicating reversibility of the growth arrest.

In contrast to members of the orthomyxovirus family, paramyxovirus replication takes place in the cytosol and; thus, is considered not to be immediately dependent on active cell proliferation. In fact, MeV itself has been shown to induce a G1/S arrest in infected T lymphoyctes, confirming that cell cycle progression is not required for virus replication.

Figure 4D:
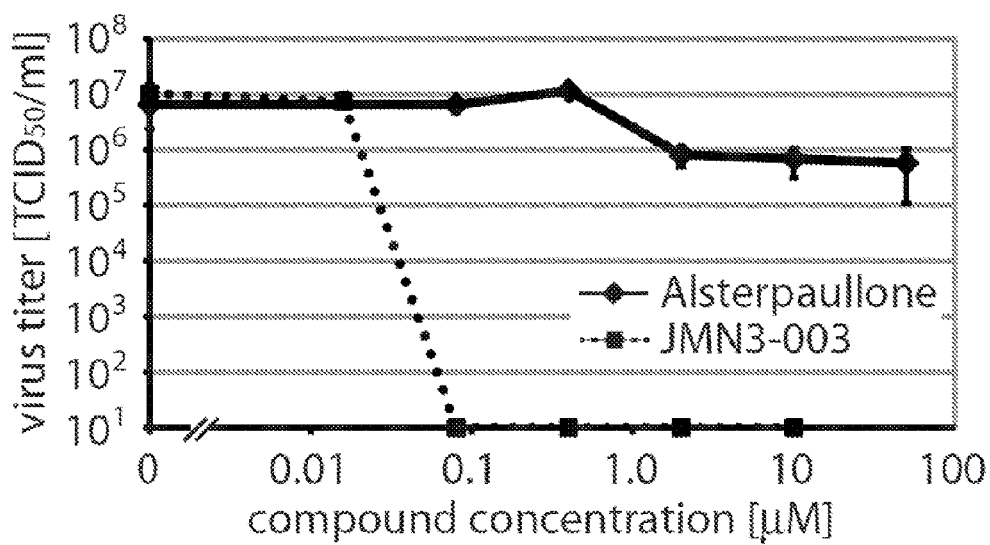

To directly test whether the JMN3-003-mediated growth arrest per se is causal for the antiviral effect of the compound, MeV-Alaska inhibition curves were generated of JMN3-003 in comparison with Alsterpaullone, a nanomolar inhibitor of cyclin-dependent kinases that reportedly induces a potent G1/S-phase cell cycle arrest. Even at the highest concentration assessed (50 µM), Alsterpaullone caused only a marginal reduction in MeV yields (FIG. 4D). These findings suggest that the antiviral effect of JMN3-003 is based on an upstream effect of the compound rather than being a consequence of the cell cycle arrest itself.

Example 5

Cellular mRNA Production and Protein Biosynthesis are Unperturbed by JMN3-003

Figure 5A:
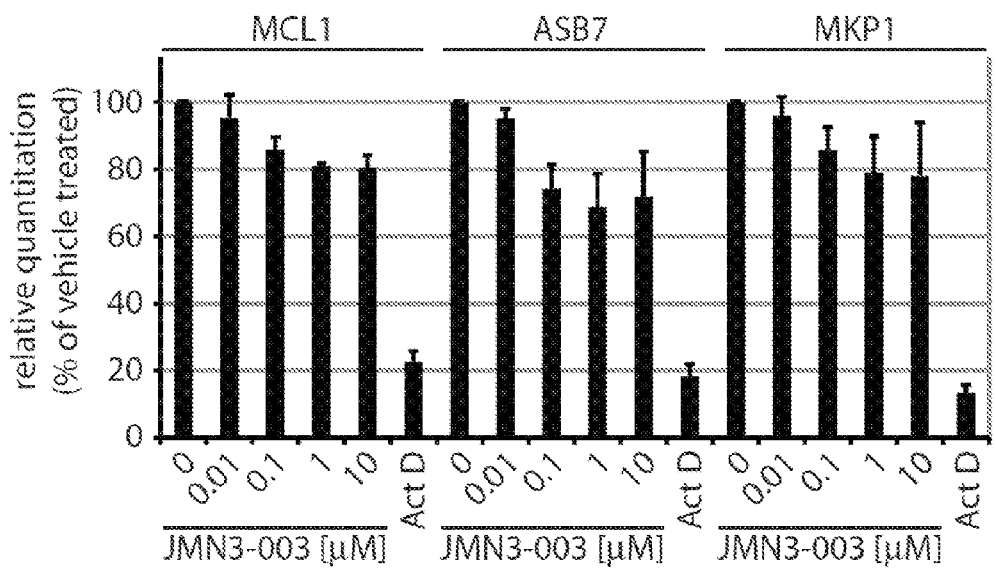
FIGS. 5A-D show data suggesting host cell mRNA synthesis and translation are unaffected by compound JMN3-003. A) Relative TaqMan RT-PCR-based quantitation of three unstable cellular mRNAs (MCL1, ASB7, MKP-1) after exposure of cells to JMN3-003 for six hours. Controls were treated with Actinomycine D (Act D) for comparison. CT values are expressed relative to vehicle-treated samples and reflect averages of three independent experiments, each analyzed in triplicate, ±SD. B-D) Expression of virus-encoded but not host cell or plasmid-encoded viral proteins is blocked by JMN3-003. Immunodetection of transiently expressed MeV-F (B), virus-encoded MeV-F (C), and virus-encoded influenza A/WSN M2(D) in cell lysates after incubation of cells in the presence of compound or vehicle only (DMSO) for 30 hours. As internal cellular standard, membranes were probed for GAPDH in parallel. Numbers correspond to average densitometric quantitations±SD of three experiments, representative immunoblots are shown. (ND: not determined)

To explore whether growth arrest of treated cells coincides with reduced host cell RNA synthesis or overall cell protein biosynthesis, the effect of JMN3-003 was assessed on host mRNA and protein production. Relative levels of three signature host mRNAs with short half lives, MCL1, ASB7 and MKP1, were determined by real time PCR after incubation of cells in the presence of different JMN3-003 concentrations ranging from 0.01 to 10 µM. In all cases, mRNA levels of JMN3-003-exposed cells were similar to those of the vehicle-treated references, while exposure to Actinomycin D, which blocks RNA synthesis through arrest of the transcription initiation complex, resulted in a major reduction in relative mRNA levels (FIG. 5A).

Figure 5B:
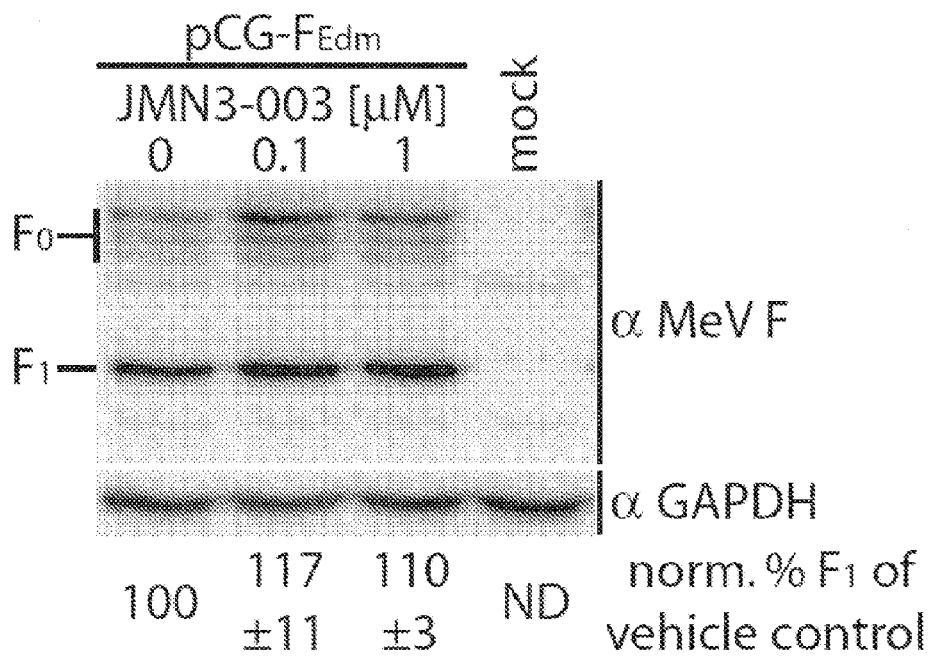
Figure 5C:
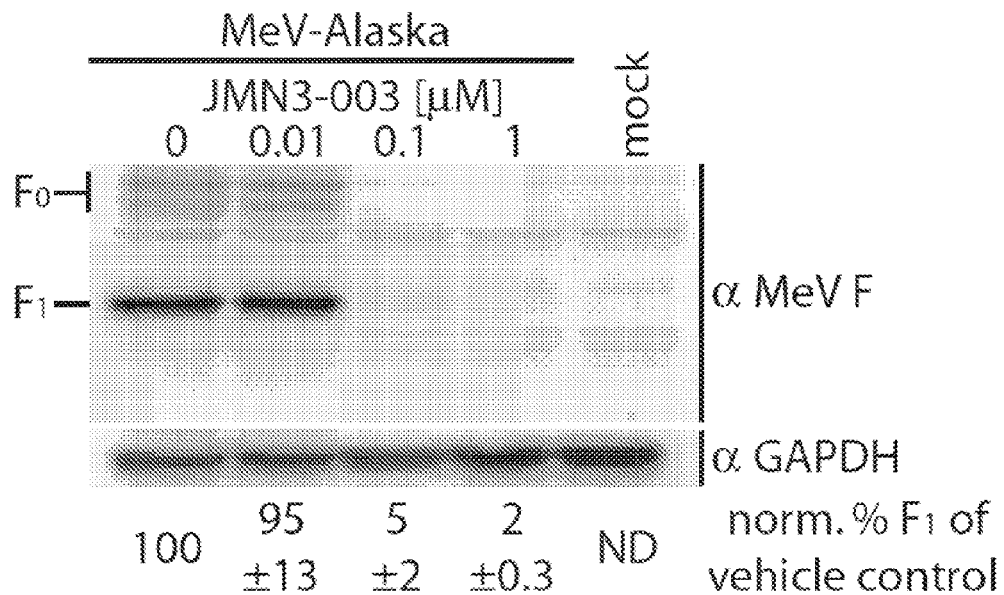
Figure 5D:
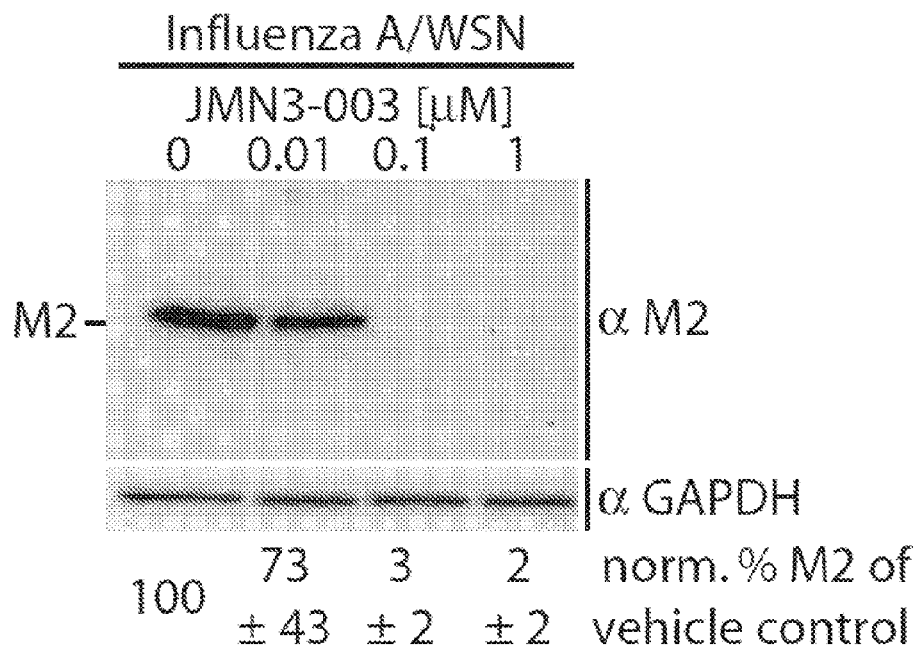

Immunodetection of cellular GAPDH and plasmid-encoded MeV F protein under the control of the CMV promoter demonstrated that productive transcription in the presence of the compound furthermore coincides with uninterrupted translation and, in the case of F, cotranslational insertion into the host secretory system (FIG. 5B). Furthermore, equivalent levels of proteolytically processed F1 material in JMN3-003 and vehicle-exposed cells indicated that intracellular vesicular transport remains intact in the presence of JMN3-003, since cleavage is mediated by the cellular protease furin in a late-Golgi compartment. In contrast to host encoded or transiently expressed proteins, expression of virus-encoded proteins in the context of paramyxovirus or orthomyxovirus infection was fully blocked by 100 nM JMN3-003 (FIGS. 5C and D). Thus, these observations demonstrate that the compound efficiently suppresses the expression of virus-encoded proteins, but that this is not due to general interference of the inhibitor with cellular mRNA synthesis or translation. This phenotype suggests possible interference of JMN3-003 with early steps of the viral life cycle, such as entry or viral RdRp activity, as the basis for antiviral activity.

Example 6

Inhibition of a Post-Entry Step of the Viral Life Cycle

Figure 6A:
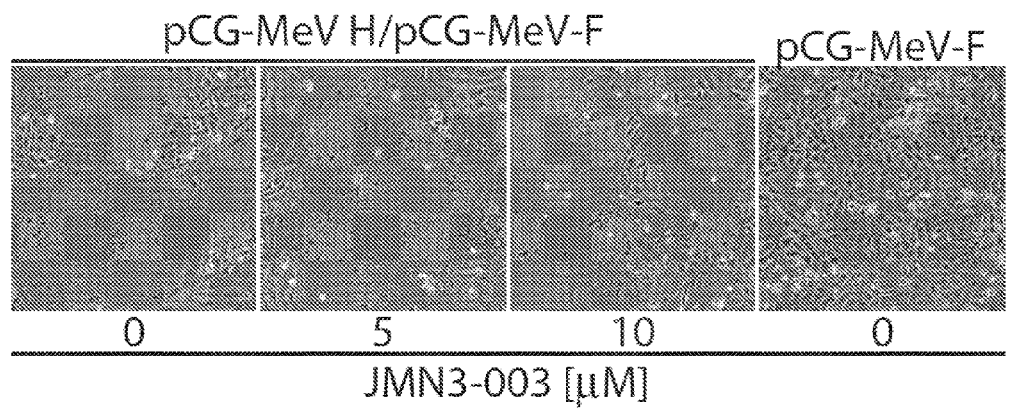
FIGS. 6A-E show data suggesting for in time-of-addition assays, JMN3-003 shows the inhibition profile of an RdRp blocker. A-B) Cell-to-cell fusion is unaffected by the compound. Microphotographs of MeV-H and F expressing Vero-Slam cells (A) and quantitative cell-to-cell fusion assays (B) show membrane fusion activities in the presence of JMN3-003 similar to those observed for vehicle (DMSO)-treated controls. The effect of fusion inhibitory peptide (FIP) is shown in (B) for comparison. C) JMN3-003 antiviral activity is reversible and not based on cell priming. Vero-Slam cells were pre-treated with 1.0 μM JMN3-003 for 60 minutes, followed by compound wash-out and incubation for the indicated time periods; at t0, cells were infected with MeV-Alaska. D) JMN3-003 lacks virucidal activity. MeV-Alaska particles were incubated with 1.0 μM JMN3-003 for 60 minutes, followed by dilution of compound to 1.0 nM and infection of cells at an MOI of 0.033 in the presence of vehicle (JMN3-003/infect./DMSO). Equally treated controls received vehicle only (DMSO/infect./DMSO), compound only after infection (DMSO/infect./JMN3-003), or compound for the duration of the experiment (JMN3-003/infect./JMN3-003). E) Addition of JMN3-003 (1.0 μM final concentration) at the indicated times post-infection of cells with MeVAlaska. For comparison, inhibition profiles of the MeV entry inhibitor AS-48 (75 μM) and RdRp blocker AS-136A (25 μM) are shown. Controls received vehicle only (DMSO) at the time of infection. For (C-E), values show titers of cell associated viral particles (TCID50/ml) and represent averages of at least three experiments±SD.
Figure 6B:
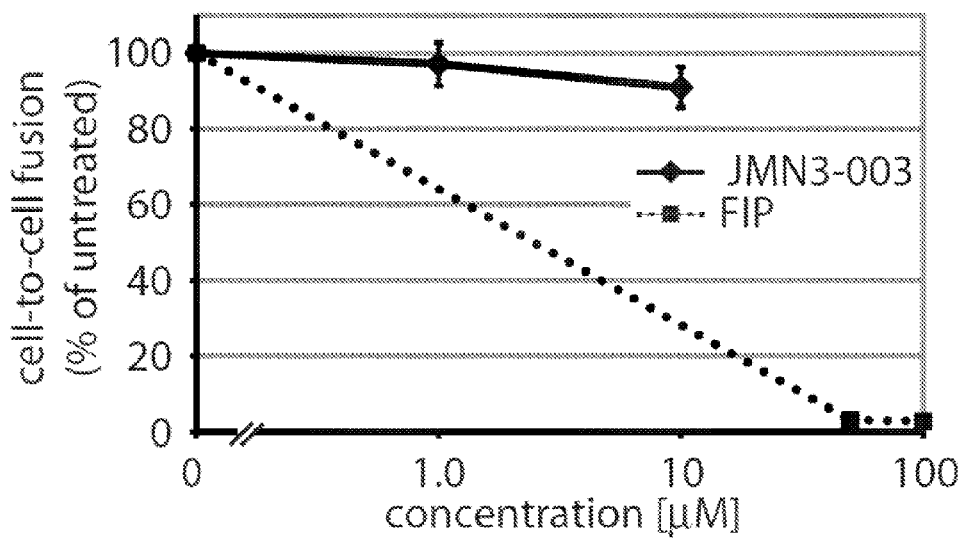

To differentiate between those alternatives and identify the point of arrest in the viral life cycle induced by JMN3-003, whether the compound blocks membrane fusion and thus viral entry was examined. Expression of plasmid-encoded paramyxovirus envelope glycoproteins in receptor-positive cells typically results in extensive cell-to-cell fusion, the hallmark cytopathic effect associated with most paramyxovirus infections in vitro. Transient membrane fusion assays allow a quantitative assessment of whether an inhibitor blocks viral entry or post-entry steps of the viral life cycle. When MeV glycoprotein-mediated cell-to-cell fusion was examined microscopically (FIG. 6A) and in a luciferase reporter-based quantitative cell-to-cell fusion assay (FIG. 6B) in the presence of JMN3-003, extensive membrane fusion was observed to be indistinguishable from that seen in vehicle-treated controls, indicating that the compound does not act as an entry inhibitor.

Figure 6C:
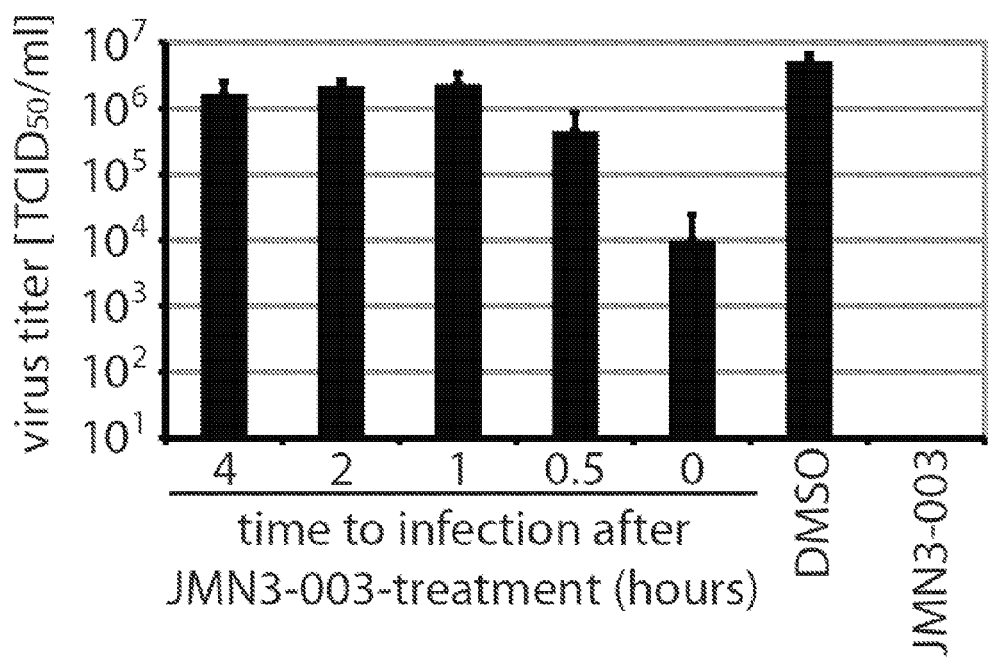
Figure 6D:
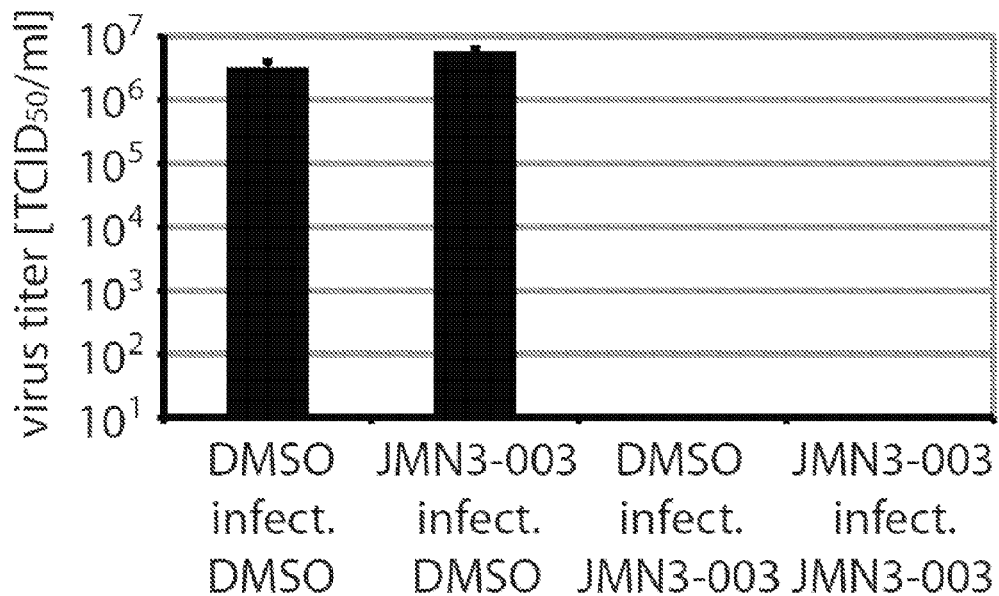

To determine whether JMN3-003 predisposes host cells against viral infection by inducing an antiviral state, cells were pre-treated with the compound, followed by wash-out of the substance and virus infection after different time periods. Independent of incubation time after removal of the compound, any substantial inhibitory effect was not detect in this set-up (FIG. 6C), suggesting against priming of the innate antiviral response by JMN3-003. Likewise, preincubation of viral particles with JMN3-003 prior to removal of the article and infection lacked any appreciable antiviral effect (FIG. 6D), excluding direct virucidal activity of the substance.

Figure 6E:
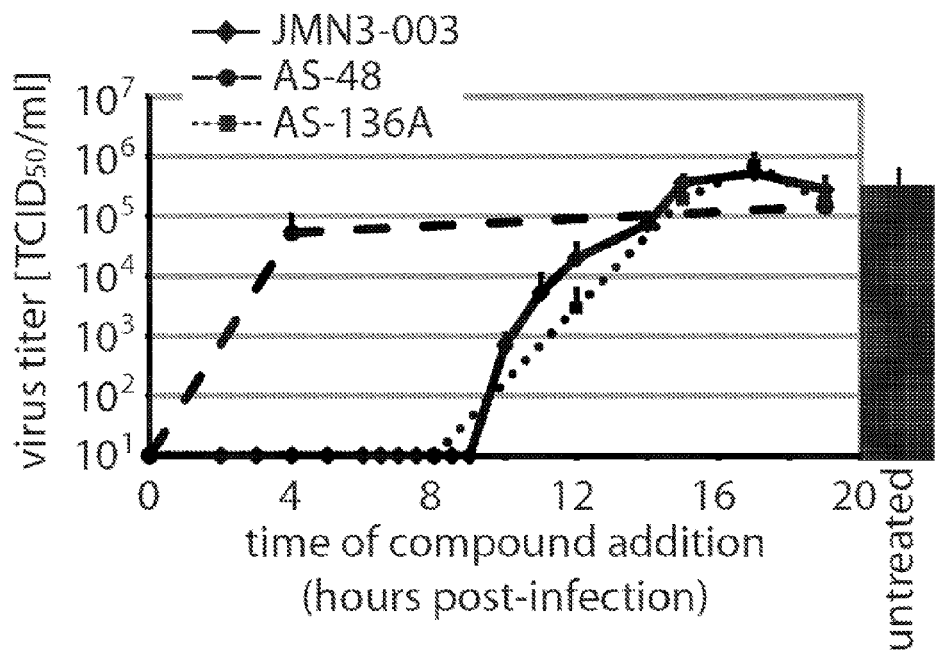

When added in a time-of-addition experiment at distinct time points post-infection in comparison with two previously characterized, pathogen-targeted antivirals, the inhibition profile of JMN3-003 was distinct from that of the entry inhibitor AS-48 but very closely resembled the profile of the AS-136A RdRp blocker class (FIG. 6E). Thus, these data point towards inhibition of the viral RdRp activity by JMN3-003 as one possible underlying mechanism for antiviral activity of the compound.

Example 7

Host-Directed Inhibitor of Viral RdRp Activity

Figure 7A:
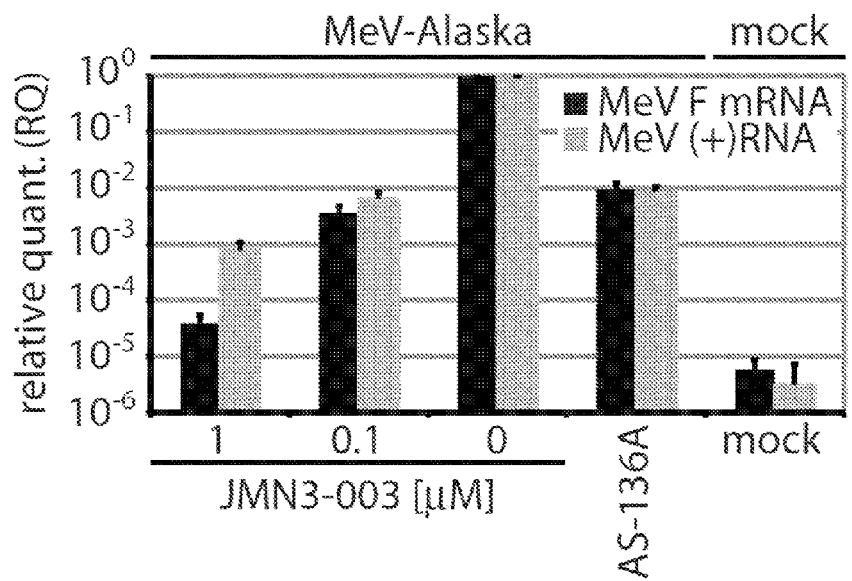
FIGS. 7A-C show data suggesting compound JMN3-003 inhibits viral RNA synthesis. A) Relative quantitations of MeV F mRNA and antigenome (+RNA) levels after incubation of infected cells in the presence of compound for 40 hours. Samples were normalized for vehicle only (DMSO)-treated cells and $\Delta\Delta$CT values calculated using cellular GAPDH as reference. Mock samples remained uninfected. Averages of three independent experiments, assessed in triplicate each, ±SD are shown. B) Quantitation of influenza A/WSN segment seven antigenome (+RNA) and of released progeny genomic RNA (genome copies) after incubation of infected MDCK cells in the presence of compound for 24 hours. For +RNA quantitation, samples were normalized and $\Delta\Delta$CT values calculated as outlined in (A). Released genome copies were quantified by TaqMan RT-PCR relative to an external standard, then normalized for vehicle-treated controls. Averages of four experiments, assessed in triplicate each, ±SD are shown. C) Luciferase reporter-based assessment of viral RdRp activity in the presence of JMN3-003. BHK-T7 cells transfected with plasmids encoding the MeV minireplicon reporter system were incubated in the presence of JMN3-003 or vehicle only for 36 hours. Values were normalized for luciferase activities found in vehicle (DMSO)-treated controls and represent averages of three experiments assessed in duplicate each±SD.

For myxovirus infection, the viral RdRp complex mediates both genome transcription and replication to express viral proteins and generate progeny genomes, respectively. Replication occurs through generation of an antigenome of positive polarity, which then serves as template for negative strand genome synthesis. To directly test whether JMN3-003 affects viral RdRp activity in the context of virus infection, the copy numbers of MeV-Alaska mRNA and antigenome was determined in infected, compound-treated cells relative to vehicle-treated controls by quantitative RT-PCR. Presence of JMN3-003 caused a dose-dependent reduction in viral RNA levels (FIG. 7A). At a concentration of 100 nM, for instance, a >100-fold reduction of viral mRNA and antigenome copy numbers were observed relative to vehicle-treated samples, indicating potent inhibition of viral replication. For comparison, a concentration of 25 µM of the RdRp inhibitor AS-136A, a nanomolar blocker of MeV replication, was required to achieve comparable mRNA and antigenome reduction levels (FIG. 7A).

Figure 7B:
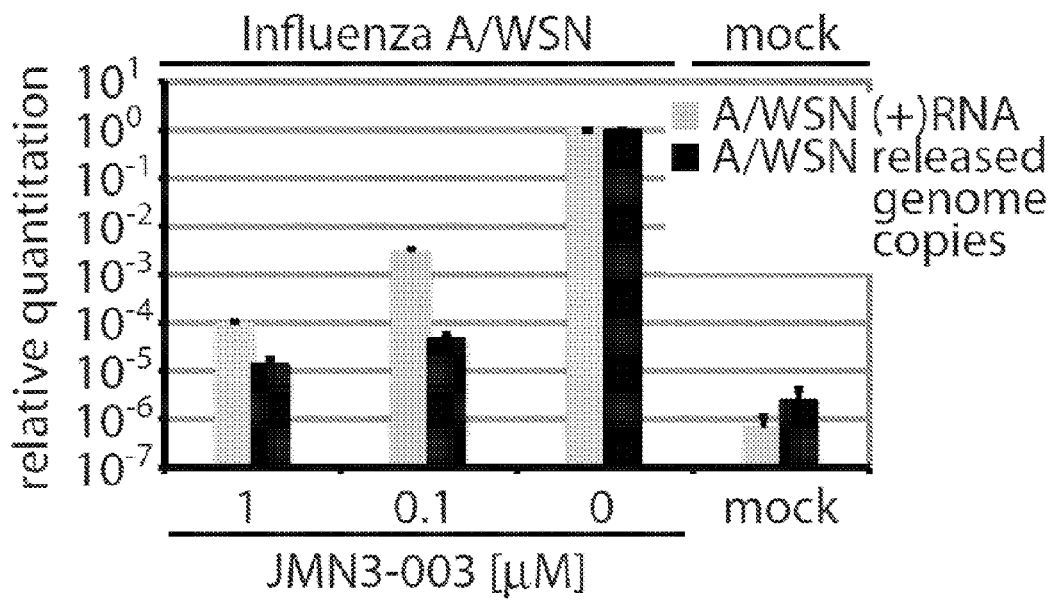
Figure 7C:
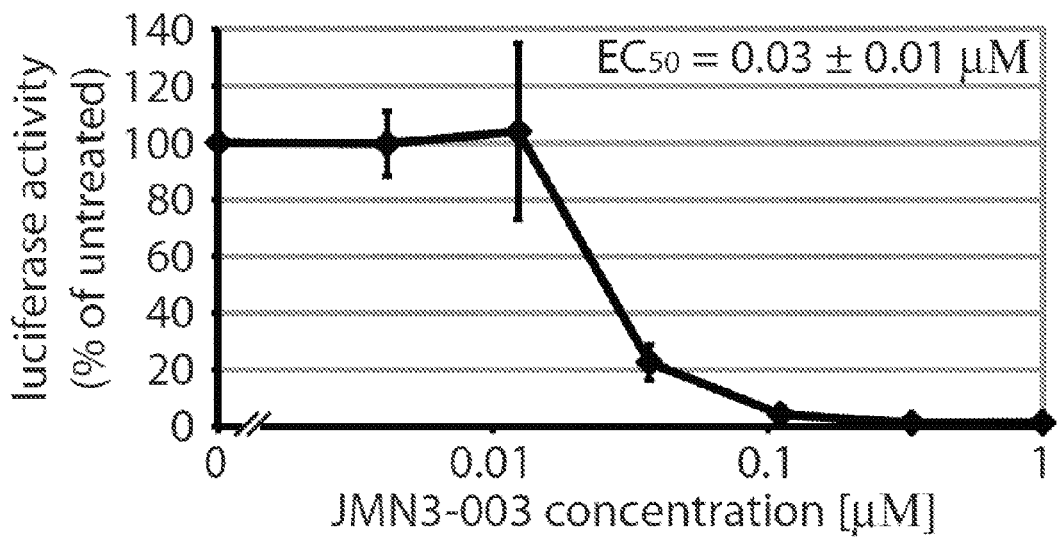

When this assay was applied to orthomyxovirus infection, a dose-dependent inhibition of influenza A/WSN antigenome levels were observed relative to vehicle treated controls (FIG. 7B). Parallel quantification of genome copy numbers of released progeny virus demonstrated that an approximate >100-fold drop in relative viral antigenome levels correlates to a >10,000-fold reduction in genome copies of released progeny virions (FIG. 7B). Assessment of viral RdRp activity in a plasmid-based minireplicon reporter system confirmed dose-dependent inhibition of RdRp by JMN3-003 also in a sub-infection setting, since luciferase reporter expression was fully blocked at compound concentrations of approximately 100 nM (FIG. 7C). Taken together, these data suggest indirect inhibition of the viral polymerase complex through interaction of the compound with a cellular cofactor required for RdRp activity as the basis for the antiviral effect of JMN3-003.

Example 8

JMN3-003 does not Induce Rapid Emergence of Viral Resistance

It has been suggested for different viral pathogens that a host-directed antiviral approach has the potential to reduce the frequency of viral escape from inhibition compared to direct targeting of pathogen components. To explore whether resistance to JMN3-003 could be induced experimentally, stepwise viral adaptation to growth was attempted in the presence of the compound in comparison with the pathogen-specific MeV RdRp inhibitor AS-136A.

Figure 8:
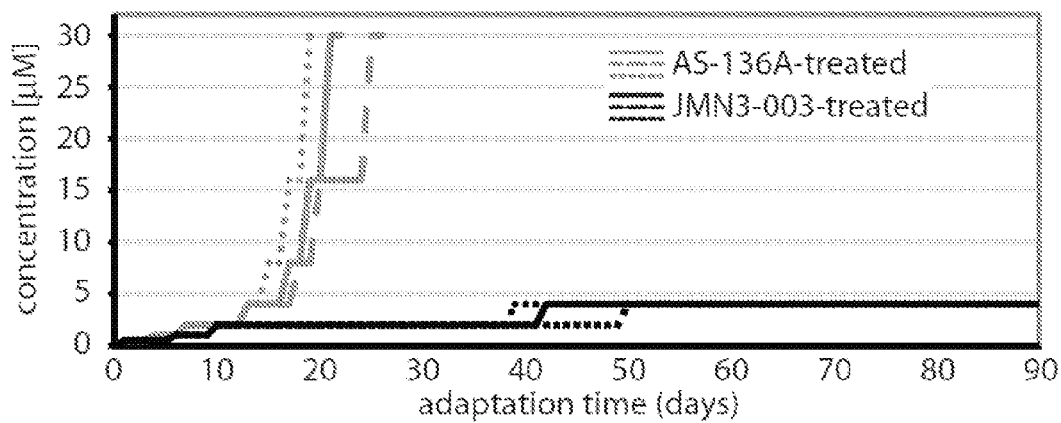
FIG. 8 shows data suggesting JMN3-003 prohibits rapid emergence of viral resistance in vitro. MeV-Alaska remains sensitive to the compound after continued adaptation events for a 90-day period, while resistance (extensive viral CPE detectable in the presence of 30 µM compound) to pathogen directed AS-136A emerges in step-wise adaptations after 15-25 days. Three independent adaptations (represented by solid, dotted and dashed lines, respectively) were pursued for each compound.

Following an escalating dose scheme, inhibitor concentrations were doubled when virus induced cytopathicity became detectable microscopically. While robust resistance to the pathogen-targeted AS-136A control emerged rapidly in an approximate 15 to 20-day time window (tolerated dose at the end of adaptation was ≥30 μM, equivalent to ≥100-fold resistance), only marginal increases in the tolerated dose could be detected for JMN3-003 after 90 days of continued viral incubation in the presence of the substance (FIG. 8). These results are consistent with a host-directed MOA of JMN3-003 and suggest the existence of a systemic barrier that prevents rapid viral escape from inhibition by the article.

Materials and Methods:

Cells and Viruses

Cell lines were maintained at 37° C. and 5% CO2 in Dulbecco's modified Eagle's medium supplemented with 10% fetal bovine serum. Vero (African green monkey kidney epithelial) cells (ATCC CCL-81) stably expressing human signaling lymphocytic activation molecule (CD 150w/SLAM), called in this study Vero-SLAM cells, and baby hamster kidney (BHK-21) cells stably expressing T7 polymerase (BSR-T7/5 (BHK-T7) cells) were incubated at every third passage in the presence of G-418 (Geneticin) at a concentration of 100 μg/ml. Lipofectamine 2000 (Invitrogen) was used for cell transfections. Peripheral blood mononuclear cells (PBMCs) were prepared through overlay of whole blood samples from mixed, healthy human donors on Ficoll Hypaque solution, followed by centrifugation at 240×g for 30 minutes at room temperature and removal of the interphase material. Red blood cells were lysed with RBC lysis solution (Sigma), followed by repeated washing of extracted PBMCs with phosphate buffered saline and transfer to tissue culture plates pre-coated with poly-L-lysine (Sigma). Virus strains used in this study were MeV isolate MVi/Alaska.USA/16.00, genotype H2 (MeV-Alaska), HPIV3, MuV strain South Africa, RSV strain Long, laboratory adapted influenza A strains WSN(H1N1) and PR8/34 (H1N1), and swine-origin influenza virus isolates S-OIV Texas and Mexico. To prepare virus stocks, cells permissive for the virus to be amplified (Vero-Slam, Vero, HepG2, and Madin-Darby canine kidney (MDCK)) were infected at a multiplicity of infection (MOI) of 0.001 plaque-forming units (pfu)/cell and incubated at 37° C. Cell-associated paramyxovirus particles were harvested by scraping cells in OPTIMEM (Invitrogen), followed by release of virus through two consecutive freeze-thaw cycles. Influenza virus particles were harvested from cell culture supernatants. Titers of MeV and MuV were determined through 50% tissue culture infective dose (TCID50) titration according to the Spearman-Karber method as described, titer of all other viruses were determined by plaque assay on permissive cells.

Influenza A Titration by TaqMan RT-PCR

To determine genome copy numbers of released progeny influenza A particles (strains WSN, PR8/34, S-OIV Texas and Mexico), culture supernatants of infected MDCK cells ($4 \times 10^5$ cells/well in a 12-well plate format) were harvested and total RNA prepared using a QIAcube automated extraction machine and the QIAamp viral RNA mini kit reagent. Purified RNA was then subjected to quantitative real time (qRT) PCR analysis using an Applied Biosystems 7500 Fast real-time PCR system and the qRT-PCR TaqMan Fast Virus 1-Step Master Mix (Applied Biosystems). Primers for amplification were 5'-GACCRATCCTGTCACCT CTGAC (SEQ ID NO: 1) and 5'-AGGGCATTYTGG ACAAAKCGTCTA (SEQ ID NO: 2); 5'-end 6-caboxyfluorescein and 3'-end Blackhole Quencher 1 labeled 5'-TGCAGTCCTCGCT CACTGGGCACG (SEQ ID NO: 3) (Biosearch Technologies) served as probe. Primers and probe are genome segment seven-specific and reportedly universally reactive with all influenza A strains including the recent S-OIV (H1N1) isolates. To generate a qRT-PCR standard, genome segment seven of influenza A/WSN was reverse transcribed, amplified, subcloned into pCR2.1-TOPO vector (Invitrogen) and sequence confirmed. The resulting standard plasmid was linearized through BamHI digest, spin purified and copy numbers calculated using Promega's BioMath Calculator tools (http://www.promega.com/biomath/). For each TaqMan reaction, 10-fold serial dilutions of the linearized plasmid ranging from 107 to 101 were prepared fresh and amplified in parallel to generate individual standard curves.

Compound Synthesis

To synthesize JMN3-003, N-(4-methoxyphenyl)-2-nitroaniline (FIG. 9A), P-anisidine (4.36 g, 35.4 mmol), 1-fluoro-2-nitrobenzene (3.8 ml, 36.0 mmol) and $Et_3N$ (4.93 ml, 35.4 mmol) were mixed in a microwave tube and heated at 150° C. for one hour. The mixture was stirred in water, ether added and the precipitate filtered. The reddish brown solid was washed with hexanes and dried under vacuum to give 8.0 g of substance (3) in 94% yield. $^1H$ NMR (400 MHz, $CDCl_3$, δ=7.24 ppm); (s, 1H), 10.01 (s, 1H), 8.18 (dd, J=8.0, 1.6 Hz, 1H), 7.33-6.68 (m, 7H), 3.83 (s, 3H).

For synthesis of N-(4-methoxyphenyl)benzene-1,2-diamine (substance (4) in FIG. 9A), 10% Pd/C (300.0 mg, 0.282 mmol) was added to a suspension of (3) (2.6 g, 10.65 mmol) in methanol (40.0 ml) and the mixture exposed to hydrogen at 40 psi for three hours. The mixture was filtered through a pad of celite and the filtrate concentrated. The resultant reddish brown oil was dried under vacuum to give a brown solid in quantitative yield.

To synthesize 1-(4-methoxyphenyl)-benzoimidazole-2-thiol (substance (5) FIG. 9A), a solution of substance (4) (7.0 g, 32.7 mmol) in $CH_2Cl_2$ (100.0 ml) at 0° C. was combined with 1,1-thiocarbonyldiimidazole (5.83 g, 35.9 mmol) and the mixture stirred for 30 minutes. The cold bath was removed and the mixture stirred for a further two hours before adding water (50 ml). The organic layer was separated and washed with water (50.0 ml), dried over $Na_2SO_4$, filtered and concentrated. The residue was triturated with $CH_2Cl_2$ and hexanes to give a grey solid (6.5 g 88% yield). $^1H$ NMR (400 MHz, $CDCl_3$, δ=7.24 ppm); δ10.7 (s, 1H), 7.46-7.42 (m, 2H), 7.28-7.09 (m, 5H), 6.95 (d, J=7.6 Hz, 1H), 3.93 (s, 3H).

To generate 2-bromo-N-(2-chloro-4-methylphenyl)propanamide (substance (6) in FIG. 9B), a solution of 2-chloro-4-methylaniline (3.0 g, 24.8 mmol) in $CH_2Cl_2$ (100.0 ml) at 0° C. was treated withi-$Pr_2NEt$ (6.5 ml, 37.3 mmol) and 2-bromo propionyl bromide (3.3 ml, 29.6 mmol) and the mixture stirred for one hour.

The organic layer was separated and washed with 1N NaOH (2×30.0 ml), dried over Na$_2$SO$_4$, filtered and concentrated to give a white solid (5.1 g, 74% yield) that was dried under vacuum and used without further purification. $^1$H NMR (400 MHz, CDCl$_3$, δ=7.24 ppm); δ 8.60 (s, 1H), 8.18, (d, J=8.4 Hz, 1H), 7.22 (s, 1H), 7.09 (d, J=8.0 Hz, 1H), 4.59 (q, J=7.2 Hz), 2.32 (s, 3H), 1.99 (d, J=7.2 Hz, 3H).

To obtain JMN3-003 as the final product, a suspension of substance (5) (300.0 mg, 1.17 mmol) in ethanol (10.0 ml) was combined with KOtBu (150.0 mg, 1.34 mmol) and the mixture stirred at room temperature for one hour. To the reaction was added substance (6) (340.0 mg, 1.23 mmol) and the mixture stirred for five hours. Concentrated NH$_4$Cl (10.0 ml) and dichloromethane (10.0 ml) were added to the reaction, the organic layer separated and washed with brine (10.0 ml), then dried over Na$_2$SO$_4$, filtered and concentrated. The crude product was purified by silica column chromotography (hexanes/ethylacetate) to give JMN3-003 (420.0 mg, 80% yield) as a white solid. $^1$H NMR (400 MHz, CDCl$_3$, δ=7.24 ppm); δ10.45 (s, 1H), 8.22 (d, J=8.4 Hz, 1H), 7.34-7.0 (m, 9H), 4.91 (q, J=7.6 Hz, 1H), 3.88 (s, 3H), 2.24 (s, 3H) 1.6 (d, J=7.2 Hz, 3H).

To synthesize 2-(benzoimidazol-2-yl)thio-N-(2-chloro-4-methylphenyl) propanamide (substance (8) in FIG. 9B), a solution of 2-mercaptobenzimidazole (500.0 mg, 3.33 mmol) in tetrahydrofuran (30.0 ml) was treated with NaH (150.0 mg, 3.75 mmol) and the mixture stirred for 10 minutes. Substance (6) (920.0 mg, 3.33 mmol) was added to the reaction and the mixture stirred for six hours. Water (15 ml) was added and the product extracted using ethylacetate, the organic layer then dried over Na$_2$SO$_4$, filtered and concentrated. The crude product was purified by silica column chromatography (hexanes/ethylacetate; 2:1) to give 740.0 mg of substance (8) in 64% yield. The product was used in consecutive steps without characterization. For synthesis of JMN5-165, a solution of substance (8) (supplement 1)(100.0 mg, 0.29 mmol) in CH$_2$Cl$_2$ (3.0 ml) was mixed with benzenesulfonyl chloride (40.0 mL, 0.31 mmol) and i-Pr$_2$NEt (80.0 mL, 0.46 mmol) and the reaction stirred for eight hours. NaHCO$_3$ (2.0 ml) was added to the reaction mixture, the organic layer separated and washed with brine (2.0 ml), then dried over Na$_2$SO$_4$ and concentrated. The crude product was purified by silica column chromatography (hexanes/ethylacetate) to give a white solid that was dried under vacuum. $^1$H NMR (400 MHz, CDCl$_3$, δ=7.24 ppm); δ 9.56 (s, 1H), 8.17 (d, J=8.0 Hz, 1H), 8.03-8.0 (m, 2H), 7.96-7.94 (m, 1H), 7.59-7.51 (m, 2H), 7.45-7.41 (m, 2H), 7.31-7.29 (m, 2H), 7.01-6.99 (m, 2H), 4.86 (q, J=7.2 Hz, 1H), 2.23 (s, 3H), 1.68 (d, J=7.6 Hz, 3H).

Synthesis of JMN5-166 followed the same protocol as described above for JMN5-165. $^1$H NMR (400 MHz, CDCl$_3$, δ=7.24 ppm); δ 10.02 (s, 1H), 8.26 (d, J=8.4 Hz, 1H), 7.73-7.65 (m, 4H), 7.54-7.51 (m, 2H), 7.28-7.24 (m, 1H), 7.10-7.09 (broad, 1H), 7.06-7.02 (m, 2H), 6.70 (d, J=8.4 Hz, 1H), 4.92 (q, J=7.2 Hz, 1H), 2.25 (s, 3H), 1.65 (d, J=7.2 Hz, 3H). To prepare inhibitor stocks, compounds were dissolved at 75 mM in DMSO.

Synthesis of (S)—N-(2-chloro-4-methylphenyl)-2-(1-(3-(2-morpholinoethyl)phenyl)-benzo[d]imidazol-2-yl)thio) propanamide In a 50 mL flask, 14342-morpholinoethyl)phenyl)-benzo[d]imidazole-2-thiol (375 mg, 1.105 mmol) and potassium carbonate (145 mg, 1.052 mmol) were suspended in 5 mL dry methanol with sonication and stirred at 45° C. for 2 hours. Then, the methanol was removed under reduced pressure and then coevaporated with dry acetonitrile, and then dried under high vacuum for one hour. This was then redissolved in 2 mL dry DMF, and added to a solution of (R)-2-bromo-N-(2-chloro-4-methylphenyl)propanamide (320 mg, 1.157 mmol) in 1 mL anhydrous DMF at 0° C. over 0.5 hours and stirred for 0.5 hours. The reaction was monitored by HPLC and TLC (5% MeOH in DCM; Rf of product=0.27). The reaction appeared to be complete within 30 minutes at 0° C. ee=95%; ee of starting material was 95%; Workup: 30 mL DCM and 3×20 mL water and 1×20 mL brine; MgSO4, filtered, and concentrated; dried under hi vac overnight; After a column (0 to 7% DCM in methanol), 397 mg (71% yield) of product.

Synthesis of (S)—N-(2-chloro-4-methylphenyl)-2-((1-(2-((4-methylpiperazin-1-yl)methyl)phenyl)-benzo[d]imidazol-2-yl)thio)propanamide in a 50 mL flask, 1-(2-((4-methylpiperazin-1-yl)methyl)phenyl)-benzo[d]imidazole-2-thiol (500 mg, 1.477 mmol) and potassium carbonate (194.4 mg, 1.407 mmol) were suspended in 10 mL dry methanol with sonication and stirred at 45° C. for 2 hours. Then, the methanol was removed under reduced pressure and then coevaporated with dry acetonitrile, and then dried under high vacuum overnight. This was then redissolved in 4 mL dry DMF, and added to a solution of (R)-2-bromo-N-(2-chloro-4-methylphenyl)propanamide (449.3 mg, 1.625 mmol) in 1 mL anhydrous DMF at 0° C. over 0.5 hours and stirred for 0.5 hours. The reaction was monitored by HPLC and TLC (10% MeOH in DCM; Rf of product=0.32). The reaction appeared to be complete within 30 minutes at 0° C. ee=94%; ee of starting material was 94%; Workup: 30 mL DCM and 3×20 mL water and 1×20 mL brine; MgSO4, filtered, and concentrated; dried under hi vac overnight; After a 25 g silica gel column (8% methanol in DCM), 530 mg (70.5% yield) of product was obtained as a white foam.

Viral CPE-Reduction Assay

To rapidly pre-screen small libraries of compound analogs for antiviral activity, Vero-SLAM cells were infected with MeV-Alaska in four replicates per compound concentration in a 96-well plate format at an MOI of 0.4 pfu/cell in the presence of the inhibitor analyzed ranging from 75 µM to 293 nM in two-fold dilutions. At 96 hours post-infection, cell monolayers were subjected to crystal violet staining (0.1% crystal violet in 20% ethanol), and the absorbance of dried plates at 560 nm determined. Virus-induced cytopathicity was then calculated according to the formula [% rel. CPE=100-(experimental-minimum)/(maximum-minimum)*100], with minimum referring to infected, vehicle-treated wells and maximum to mock-infected wells.

Virus Yield Reduction Assay

To assess viral resistance to inhibition based on reduction of titers of infectious particles, 2×10$^5$ cells per well were infected in a 12-well plate format with the specified myxovirus at an MOI=0.1 pfu/cell (all paramyxoviruses assessed) or 0.05 pfu/cells (influenza viruses) in the presence of a range of compound concentrations as indicated or equivalent volumes of solvent (DMSO) only, and incubated in the presence of compound at 37° C. When vehicle treated controls approached the end of the logarithmical growth phase (typically 28-36 hours postinfection depending on the virus assessed), progeny viral particles were harvested and tittered by TCID50 titration, plaque assay or TaqMan real-time PCR, respectively, as described above. Plotting virus titers as a function of compound concentration allowed quantitative assessment of resistance. Where applicable, 50% inhibitory concentrations were calculated using the variable slope (four parameters) non-linear regression-fitting algorithm embedded in the Prism 5 software package (GraphPad Software).

Quantification of Compound Cytotoxicity

A non-radioactive cytotoxicity assay (CytoTox 96 Non-Radioactive Cytotoxicity Assay, Promega) was employed to metabolic activity of cell after exposure to a compound. In a 96-well plate format, 10,000 cells per well were incubated at 37° C. for 24 hours in four replicates per concentration tested in the presence of compound ranging from 75 µM to 293 nM in two-fold dilutions. Conversion of a tetrazolium salt (INT) into a colored formazan product by cellular lactate dehydrogenase released into the culture supernatants was then measured at 490 nm using a BioRad plate reader. Values were calculated according to the formula [% toxicity=100−((experimental−background)/(maximum(vehicle treated)−background)*100)]. Values were plotted in dose-response curves and, if applicable, CC50 concentrations calculated using the Prism 5 software package.

In Vitro Assessment of Metabolic and Plasma Stability

To estimate metabolic stability of the article, JMN3-003 was mixed with liver S9 fractions (protein concentration 2.5 mg/ml) from pooled mixed gender humans (XenoTech) at a final concentration of 1 µM and reactions initiated by the addition of cofactors (1.14 mM NADPH, 1.43 mM glucose-6-phosphate, 1.43 mM uridine 5'-diphosphoglucuronic acid, 9.42 mM potassium chloride, 2.28 mM magnesium chloride) in 100 mM potassium phosphate buffer, pH 7.4. Samples were incubated at 37° C. with mixing, aliquots removed after 0, 15, 30 and 60 minutes and subjected to methanol precipitation. Cleared supernatants were analyzed by reversed-phase LC-MS/MS (Applied Biosystems API 4000 QTRAP with heated nebulizer (Turbo IonSpray for JMN5-166) and peak areas measured to calculate half life and percent of input compound remaining according to the formulas t½=(−0.693/slope of linear regression analysis of log transformed peak area versus) and % input remaining=(peak area of test compound at tx/peak area of test compound at t0)*100. Positive controls to assess the metabolic competency of the liver S9 fractions were 7-Ethoxycoumarin, Propranolol, and Verapamil (Sigma), which were analyzed in parallel to the article. To determine compound plasma stability, articles were mixed with freshly prepared human plasma at a final concentration of 0.5 mM and incubated at 37° C. for up to 120 minutes. Aliquots were removed at distinct time points as indicated, subjected to methanol precipitation of plasma proteins, and cleared supernatants analyzed by LC-MS/MS with detection of the compound at 254 nm. Values are expressed as percent of compound remaining at each time relative to the amount of that compound present at the starting time point.

Flow-Cytometric Analysis of Cell Cycle Progression

Actively proliferating HeLa cells were exposed to JMN3-003 (10 µM), hydroxyurea (4 mM), or nocodazole (200 ng/ml) for 36 hours, followed by resuspension in buffer I (20 mM citrate/PO, pH 3.0, 0.1 mM EDTA, 0.2 M Sucrose, 0.1% Triton X-100) and staining in buffer II (10 mM Citrate/PO, pH 3.8, 0.1M sodium chloride, 20 µg/ml acridine orange). Green fluorescence at 525 nm resulting from DNA intercalating acridine orange was then measured using a BD LSRII flow cytometer and FlowJo software (Tree Star) for data analysis. For comparison, unstained and stained, solvent-only exposed cells were examined in parallel.

SDS-PAGE and Immunoblotting

For immunodetection of viral glycoproteins or cellular proteins, cells were lysed with RIPA buffer (50 mM Tris/CL, pH 7.2, 1% deoxycholate, 0.15% sodium dodecylsulfate, 150 mM sodium chloride, 50 mM sodium fluoride, 10 mM EDTA, 1% NP-40, 1 mM PMSF, protease inhibitors). Aliquots with equal total concentrations of cleared lysates (20,000×g; 10 min; 4° C.) were mixed with 2×-urea buffer (200 mM Tris, pH 6.8; 8 M urea; 5% sodium dodecyl sulfate (SDS); 0.1 mM EDTA; 0.03% bromphenolblue; 1.5% dithiothreitol) and denatured for 25 min at 50° C. Samples were then fractionated on 10% SDS-polyacrylamide gels, blotted to polyvinylidene difluoride (PVDF) membranes (Millipore) and subjected to enhanced chemiluminescence detection (Pierce) using specific antisera directed against phosphorylated or non-phosphorylated cdc2-cyclin B kinase (Cell Signaling Technology), GAPDH (Abcam), the cytosolic tail of the MeV F protein, or influenza A/WSN virus M2 (Thermo Scientific).

Immunostained PVDF membranes were developed using a ChemiDoc XRS digital imaging system (Bio-Rad) and horseradish peroxidase conjugated anti-species IgG (mouse or rabbit) antibodies. For densitometry, signals were quantified using the QuantityOne software package (Bio-Rad).

Assessment of Cell Growth Rates

To determine cell proliferation rates, Vero cells were seeded at a density of $6 \times 10^5$ cells per well in a 6-well plate format and incubated in the presence of 10 µM JMN3-003 or vehicle only for 30 hours at 37° C. Cells were then washed extensively and reseeded at a density of $1 \times 10^5$ cells per well, followed by continued incubation at 37° C. and assessment of life/dead cell numbers every 24 hours using a Countess automated cell counter (Invitrogen). Cells were reseeded as before when fastest growing cultures approached confluency. Growth rates were calculated for each 24-hour time interval using the Prism software package (GraphPad Software Inc.) based on the formula $Y=Y0*\exp(K*X)$ with Y equaling life cell numbers, Y0 the Y value at the starting time (t0), and K the growth constant equaling $\ln(2)$/doubling-time.

Quantification of Cellular and Viral mRNA Levels

For quantitative RT-PCR, cells were infected in a 6-well plate format with either recombinant MeV Edmonston (recMeV-Edm)(Vero cells, MOI=1.0) or influenza A/WSN (MDCK cells, MOI=0.05), followed by removal of inocula one hour post-infection and addition of JMN3-003 in growth media at 0.1 µM or 1 µM. All MeV infected wells received in addition fusion inhibitory peptide (FIP, Bachem) at 100 µM to prevent premature breakdown of the monolayer through viral CPE in the vehicle control wells prior to RNA extraction. Twenty-four (influenza A/WSN) or forty (recMeV-Edm) hours post-infection, total RNA was prepared from wells using the QIAcube automated extractor and the RNeasy Mini Kit (Qiagen), and subjected to reverse transcription using Superscript II Reverse Transcriptase (Invitrogen). For RNA samples originating from recMeV-Edm infected cells, antigenome-specific primer 5-GGCTCCCTCTG GTTGT (SEQ ID NO: 4) (annealing to antigenome nucleotides 4962-4977 in reverse orientation) or oligo-dT primer (viral mRNA and GAPDH quantification) were used for cDNA priming. In the case of samples originating from influenza A/WSN infected cells, primers for cDNA synthesis were 5-AGTAGAAA-CAAGGTAGTTT (SEQ ID NO: 5) (antigenome) or oligo-dT (mRNA and canine GAPDH). Real-time reactions were carried out using an Applied Biosystems 7500 Fast real-time PCR system and iQFast SYBR Green Supermix with ROX (Bio-Rad). Probes were a fragment at the N/P junction (MeV antigenomic RNA, 5-AACCAGGTCCACACAG (SEQ ID NO:6) and 5-GTTGTCTGATATTTCTGAC (SEQ ID NO: 7)), a fragment of MeV F mRNA (5-GTCCAC-CATGGGTCTCAAGGTGAACGTCTC (SEQ ID NO: 8) and 5-CAGTTATTGAGG AGAGTT (SEQ ID NO: 9)), a fragment of human GAPDH (SABiosciences proprietary primers), a fragment of influenza A/WSN segment seven (influenza A/WSN antigenomic RNA, 5-TAGCTCCAGT-GCTTGGTCT (SEQ ID NO:10) and 5-AAGGCCCTC-CTTTCAGTCC (SEQ ID NO: 11)), a fragment of influenza A/WSN M2 spliced mRNA (5-AACCGAGGTC-GAAACGCCTA (SEQ ID NO: 12) and 5-AGCATCCA-CAGCACTCTGC (SEQ ID NO: 13)), and a fragment of canine GAPDH (Qiagen proprietary primer). Melting curves were generated at the end of each reaction to verify amplification of a single product. To calculate ΔΔCT values, CT values obtained for each sample were normalized for GAPDH as reference and then ΔCT values of JMN3-003-treated samples normalized for the FIP-treated controls. Final quantification was based on three independent experiments in which each treatment condition and RT primer setting were assessed in triplicate.

To assess the relative quantities of cellular mRNA, $9 \times 10^5$ HeLa cells were incubated in the presence of JMN3-003 (0.01, 0.1, 1.0 µM final concentration), AS-136A (25 µM), Actinomycine D (5 µg/µl), or vehicle only for six hours at 37° C., followed by preparation of total RNA as described above. Quantitative TaqMan RT-PCR was again achieved using the TaqMan Fast Master Mix (Applied Biosystems) combined with proprietary primer and probe sets specific for Induced myeloid leukemia cell differentiation protein 1-(MCL1), MAPK phosphatase 1 (MKP1), and ankyrin repeat and SOCS box-containing protein 7-(ASB7) encoding mRNAs (Applied Biosystems). Samples were standardized for GAPDH as before and normalized values expressed relative to the equally analyzed vehicle-treated controls.

Quantitative Cell-to-Cell Fusion Assays

To quantify fusion activity, an effector cell population ($3 \times 10^5$ cells/well) was cotransfected with 2 µg each of MeV H and F expression plasmids. To inhibit fusion until the cell overlay, the effector cells are incubated in the presence of 100 µM fusion inhibitory peptide (Bachem). Single transfections of plasmids encoding MeV F served as controls. Target cells ($6 \times 10^5$ cells/well) were transfected with 4 µg of the reporter plasmid encoding firefly luciferase under the control of the T7 promoter. Two hours post-transfection, modified vaccinia virus Ankara expressing T7 polymerase at an MOI of 1.0 PFU/cell was added to the effector cells. Following incubation for 16 h at 37° C., target cells were detached and overlaid on washed effector cells at a 1:1 ratio and incubated at 37° C. in the presence of different JMN3-003 concentrations as indicated. Four hours post-overlay, cells were lysed using Bright Glo lysis buffer (Promega), and the luciferase activity determined in a luminescence counter (PerkinElmer) after addition of Britelite substrate (PerkinElmer). The instrument's arbitrary values were analyzed by subtracting the relative background provided by values of the controls, and these values were normalized against the reference constructs indicated in the figure legends. On average, background values were <1% of the values obtained for reference constructs. For qualitative assessment, transfected Vero-SLAM cells were photographed 18 hours post-transfection at a magnification of ×200.

Time of Compound Addition Analysis

For virus pre-incubation assays, $10^7$ infectious MeV-Alaska particles were incubated for 60 minutes at 37° C. in the presence of JMN3-003 (1.0 µM final concentration) or vehicle only, followed by 1,000-fold dilution in growth media and transferred to $3 \times 10^5$ Vero-Slam cells/well in a 6-well plate format (corresponding to final compound concentrations after pre-incubation of 1 nM and an MOI=0.033). Reference wells were kept at 1.0 µM JMN3-003 for the duration of the experiment. Cell-associated viral particles were harvested 24 hours post-infection and infectious titers determined by TCID50 titration.

To assess cell priming, Vero-Slam cells ($3 \times 10^5$ cells/well in a 12-well plate format) were incubated in the presence of JMN3-003 at 1.0 µM for one hour at 37° C. at the indicated time points pre-infection, followed by extensive washing and further incubation in growth media. Immediately before infection, cells were reseeded at a density of $2.5 \times 10^5$ per well and infected with MeV-Alaska at an MOI=0.2 pfu/cell. Inocula were replaced with growth media four hours post-infection and cells incubated for approximately 20 hours (when ~90% of cells in vehicle only treated control wells showed virus-characteristic CPE). Cell-associated viral particles were then harvested and infectious titers determined by TCID50 titration.

For post-infection time-of-addition studies, $3 \times 10^5$ Vero-Slam cells/well infected with MeVAlaska as before, followed by addition of JMN3-003 (1.0 µM final concentration), entry inhibitor AS-48 (75 µM), or RdRp inhibitor AS-136A (25 µM). Controls received vehicle only. All wells were harvested 19 hours post-infection and titers of cell-associated progeny virus determined by TCID50 titration.

Minireplicon Assays

To assess MeV RdRp activity independent of MeV infection, BSR T7/5 cells ($5 \times 10^5$ per well in a 6-well plate format) were transfected with plasmid DNAs encoding MeV-L (0.24 µg), MeV-N (0.94 µg) or MeV-P (0.29 µg) and 2 µg of the MeV luciferase minigenome reporter plasmid. Control wells included identical amounts of reporter and helper plasmids but lacked the L encoding plasmid. At the time of transfection, JMN3-003 was added in a range of concentrations as specified, while control wells received vehicle only for comparison. Thirty-six hours post-transfection, cells were lysed with Bright GLO lysis buffer and relative luciferase activities determined using the Britelite substrate and a luminescence counter as outlined above.

In Vitro Virus Adaptation

To assess the emergence of viral resistance to inhibition, adaptation attempts were carried out. Vero-SLAM cells were infected with MeV-Alaska at an MOI of 0.1 pfu/ml and incubated in the presence of gradually increasing JMN3-003 concentrations starting at 0.5 µM. Equally infected cells treated with the virus polymerase targeted RdRp inhibitor AS-136A were examined in parallel for comparison. When cultures became overconfluent, cells were diluted and reseeded for continued incubation in the presence of the same compound concentration as before. At detection of extensive cell-to-cell fusion, cell-associated viral particles were released by two freeze/thaw cycles, diluted 10-fold and used for parallel infections of fresh cell monolayers in the presence of compound at unchanged and doubled concentrations. Cultures treated with the highest compound concentrations in which virus-induced cytopathicity became eventually detectable were used for further adaptation. The approach was terminated after 90 days of continued incubation or when virus-induced cytopathicity was readily detectable in the presence of 30 µM compound.

What is claimed:

1. A pharmaceutical composition comprising a pharmaceutically acceptable carrier, diluent or excipient and a compound selected from:

N-(2-chloro-4-methylphenyl)-2-((1-(4-(morpholinomethyl)phenyl)-benzo[d]imidazol-2-yl)thio)propanamide;

N-(2-chloro-4-methylphenyl)-2-((1-(4-(cyanomethoxy)phenyl)-benzo[d]imidazol-2-yl)thio)propanamide;

N-(2-chloro-4-methylphenyl)-2-((1-(4-(2-hydroxyethoxy)phenyl)-benzo[d]imidazol-2-yl)thio)propanamide;

N-(2-chloro-4-methylphenyl)-2-((1-(4-(2-(dimethylamino)ethyl)amino)phenyl)-benzo[d]imidazol-2-yl)thio)propanamide;

N-(2-chloro-4-methylphenyl)-2-((1-(4-(2-(dimethylamino)ethyl)(methyl)amino)phenyl)-benzo[d]imidazol-2-yl)thio)propanamide;

2-((1-(4-(2-acetamidoethoxy)phenyl)-benzo[d]imidazol-2-yl)thio)-N-(2-chloro-4-methylphenyl)propanamide;

N-(2-chloro-4-methylphenyl)-2-((1-(4-(2-oxoethyl)phenyl)-benzo[d]imidazol-2-yl)thio)propanamide;

N-(2-chloro-4-methylphenyl)-2-((1-(4-(2-hydroxyethyl)phenyl)-benzo[d]imidazol-2-yl)thio)propanamide;

N-(2-chloro-4-methylphenyl)-2-((1-(4-(2-(methylamino)ethyl)phenyl)-benzo[d]imidazol-2-yl)thio)propanamide;

2-(4-(2-((1-(2-chloro-4-methylphenyl)amino)-1-oxopropan-2-yl)thio)-benzo[d]imidazol-1-yl)phenoxy)acetic acid;

methyl 2-(4-(2-((1-((2-chloro-4-methylphenyl)amino)-1-oxopropan-2-yl)thio)-benzo[d]imidazol-1-yl)phenoxy)acetate;

2-((1-(4-aminophenyl)-benzo[d]imidazol-2-yl)thio)-N-(2-chloro-4-methylphenyl)propanamide;

N-(2-chloro-4-methylphenyl)-2-((1-(4-hydroxyphenyl)-benzo[d]imidazol-2-yl)thio)propanamide;

N-(2-chloro-4-methylphenyl)-2-((1-(4-ethoxyphenyl)-benzo[d]imidazol-2-yl)thio)propanamide;

N-(2-chloro-4-methylphenyl)-2-((1-(4-(dimethylamino)phenyl)-benzo[d]imidazol-2-yl)thio)propanamide;

N-(2-chloro-4-methylphenyl)-2-((1-(4-(4-methylpiperazin-1-yl)phenyl)-benzo[d]imidazol-2-yl)thio)propanamide;

N-(2-chloro-4-methylphenyl)-2-((1-(4-morpholinophenyl)-benzo[d]imidazol-2-yl)thio)propanamide;

N-(2-chloro-4-methylphenyl)-2-((1-(4-(hydroxymethyl)phenyl)-benzo[d]imidazol-2-yl)thio)propanamide;

2-((1-(4-azidophenyl)-benzo[d]imidazol-2-yl)thio)-N-(2-chloro-4-methylphenyl)propanamide;

4-(2-((1-(2-chloro-4-methylphenyl)amino)-1-oxopropan-2-yl)thio)-benzo[d]imidazol-1-yl)benzoic acid;

N-(2-chloro-4-methylphenyl)-2-((1-(4-((dimethylamino)methyl)phenyl)-benzo[d]imidazol-2-yl)thio)propanamide;

methyl 4-(2-((1-((2-chloro-4-methylphenyl)amino)-1-oxopropan-2-yl)thio)-benzo[d]imidazol-1-yl)benzoate;

N-(2-chloro-4-methylphenyl)-2-((1-(4-methoxyphenyl)-benzo[d]imidazol-2-yl)thio)propanamide;

N-(2-chloro-4-methylphenyl)-2-((1-phenyl-benzo[d]imidazol-2-yl)thio)propanamide;

N-(2-chloro-4-methylphenyl)-2-((1-(3-methoxyphenyl)-benzo[d]imidazol-2-yl)thio)propanamide;

N-(2-chloro-4-methylphenyl)-2-((1-(m-tolyl)-benzo[d]imidazol-2-yl)thio)propanamide;

N-(2-chloro-4-methylphenyl)-2-((1-(3,5-dimethoxyphenyl)-benzo[d]imidazol-2-yl)thio)propanamide;

N-(2-chloro-4-methylphenyl)-2-((1-(3-(morpholinomethyl)phenyl)-benzo[d]imidazol-2-yl)thio)propanamide;

3-(2-((1-((2-chloro-4-methylphenyl)amino)-1-oxopropan-2-yl)thio)-benzo[d]imidazol-1-yl)benzoic acid;
N-(2-chloro-4-methylphenyl)-2-((1-(2-(morpholinomethyl)phenyl)-benzo[d]imidazol-2-yl)thio)propanamide;
N-(2-chloro-4-methylphenyl)-2-((1-(3-(hydroxymethyl)phenyl)-benzo[d]imidazol-2-yl)thio)propanamide;
N-(2-chloro-4-methylphenyl)-2-((1-(2-(hydroxymethyl)phenyl)-benzo[d]imidazol-2-yl)thio)propanamide;
N-(2-chloro-4-methylphenyl)-2-((1-(4-methoxybenzyl)-benzo[d]imidazol-2-yl)thio)propanamide;
N-(2-chloro-4-methylphenyl)-2-((1-(phenylsulfonyl)-benzo[d]imidazol-2-yl)thio)propanamide; and
N-(2,4-dichlorophenyl)-2-((1-(4-methoxybenzyl)-benzo[d]imidazol-2-yl)thio)propanamide, or salts thereof.

* * * * *